United States Patent [19]
Scirica et al.

[11] Patent Number: 5,938,668
[45] Date of Patent: *Aug. 17, 1999

[54] SURGICAL SUTURING APPARATUS

[75] Inventors: Paul A. Scirica, Huntington; Charles R. Sherts, Southport; Richard Yagami, Ridgefield; David Farascioni, Bethel, all of Conn.

[73] Assignee: United States Surgical, Norfolk, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/726,111

[22] Filed: Oct. 4, 1996

Related U.S. Application Data

[63] Continuation-in-part of application No. 08/662,493, Jun. 13, 1996, Pat. No. 5,713,531, which is a continuation of application No. 08/319,840, Oct. 7, 1994, abandoned.

[51] Int. Cl.$^6$ .................................................. A61B 17/04
[52] U.S. Cl. ........................... 606/145; 606/144; 606/139
[58] Field of Search .................................... 606/148, 147, 606/145, 144, 139, 151, 205, 207

[56] References Cited

U.S. PATENT DOCUMENTS

| | | |
|---|---|---|
| 1,037,864 | 9/1912 | Carlson et al. . |
| 1,131,163 | 3/1915 | Saunders et al. . |
| 1,293,565 | 2/1919 | Smit . |
| 1,449,087 | 3/1923 | Bugbee . |
| 1,876,792 | 6/1932 | Thompson . |
| 2,213,830 | 9/1940 | Anastasi . |
| 2,601,564 | 6/1952 | Smith ...................................... 606/144 |
| 2,880,728 | 4/1959 | Rights . |
| 3,073,311 | 1/1963 | Tibbs et al. . |
| 3,090,386 | 5/1963 | Curtis . |
| 3,349,772 | 10/1967 | Rygg . |
| 3,470,875 | 10/1969 | Johnson . |
| 3,807,407 | 4/1974 | Schweizer . |

(List continued on next page.)

FOREIGN PATENT DOCUMENTS

| | | |
|---|---|---|
| 0482881 | 4/1992 | European Pat. Off. . |
| 0535906 | 4/1993 | European Pat. Off. . |
| 0601676 | 6/1994 | European Pat. Off. . |
| 0647431 | 4/1995 | European Pat. Off. . |
| 337579 | 9/1904 | France . |
| 9109097 | 10/1991 | Germany . |
| 4124383 | 5/1992 | Germany . |
| 4124381 | 8/1992 | Germany . |
| 4127812 | 2/1993 | Germany . |
| 4139628 | 3/1993 | Germany . |

(List continued on next page.)

OTHER PUBLICATIONS

Aesculp Catalog, p. 401 (Date 1905).
"Surgeon's Stitch Gun Never Releases Needle", Design in Action, vol. 905 Machine Design 55, (1962, 63) 5,117.

*Primary Examiner*—Michael Buiz
*Assistant Examiner*—Tina T. D. Pham

[57] ABSTRACT

The surgical suturing apparatus is configured to pass a surgical suturing needle having an associated length of suture material attached thereto between opposed pairs of jaws. The surgical suturing apparatus generally includes a housing having an elongated tubular portion extending distally therefrom. A pair of jaws extend distally from the elongated tubular portion and are each individually longitudinally movable with respect to the elongated tubular portion and with respect to each other. Each of the jaw structures includes a jaw and a securing mechanism for tightly holding the surgical needle within the jaw. Parts of the securing mechanism engaging the needle also move longitudinally with respect to the associated jaw and the elongated tubular portion. Various control structures are provided to advance the securing mechanism relative to its associated jaw to secure the surgical needle therein and to move the entire jaw structure longitudinally with respect to the suturing apparatus.

29 Claims, 47 Drawing Sheets

U.S. PATENT DOCUMENTS

| | | |
|---|---|---|
| 3,842,840 | 10/1974 | Schweizer . |
| 3,901,244 | 8/1975 | Schweizer . |
| 3,946,740 | 3/1976 | Bassett . |
| 4,021,896 | 5/1977 | Stierlein . |
| 4,109,658 | 8/1978 | Hughes . |
| 4,161,951 | 7/1979 | Scanlan, Jr. . |
| 4,164,225 | 8/1979 | Johnson et al. . |
| 4,236,470 | 12/1980 | Stenson . |
| 4,345,601 | 8/1982 | Fukuda . |
| 4,373,530 | 2/1983 | Kilejian . |
| 4,471,781 | 9/1984 | DiGiovanni et al. . |
| 4,491,135 | 1/1985 | Klein . |
| 4,580,567 | 4/1986 | Schweitzer et al. . |
| 4,621,640 | 11/1986 | Mulhollan et al. . |
| 4,635,638 | 1/1987 | Weintraub et al. . |
| 4,827,931 | 5/1989 | Longmore . |
| 4,890,615 | 1/1990 | Caspari et al. . |
| 4,923,461 | 5/1990 | Caspari et al. . |
| 4,935,027 | 6/1990 | Yoon . |
| 4,957,498 | 9/1990 | Caspari et al. . |
| 4,983,176 | 1/1991 | Cushman et al. . |
| 5,059,201 | 10/1991 | Asnis . |
| 5,100,421 | 3/1992 | Christoudias . |
| 5,171,257 | 12/1992 | Ferzli . |
| 5,188,636 | 2/1993 | Fedotov . |
| 5,207,693 | 5/1993 | Phillips . |
| 5,217,471 | 6/1993 | Burkhart . |
| 5,224,948 | 7/1993 | Abe et al. . |
| 5,242,458 | 9/1993 | Bendel et al. . |
| 5,254,126 | 10/1993 | Filipi et al. . |
| 5,261,917 | 11/1993 | Hasson et al. . |
| 5,281,220 | 1/1994 | Blake, III . |
| 5,300,082 | 4/1994 | Sharpe et al. . |
| 5,336,191 | 8/1994 | Davis et al. . |
| 5,336,230 | 8/1994 | Leichtling et al. . |
| 5,389,103 | 2/1995 | Melzer et al. . |
| 5,603,718 | 2/1997 | Xu .......................................... 606/147 |
| 5,728,135 | 3/1998 | Bregen et al. . |

FOREIGN PATENT DOCUMENTS

| | | |
|---|---|---|
| 1103854 | 7/1984 | U.S.S.R. . |
| 1505514 | 9/1989 | U.S.S.R. . |
| 1725847 | 4/1992 | U.S.S.R. . |
| 914298 | of 0000 | United Kingdom . |
| 586661 | of 1947 | United Kingdom . |
| 1249853 | 10/1971 | United Kingdom . |
| 2260704 | 4/1993 | United Kingdom . |
| 9301750 | 2/1993 | WIPO . |

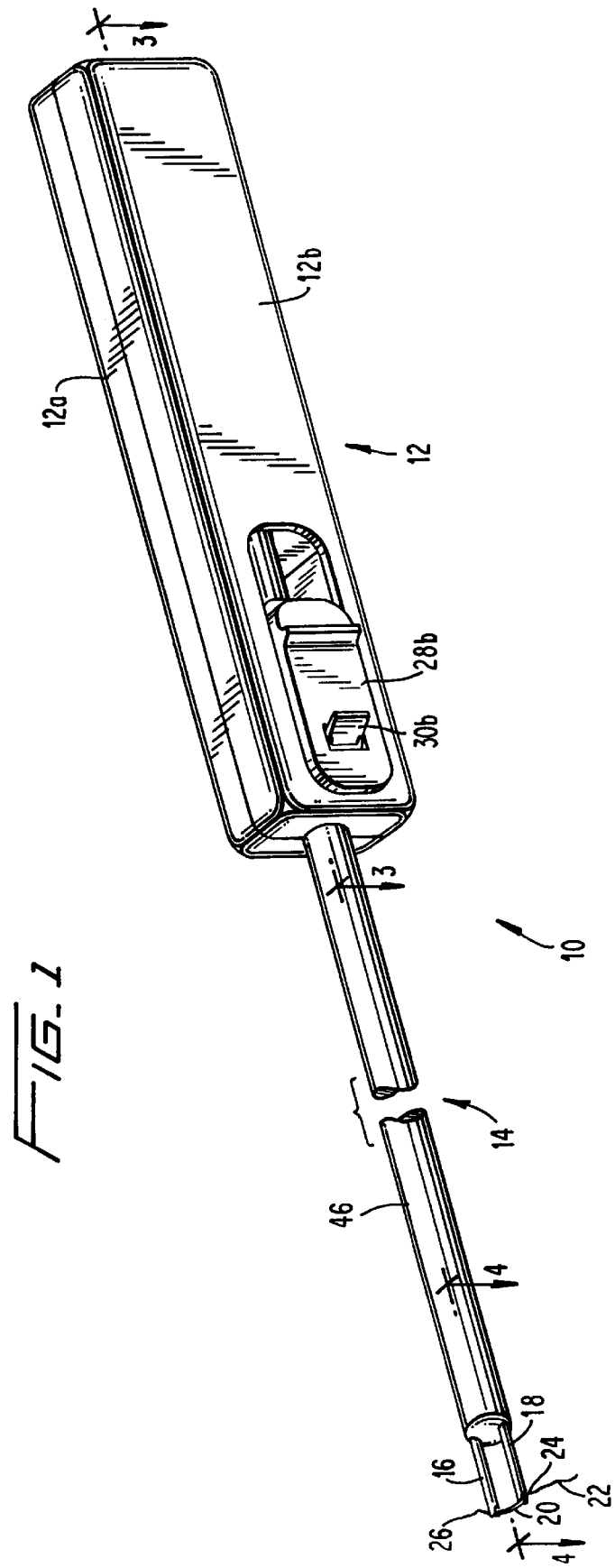

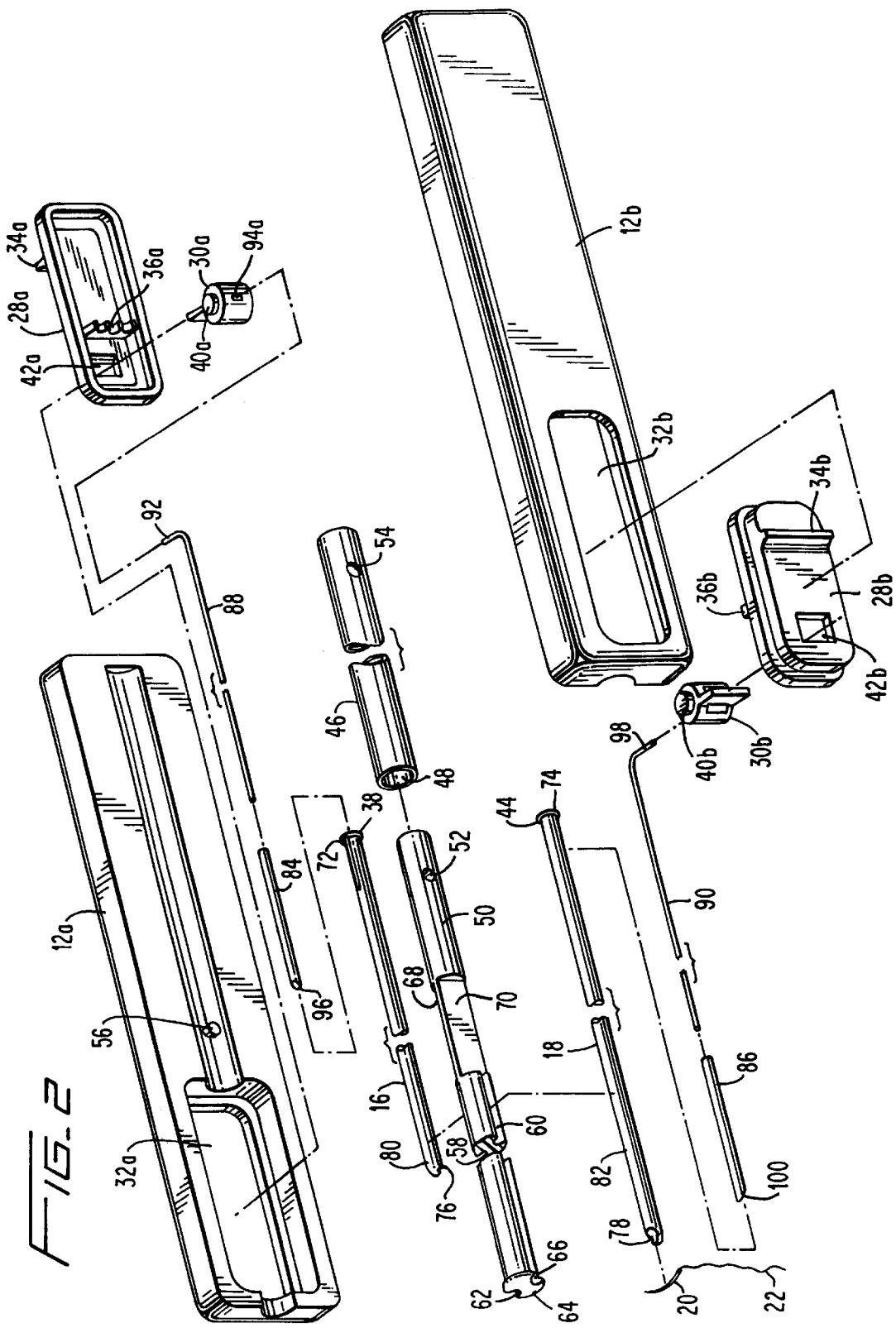

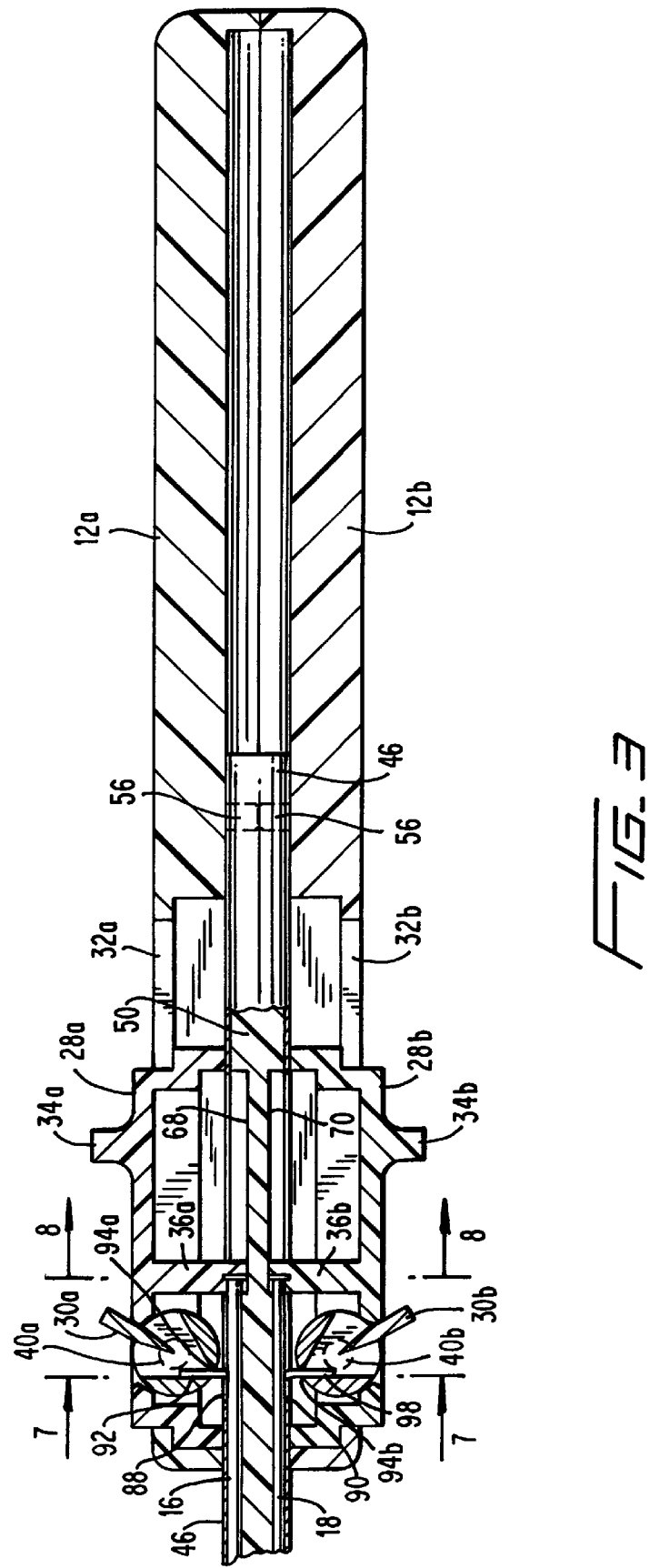

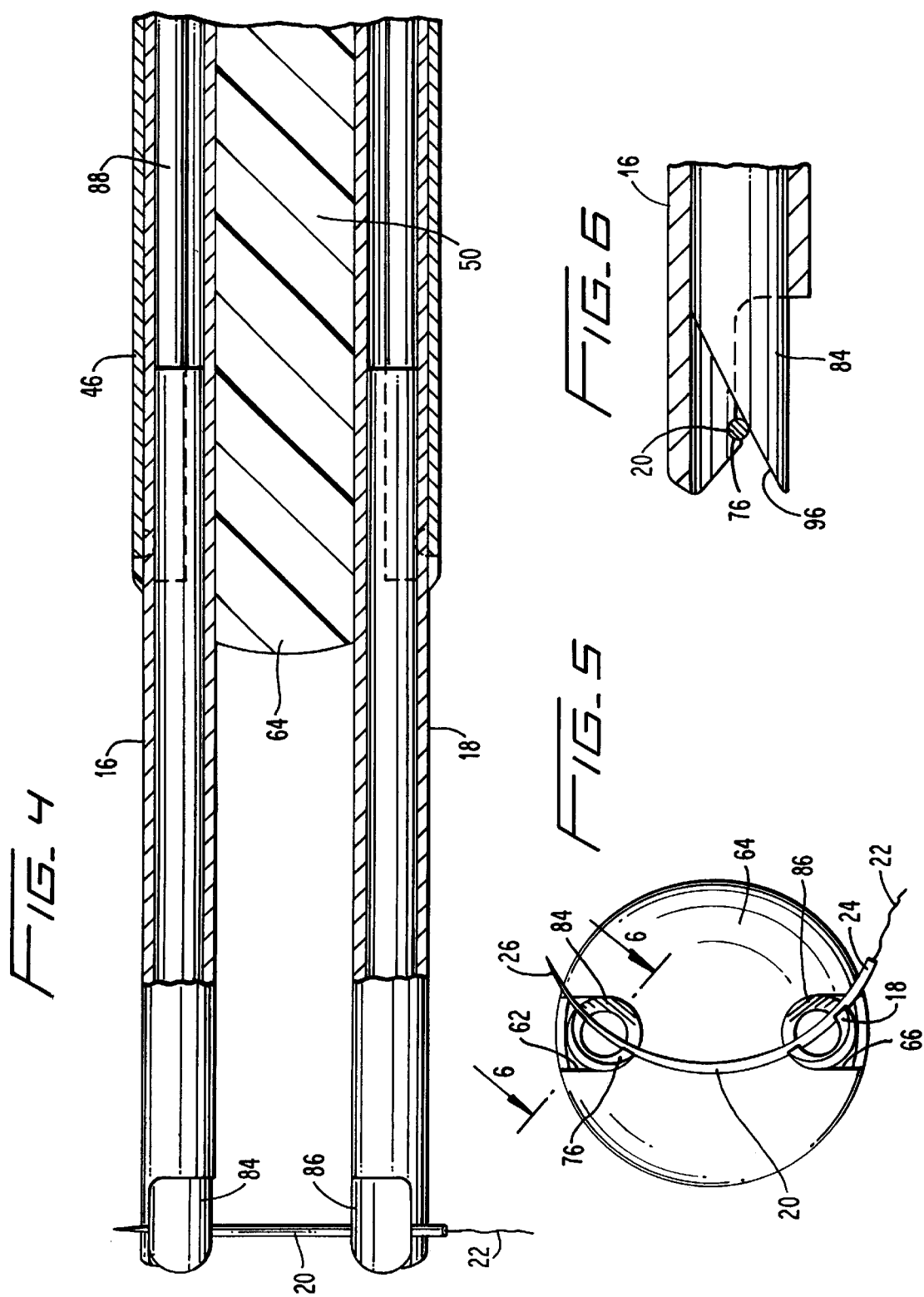

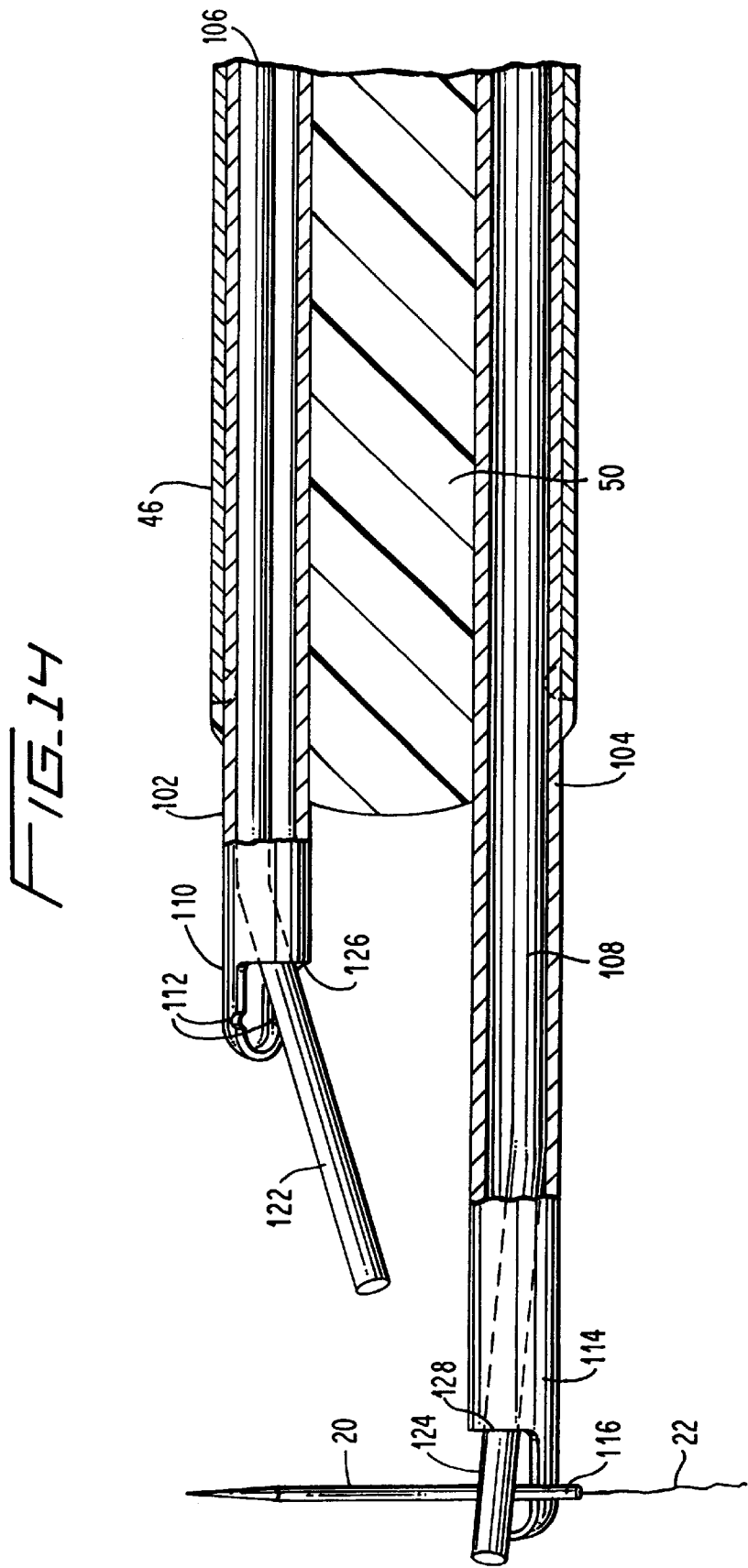

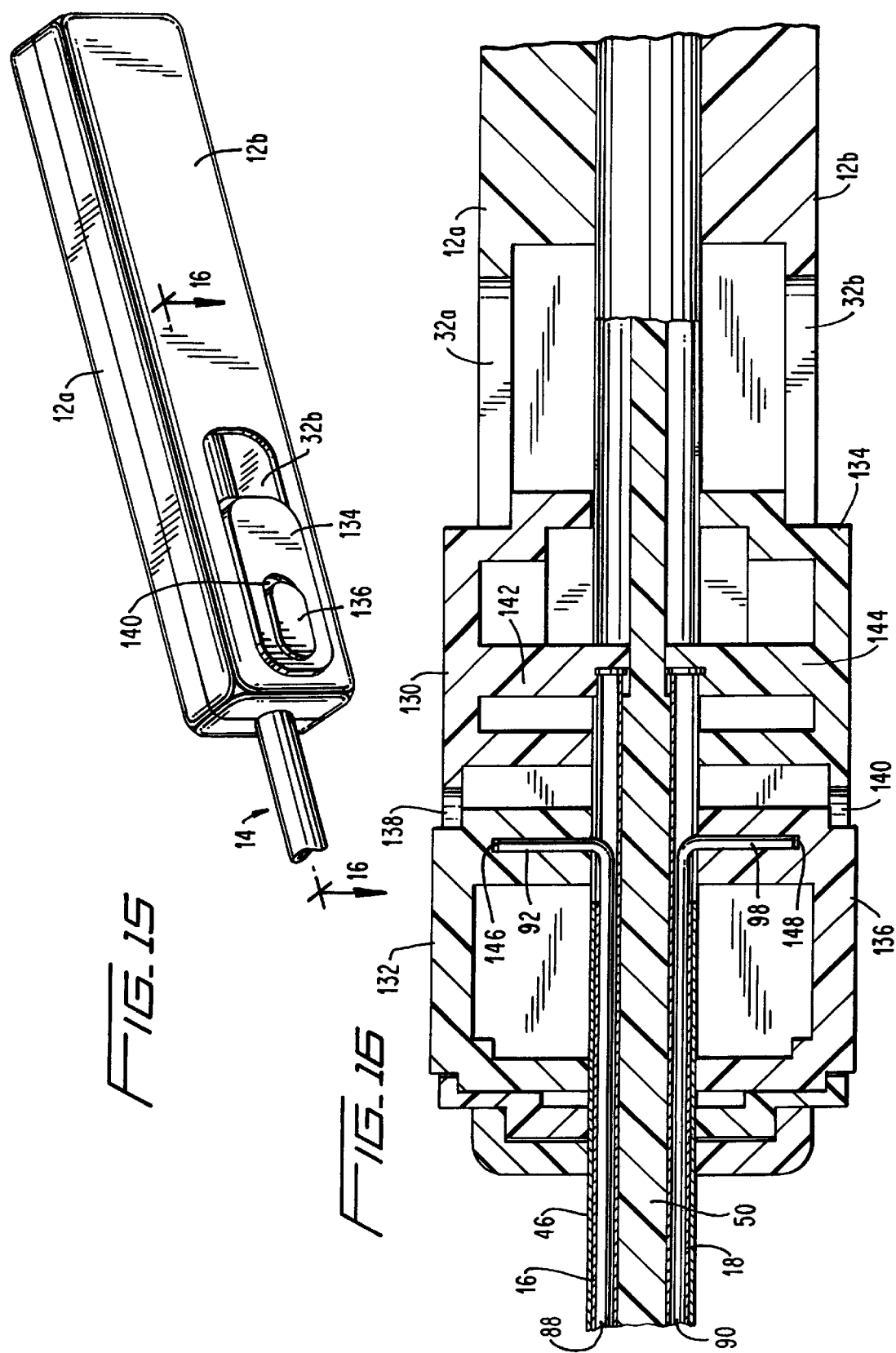

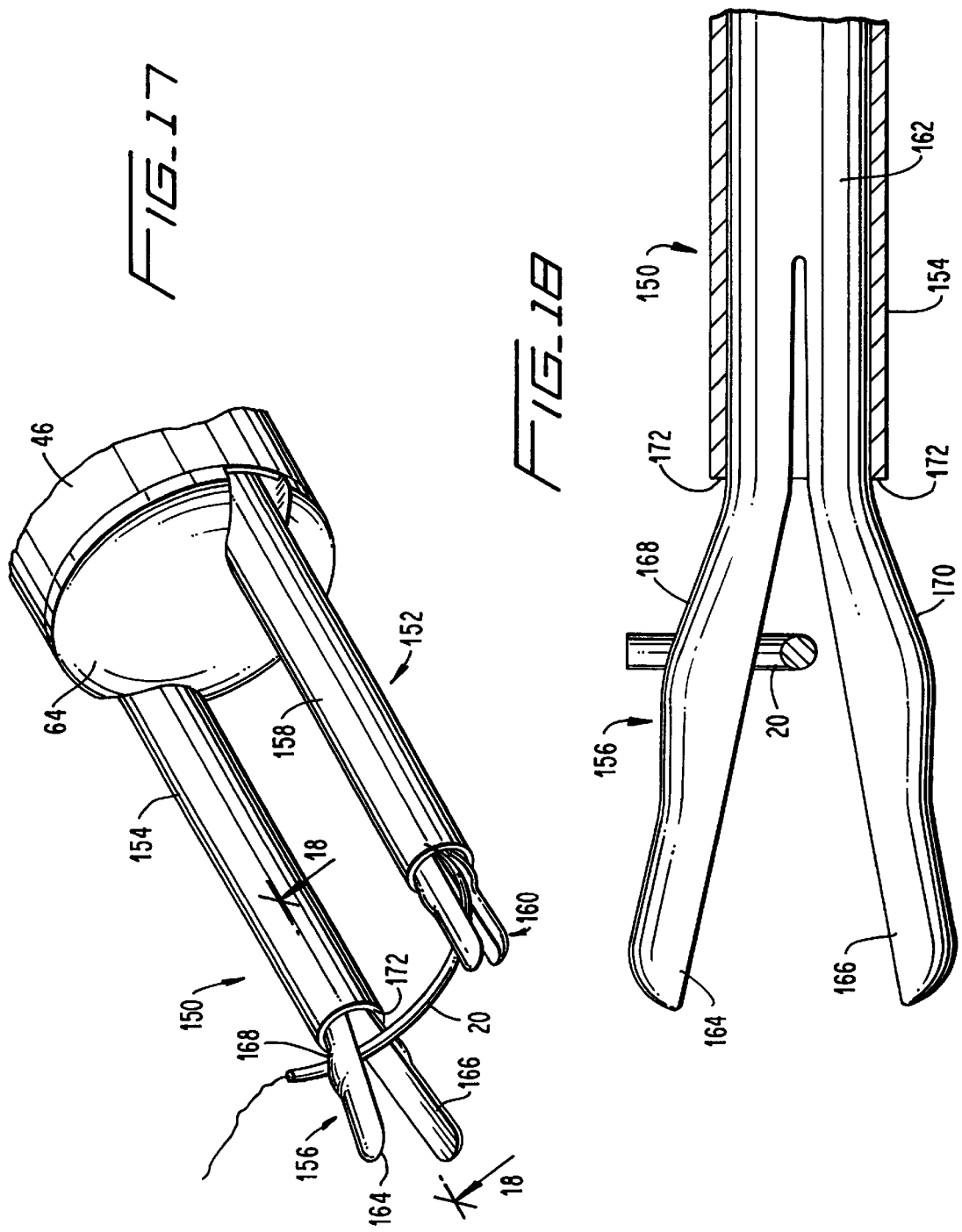

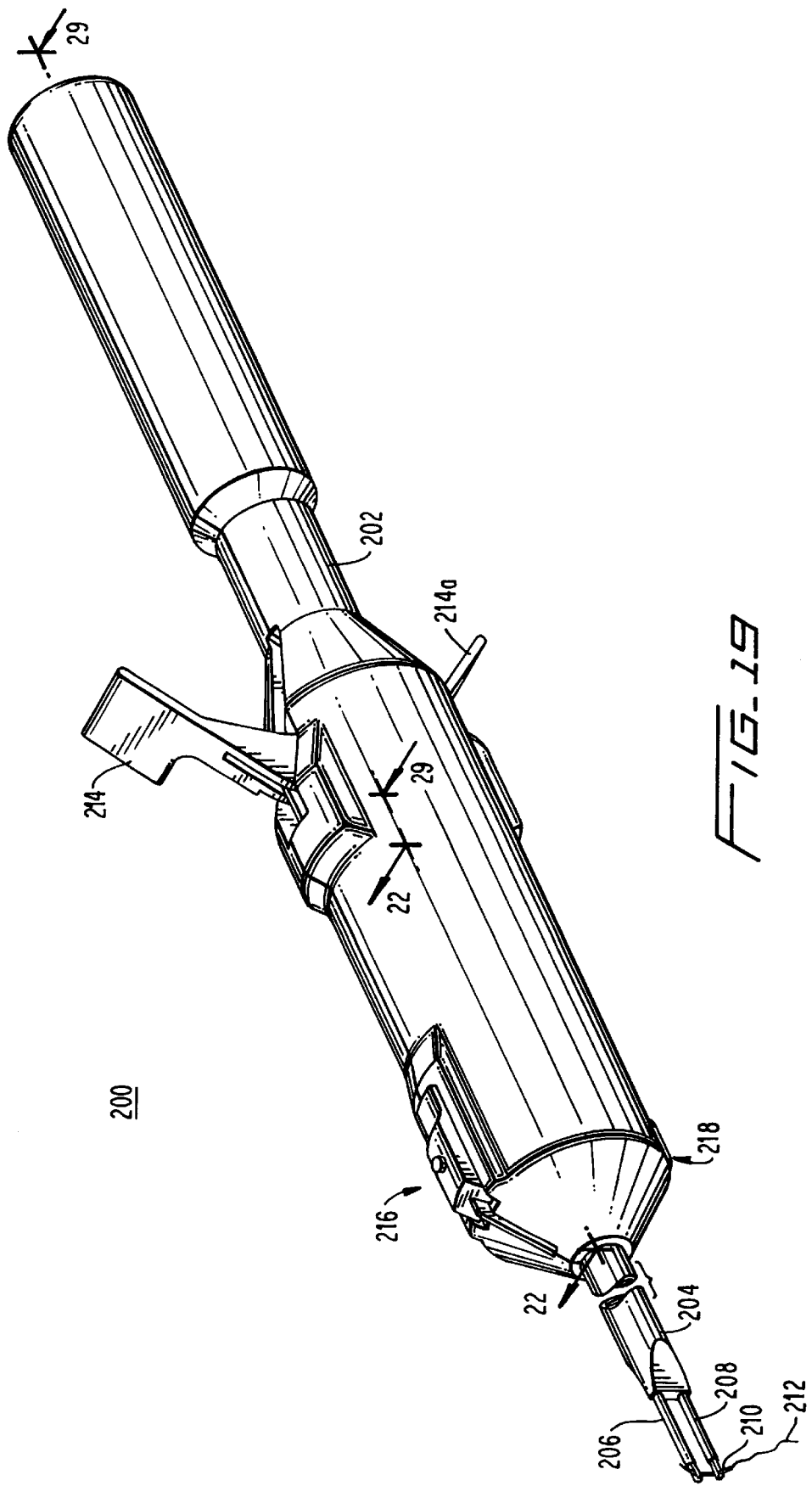

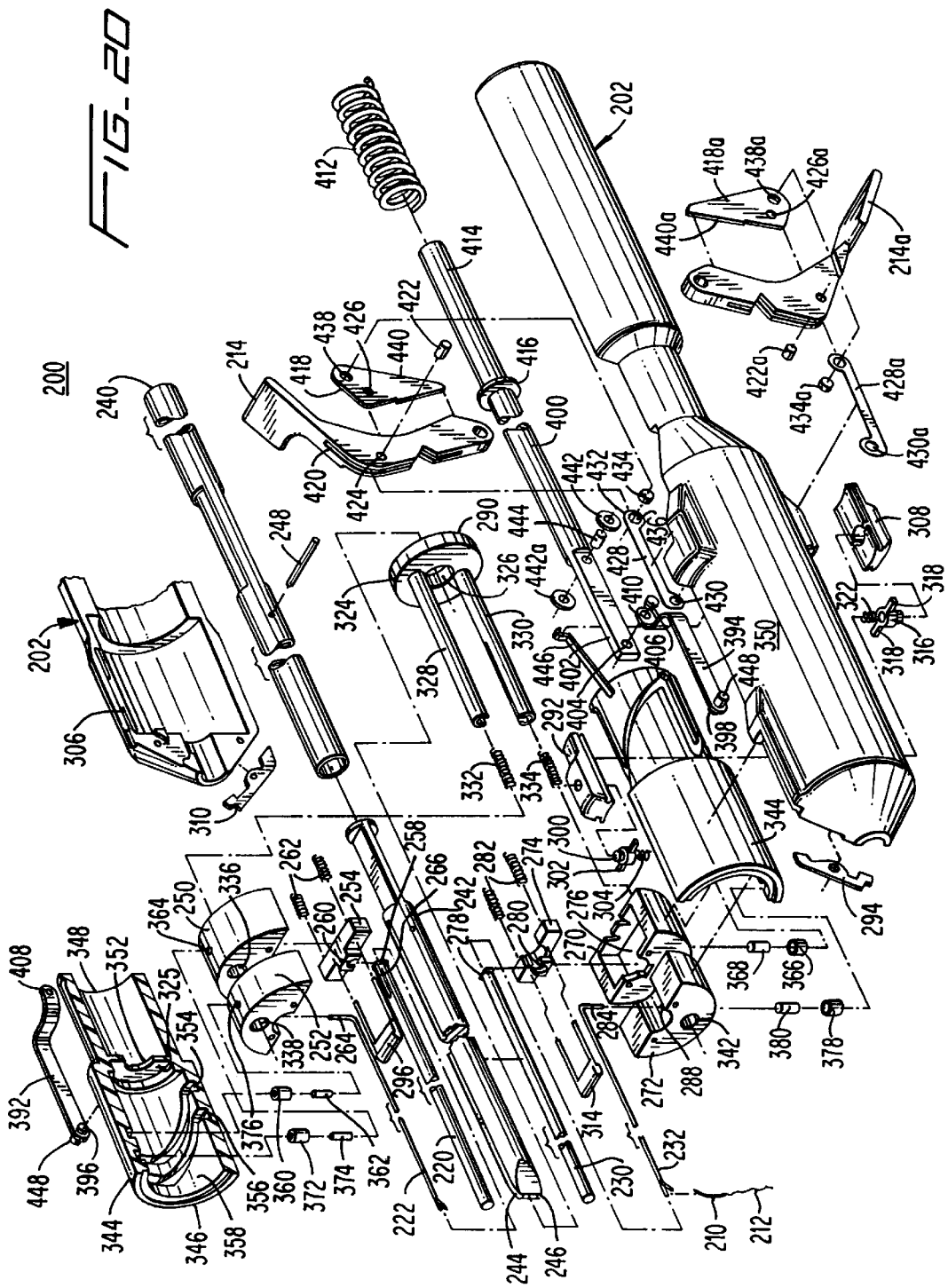

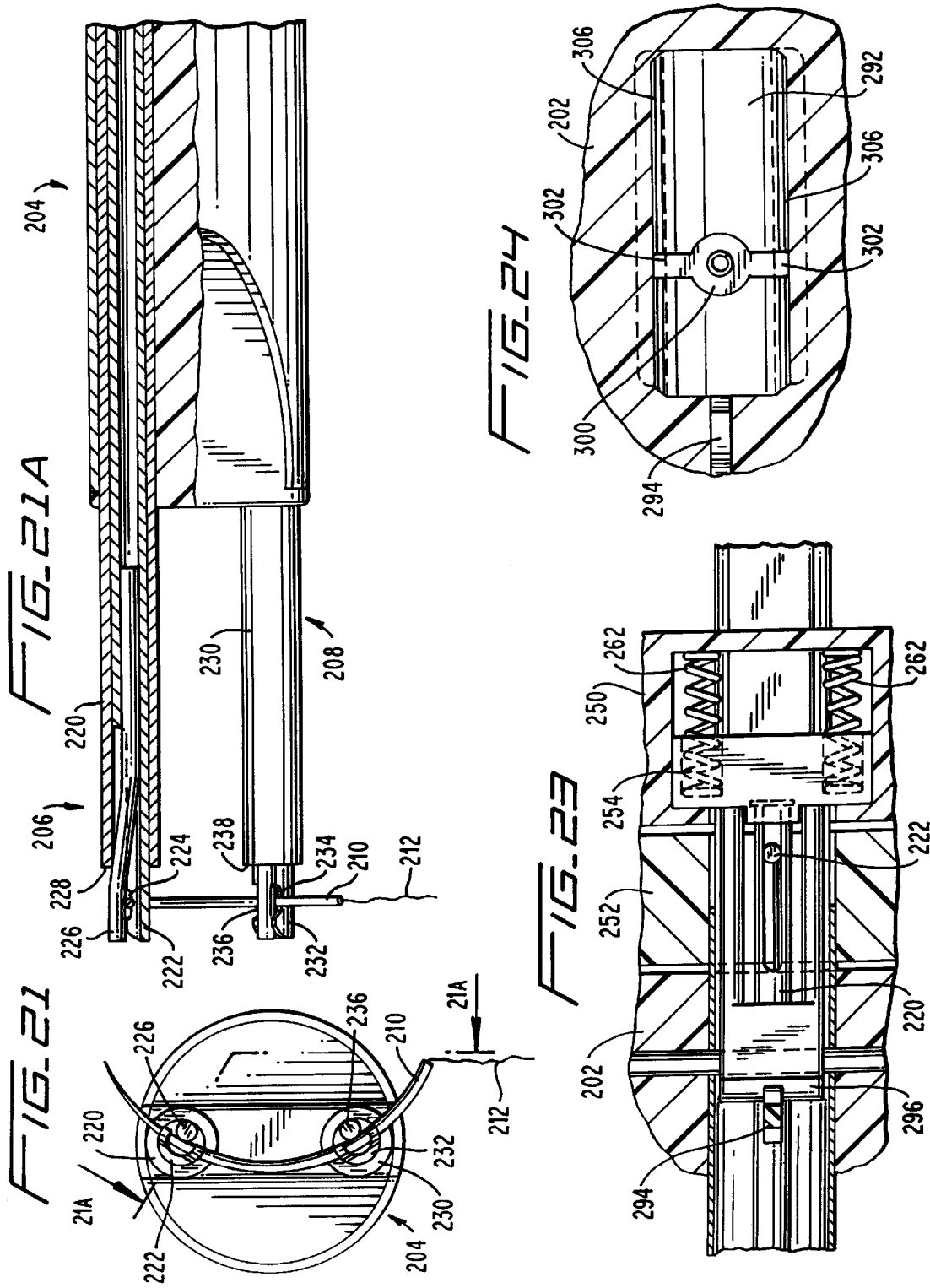

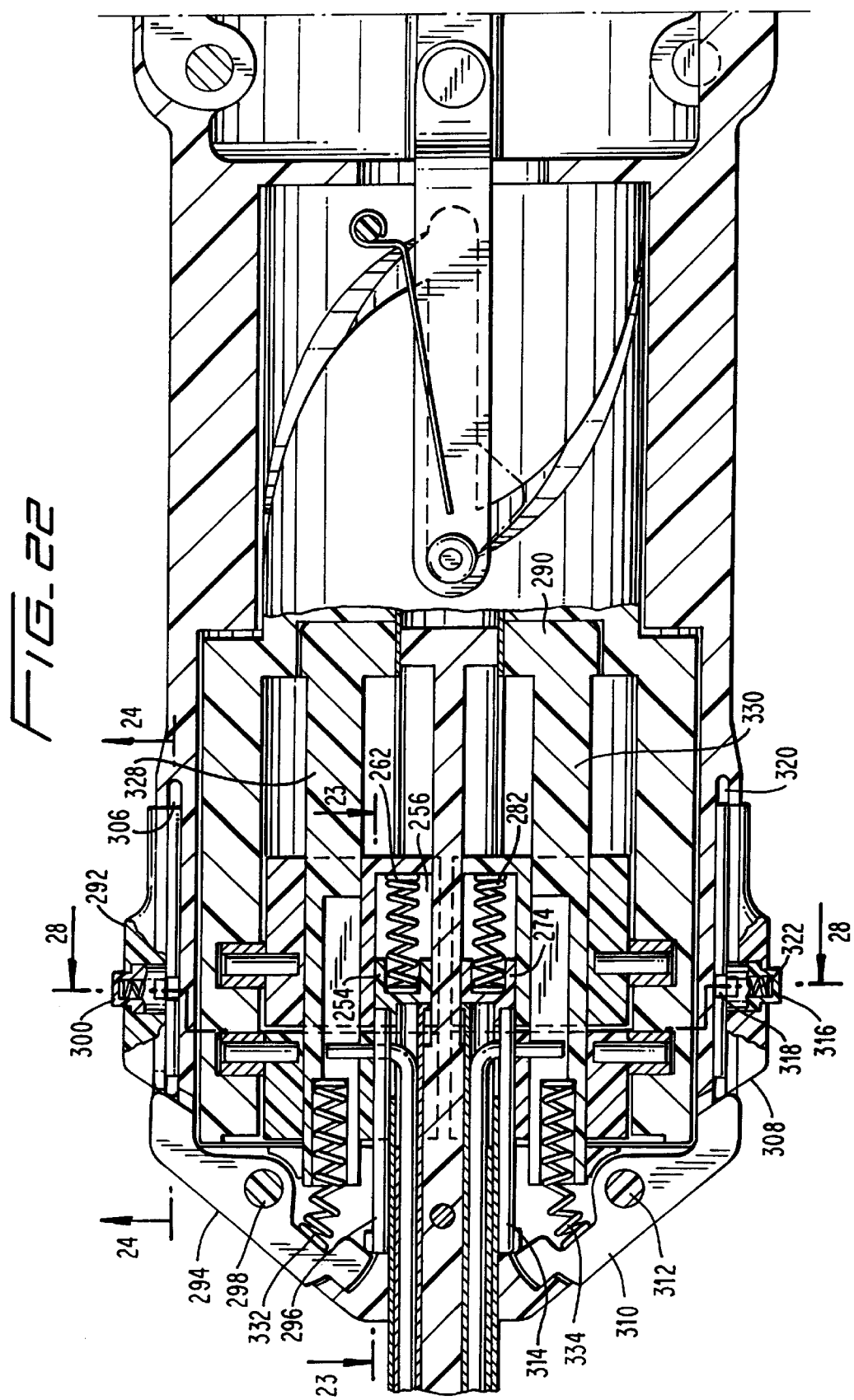

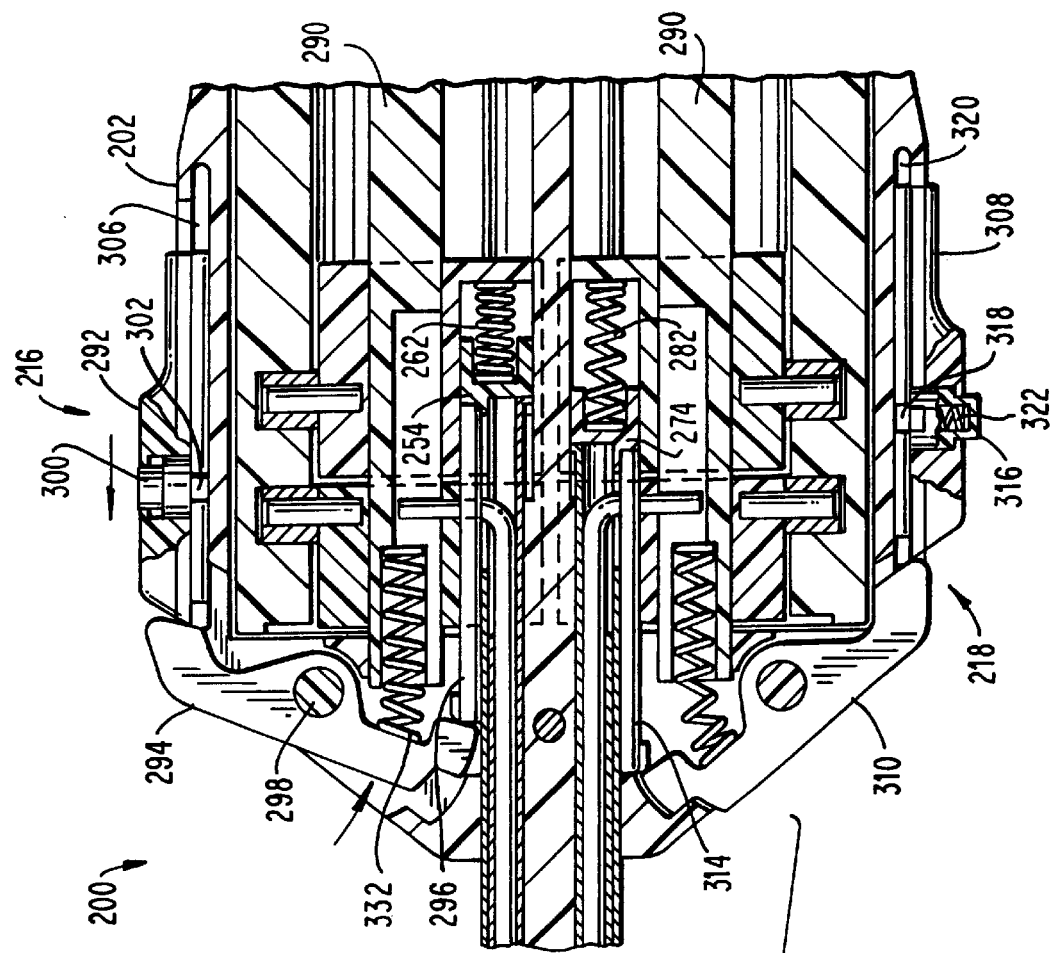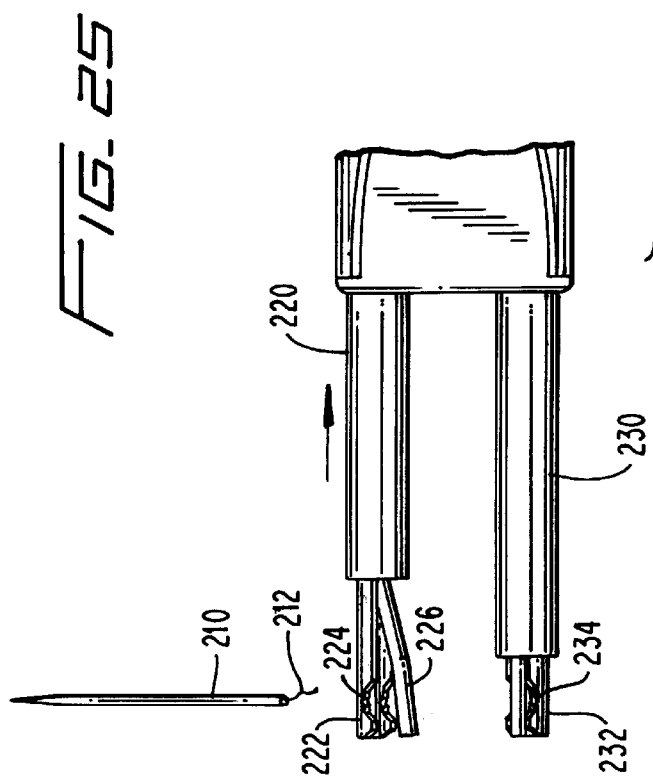

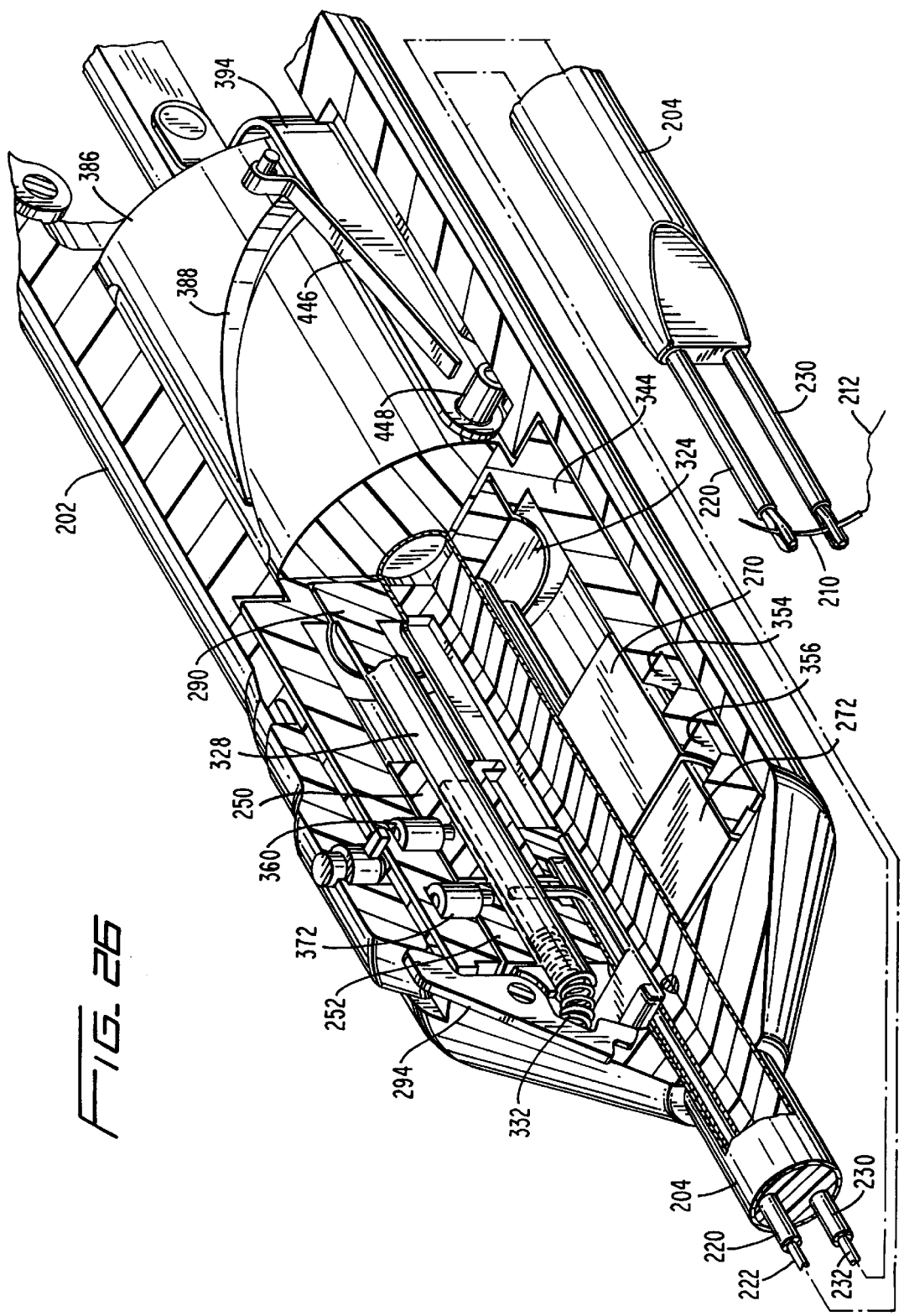

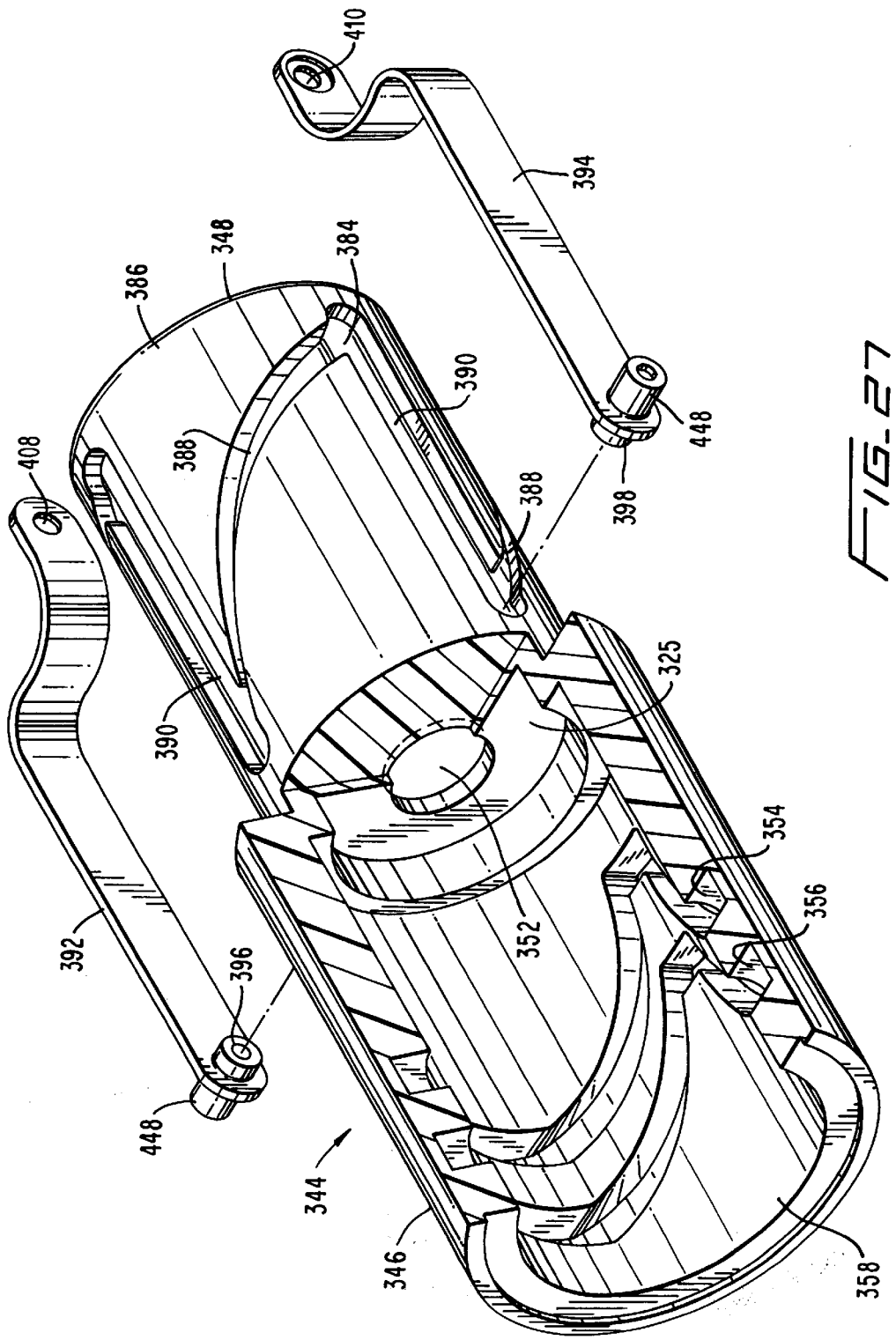

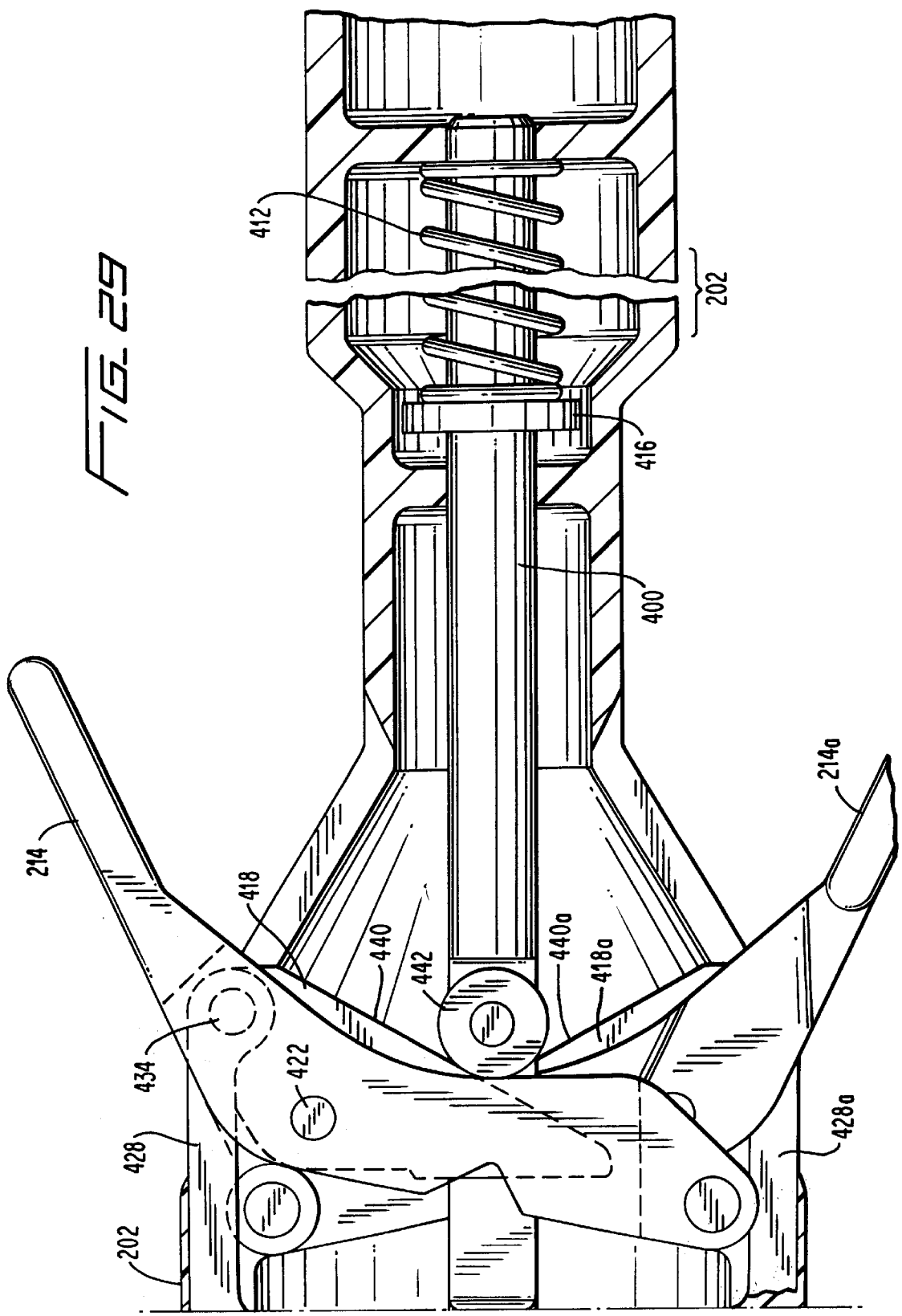

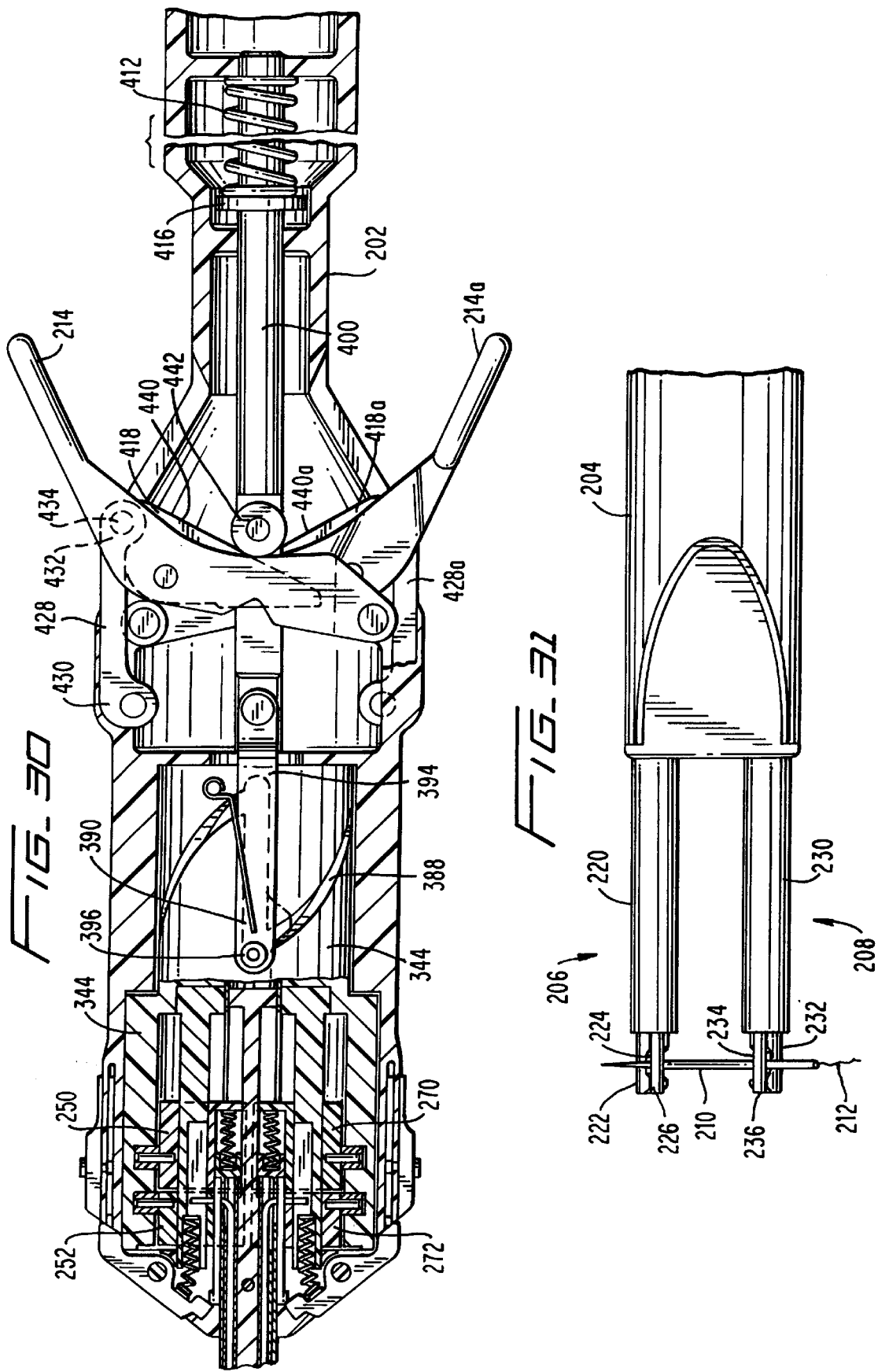

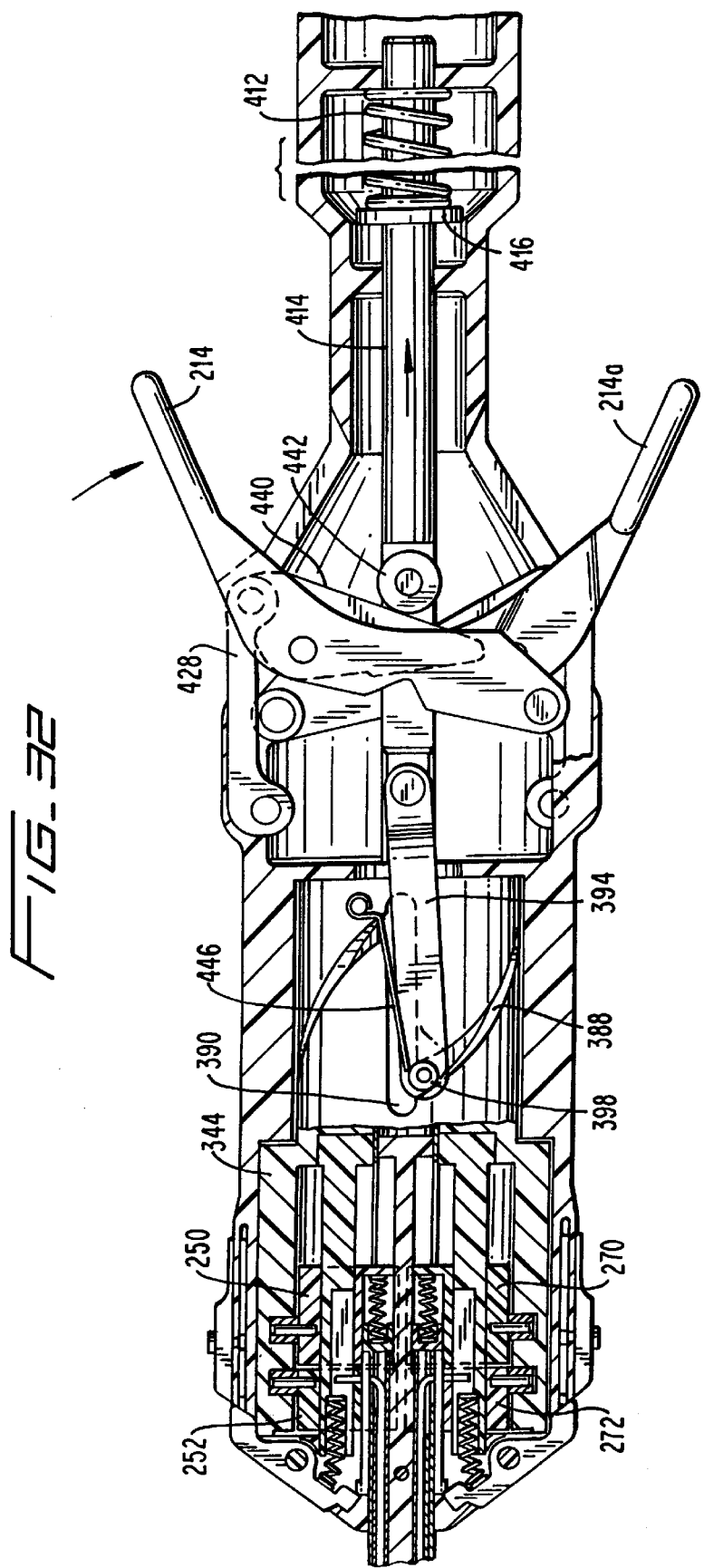

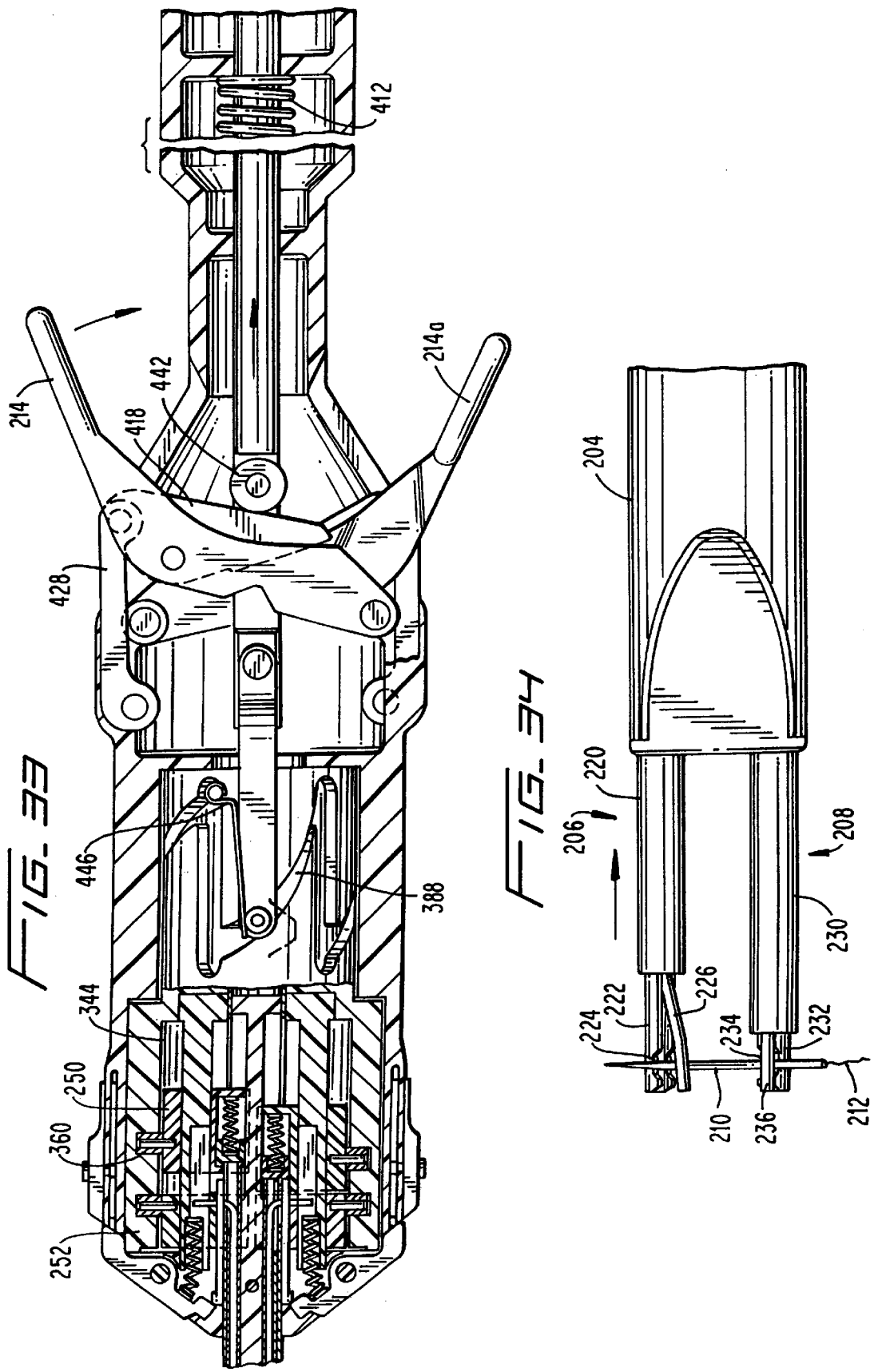

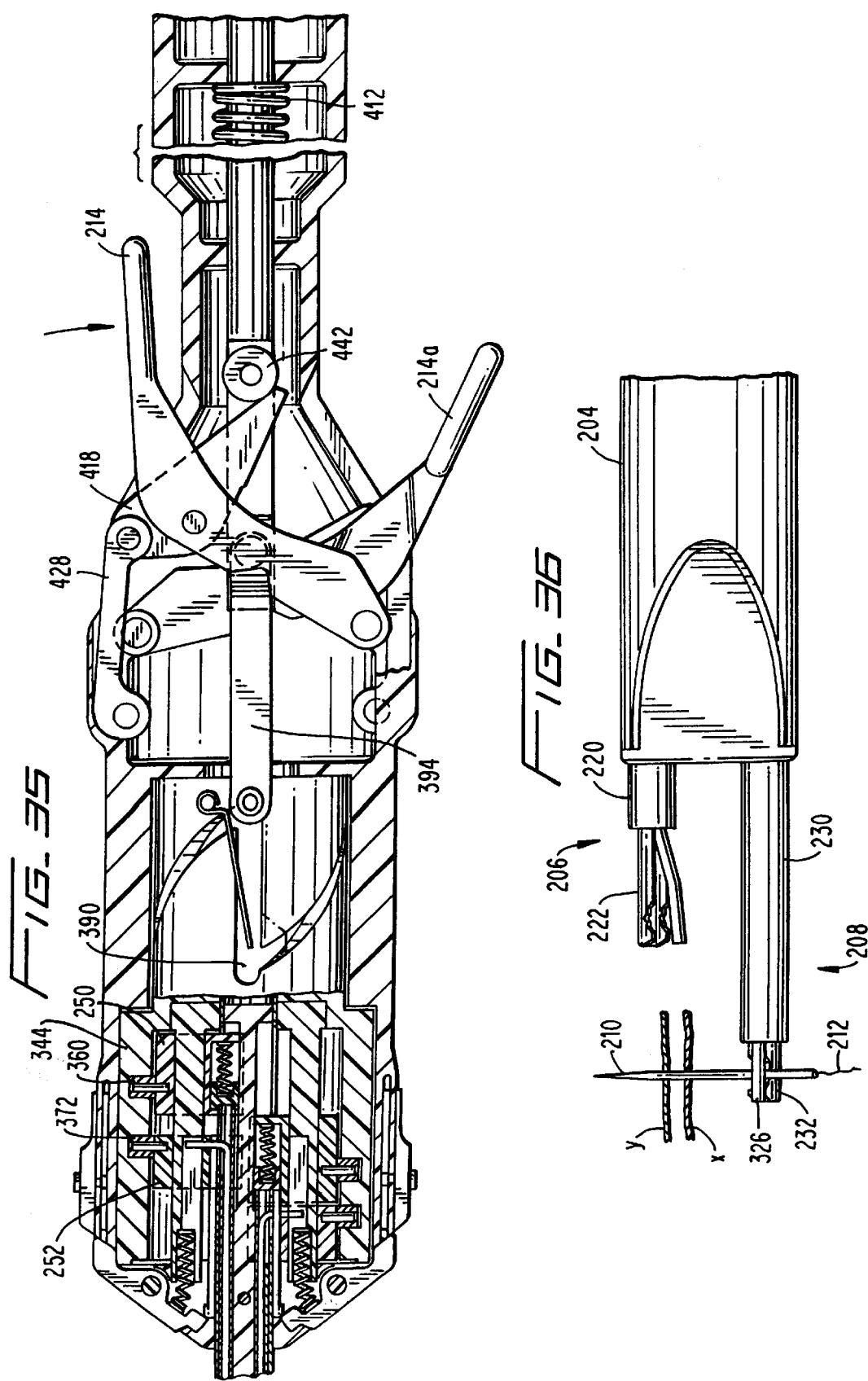

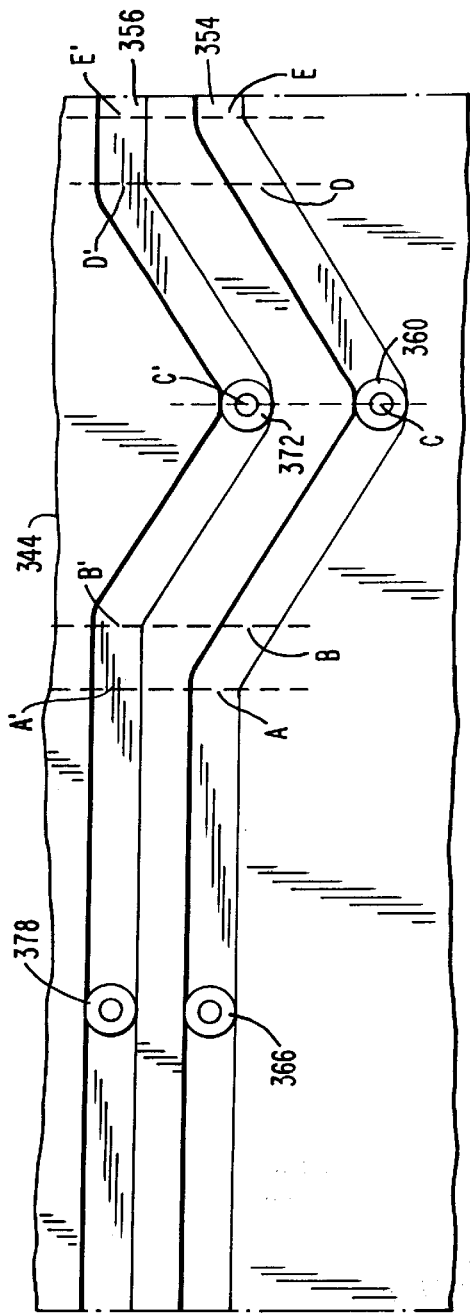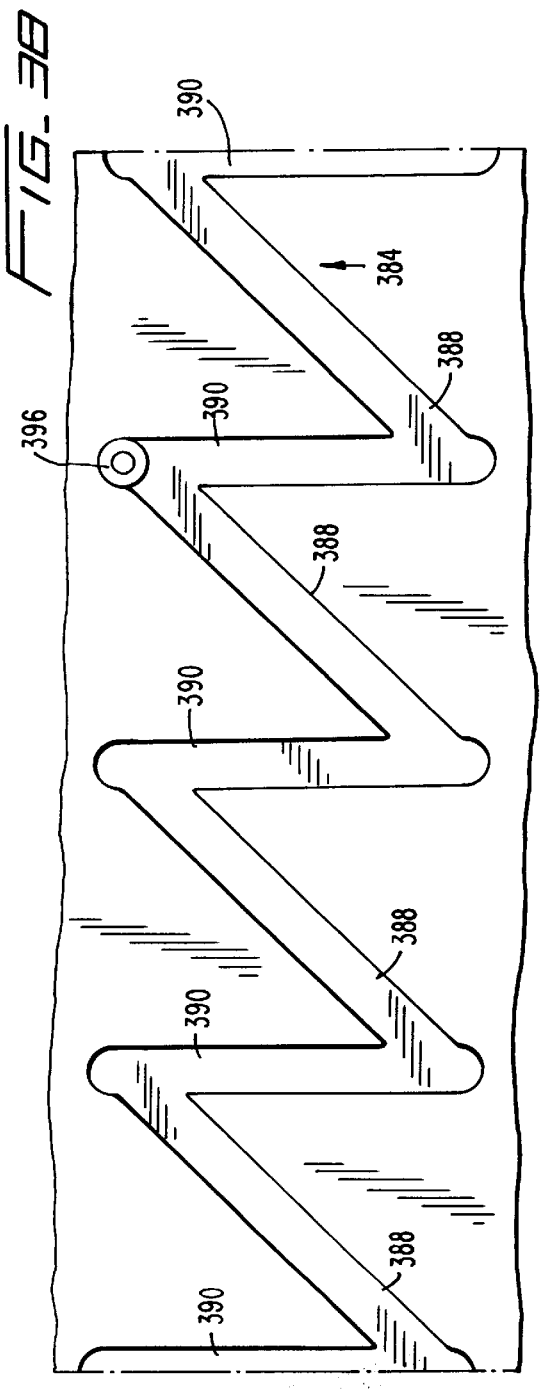

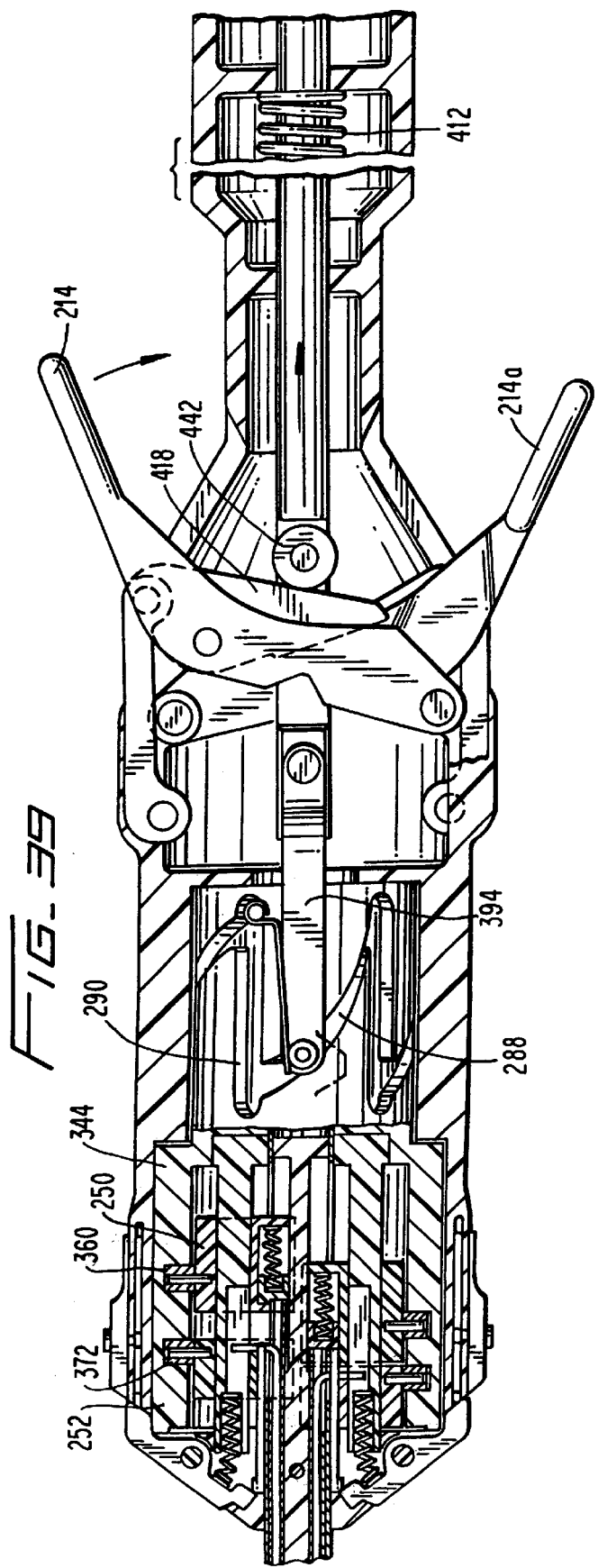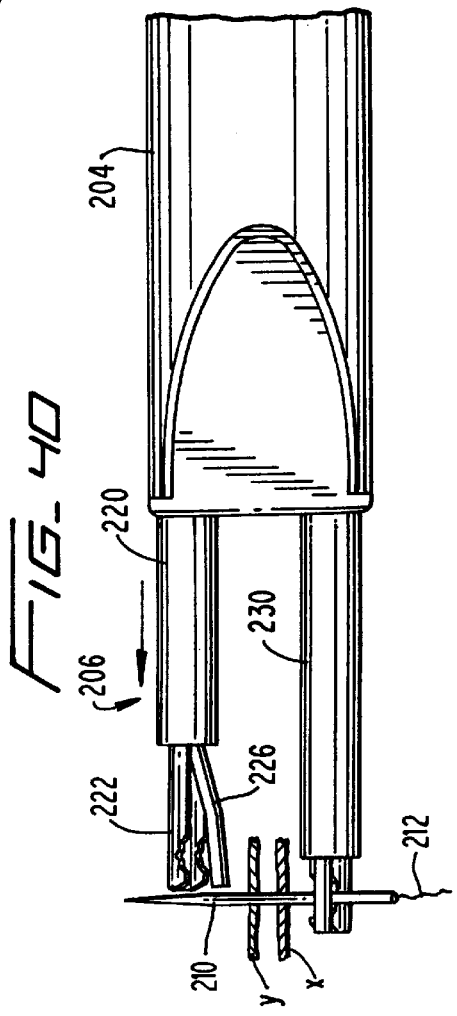

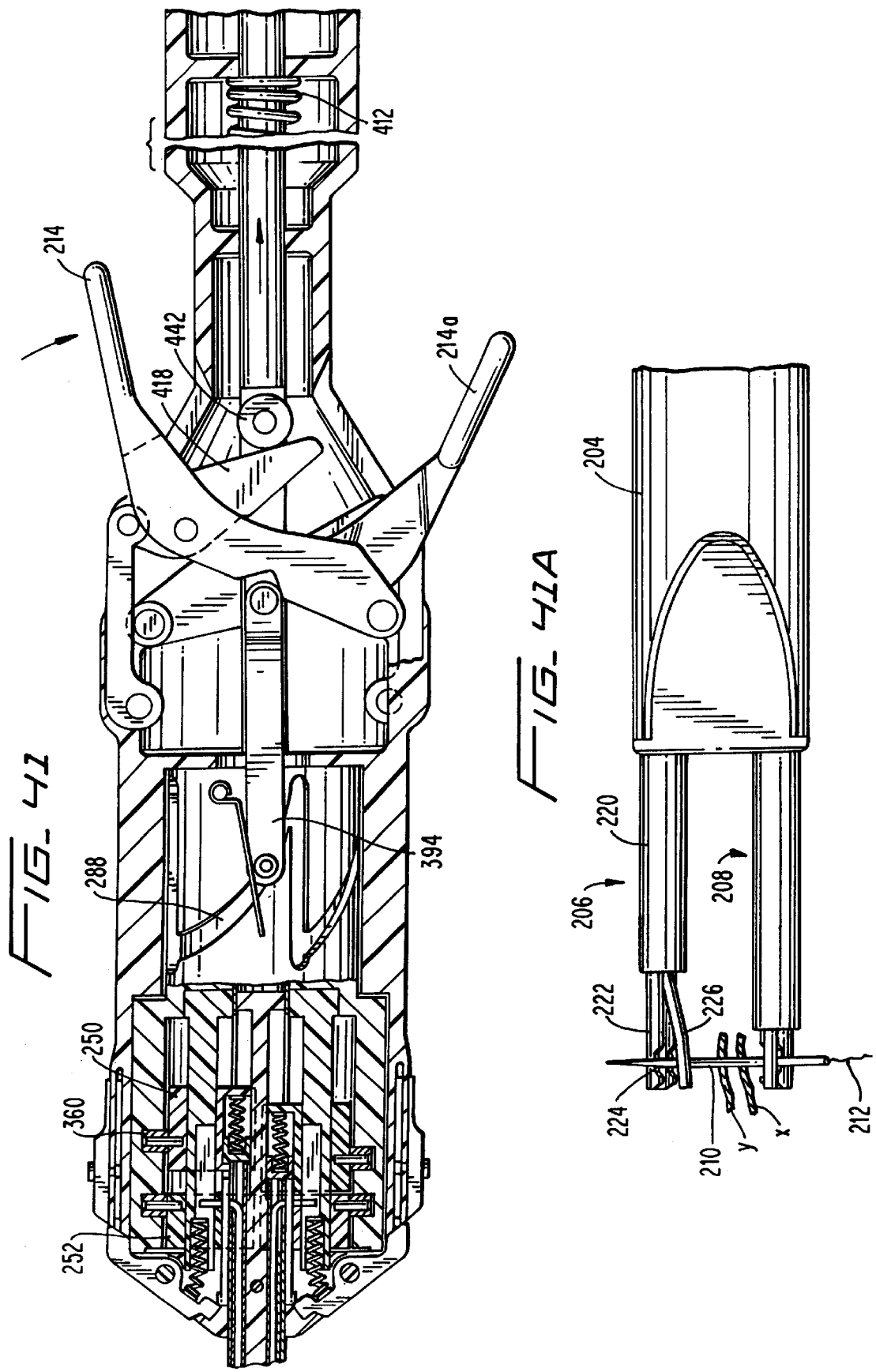

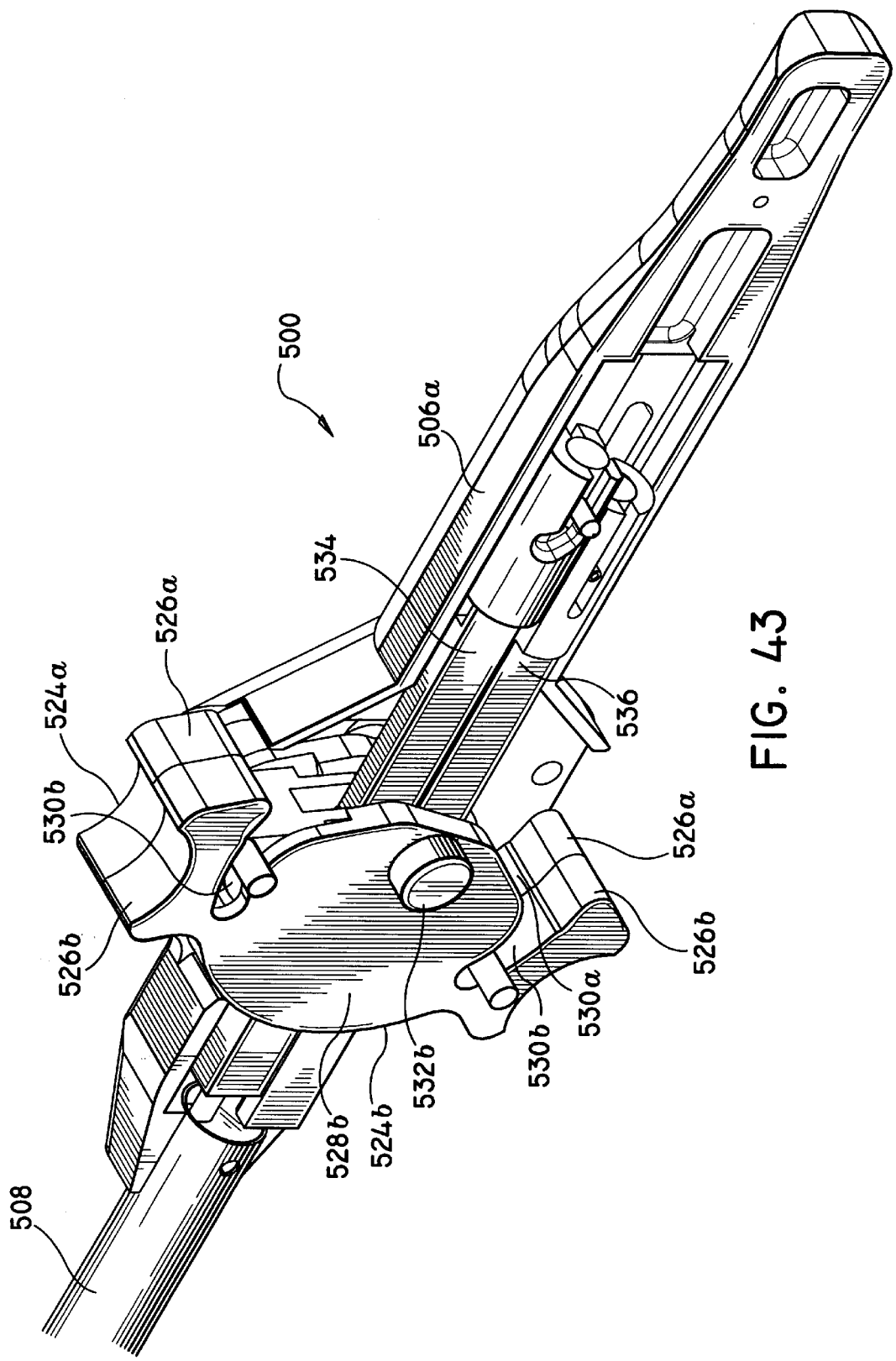

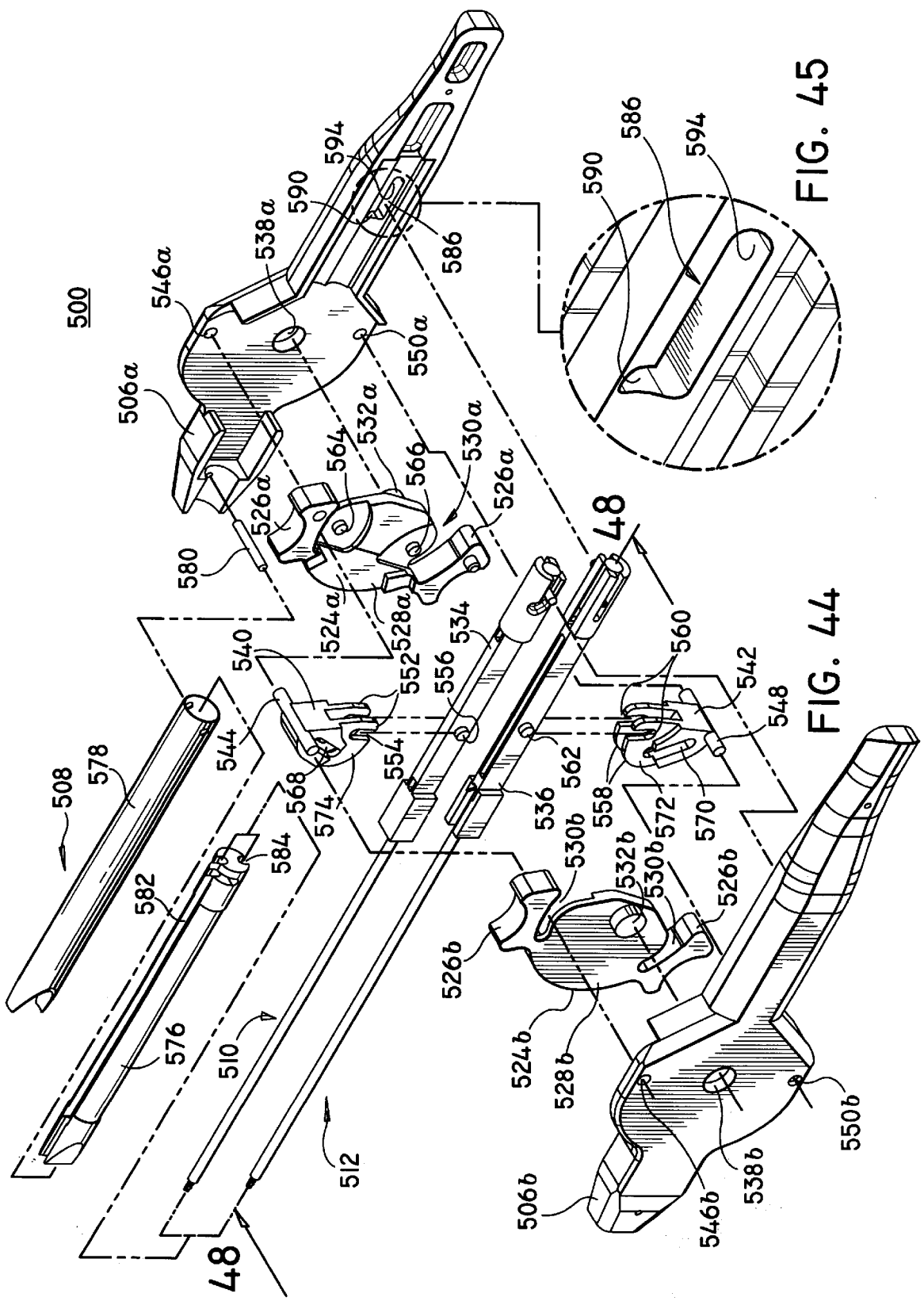

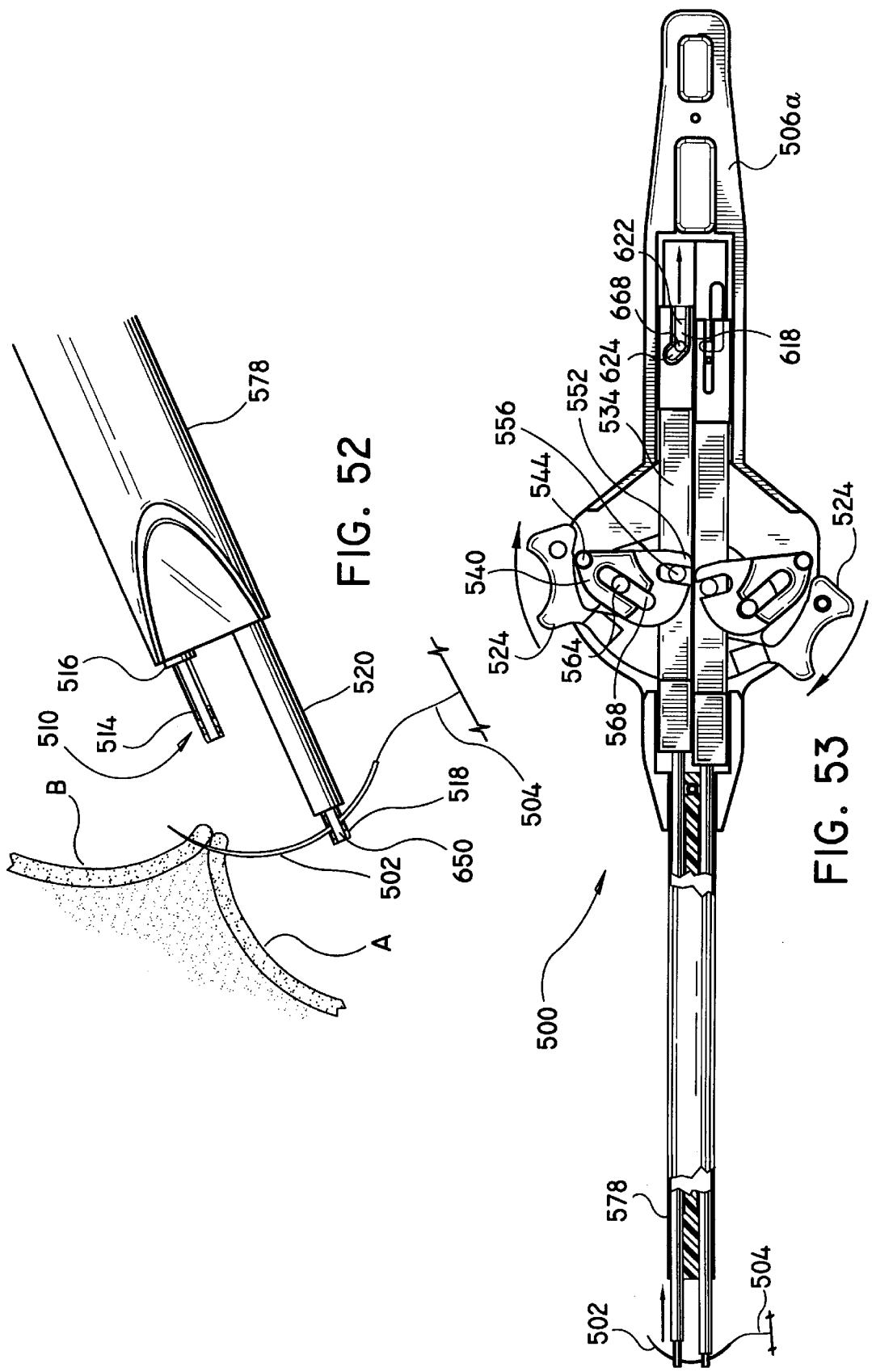

SURGICAL SUTURING APPARATUS

This application is a continuation-in-part of U.S. application Ser. No. 08/662,493 filed on Jun. 13, 1996 U.S. Pat. No. 5,713,531, which is a continuation of U.S. application Ser. No. 08/319,840 filed Oct. 7, 1994 now ABN, the contents of which are incorporated herein by reference.

BACKGROUND

1. Technical Field

The present disclosure relates to surgical apparatus for suturing body tissue and more particularly to surgical suturing apparatus which passes a needle between its jaws.

2. Background of Related Art

During minimally invasive (endoscopic) surgical procedures, suturing of body tissue can be time consuming for the surgeon. In such endoscopic procedures, where surgery is performed in a body cavity and access to the site is through trocar cannulas, suturing is especially difficult. The surgeon cannot grasp the needle as in open surgery, but must rely on grasping instruments to grasp and maneuver the needle in the remote surgical site. These instruments entail grasping the surgical needle between the instrument jaws and manipulating the needle through the body tissue. Oftentimes, a second grasping instrument is required to enable passing the needle between the two instruments in the same manner the surgeon passes the needle during open procedures. Not only is maneuverability difficult, but the needle could slip from the jaws into the body cavity.

To this end, the instrument disclosed in EPO application 92308849.6 was developed. This instrument advantageously provides the surgeon with unprecedented control during suturing in endoscopic procedures. The surgical needle is passed between the jaws of the instrument and is retained in one of the jaws as they are opened. This instrument provides a marked advance over the earlier laparoscopic/endoscopic techniques of suturing. An improvement to the instrument disclosed in EPO Patent Application No. 92308849.6 is disclosed in U.S. patent application Ser. No. 08/134,145, filed Oct. 8, 1993. One of the advantages of this later instrument is that it provides a disposable loading unit which enables the apparatus to be reloaded with a fresh needle and suture.

The advantages attendant passing and retaining a surgical needle between instrument jaws is not limited to endoscopic applications. For example, in open vascular surgery, due to the extremely small size of the surgical needles, it is sometimes difficult for the surgeon to manipulate the needles between his/her hands. Additionally, the surgery is often performed under magnification and the surgeon's repeated steps of focusing on the surgical site to pass the needle through the tissue, focusing away from the surgical site to pass the needle between his hands in preparation for the next stitch, and then re-focusing on the surgical site to continue stitching, is tiring, time consuming and can cause eye strain. The same difficulties of re-focusing and eye strain are encountered if the surgeon uses needle graspers to grasp the needle and pass it through one vessel and then the opposite vessel to thread or impart a series of stitches to the vessels to suture them together.

Because of the extremely small size of the suturing needle used in vascular surgery, typically on the order of ten thousands of an inch in diameter, handling problems may also arise while manipulating the suturing needle through the vascular tissues. For example, upon piercing a vessel, the needle must be pushed through the vessel, released by the needle holder at or e end of the needle and subsequently grasped at the opposite end of the needle to draw the needle and suture through the vessel thus requiring the release of the needle and suture during the procedure. Release of the needle is often undesirable and may pose problems in regaining control of the needle. To avoid this, it may become necessary to use two needle holders, one positioned on either side of the vessel, to continually grasp the needle, thereby requiring two hands to perform the operation. Additionally, precise control of the needle is often difficult when using typical needle holders. The small size of the needle also makes it difficult to recover the needle if dropped during the surgical procedures, especially during endoscopic procedures if it is dropped in the body cavity.

These problems become magnified when the vascular surgical procedures are carried out endoscopically or laparoscopically. While providing illumination and vision, endoscopes typically have a restricted or reduced field of view. Thus, during a suturing operation, as the needle and suture material are passed through the vessels and pulled to draw the suture material through, it often becomes necessary to move the needle holder suturing apparatus from the field of view and may present problems in repositioning the needle within the restricted field of view to form another stitch in the vascular tissues. This increases the time required to suture the vessels together. Additionally, there is a limited space for maneuverability inside the body cavity and limited access to the body tissue, thus making endoscopic suturing quite difficult. The aforementioned minute size of the vessels and vascular surgical needles also add to the difficulty of endoscopic vascular suturing.

Thus, it would be advantageous to have a vascular surgical suturing apparatus for suturing vessels, and particularly suited to suturing vascular tissues endoscopically or laparoscopically. It would also be advantageous to have a vascular surgical suturing apparatus which is capable of maintaining precise and constant control of the vascular needle as it is passed from one needle holding jaw of the apparatus to another to avoid release of the needle during the suturing operation. It would be further advantageous to have a vascular surgical suturing apparatus which is capable of suturing vascular tissue sections together with limited apparatus and needle movement in order to maintain the entire suturing operation within a restricted field of view. An instrument which passes the needle between the jaws would overcome the difficulties by allowing the surgeon to continuously focus on the surgical site during the entire vessel stitching procedure. It would be particularly advantageous to provide a suturing apparatus having jaw structures movable longitudinally with respect to a body portion. It would also be advantageous to provide a suturing apparatus which could accommodate current curved vascular needles without requiring use of a specifically designed needle. It would additionally be advantageous to provide a suturing apparatus which transfers a needle between jaws in response to repeated actuation of one or more control levers.

SUMMARY

An apparatus for suturing body tissue is disclosed comprising a handle portion, a needle engaging body portion extending from the handle portion and defining a longitudinal axis, first and second jaws extending from the body portion, and a first securing member or locking blade cooperating with the first jaw and a second securing member or locking blade cooperating with the second jaw. A jaw actuating mechanism moves at least one of the jaws longitudinally and a needle securing mechanism is operatively connected to the first and second securing members for moving at least one of the securing members between a first position to secure a surgical needle within one of the jaws and a second position to release the needle from the jaw.

In one preferred embodiment, the jaw actuating mechanism comprises a first button slidably mounted with respect to the handle portion for moving the first jaw and a second button slidably mounted with respect to the handle portion for moving the second jaw. The needle securing mechanism preferably comprises first and second control levers pivotably mounted with respect to the handle portion. Each of the jaw members has a needle receiving notch formed therein such that each of the securing members is slidable to frictionally retain the needle in the notch of the jaw member.

In another embodiment, alternative jaw structure is provided with flexible distal portions or needle securing members which, when advanced or retracted, are cammed by an edge of the jaw structure to secure the surgical needle within the jaw.

In another alternative embodiment, the jaw actuating mechanism may utilize needle control levers which are slidably mounted within the jaw actuating mechanism as opposed to pivotally mounted as indicated in previous embodiments.

A further alternative jaw structure is provided having a pair of biased apart arms which may be cammed together by advancement of a sleeve to secure needles therebetween.

In a further embodiment, jaw structure is provided which, as with the embodiments indicated above, moves each jaw individually and longitudinally with respect to the opposing jaw and with respect to the body portion. Additionally, needle securing structure is provided which also moves longitudinally with respect to its associated jaw and with respect to the body portion. In this embodiment, a camming mechanism is provided which moves each jaw through four distinct motions or cycles. In a first motion, a sleeve is retracted to release the surgical needle from the jaw and in a second motion the jaw and sleeve are retracted away from the needle so the needle may be used in suturing tissue. In a third motion, the jaw is again advanced about the surgical needle and in a fourth motion the sleeve is advanced to again cam or grasp the surgical needle within the jaw. A subsequent four motions or cycles can be performed to create similar motions with an opposing jaw.

The release of the surgical needle and retraction of the jaw is accomplished with a single depression of a control lever. Similarly, the advancement of the jaw and grasping of the surgical needle is also accomplished with a single depression of a control lever. Thus, in order to completely form a stitch using the disclosed embodiment, the control lever must be depressed four times, two times for each jaw. The single depression of the control lever rotates a camming sleeve one quarter turn. Each quarter turn of the camming sleeve releases and retracts or advances and grasps the surgical needle per jaw.

In this particular embodiment, loading structure may be provided which overrides the actuation of the control levers and allows loading of a surgical needle within the jaw structure.

In an additional embodiment, control structure is provided which initially advances a jaw assembly toward a surgical needle and subsequently grasps the surgical needle within the jaw assembly in response to rotation of a trigger of the control structure. Rotation of the trigger from a central position in a first direction actuates a first jaw assembly while rotation of the trigger from the central position in a second direction actuates a second jaw assembly. Both first and second jaw assemblies move longitudinally with respect to a tubular portion and with respect to each other. Additionally, needle securing structure associated with the jaw assemblies also move longitudinally within the jaw assemblies and with respect to the tubular portion. In this embodiment, loading structure may be provided to override the control structure and allow loading of a surgical needle.

An important advantage of the present apparatus is the ability to mechanically reproduce the natural suturing motion of the surgeon while maintaining mechanical control over the needle at all times.

BRIEF DESCRIPTION OF THE DRAWINGS

Various embodiments of the surgical apparatus of the subject application will be described below with reference to the following drawings wherein:

FIG. 1 is a perspective view of the surgical suturing apparatus of the present application;

FIG. 2 is an exploded perspective view of the surgical apparatus of FIG. 1;

FIG. 3 is a cross-sectional view taken along lines 3—3 of FIG. 1 showing the jaw actuating mechanisms and the needle securing mechanisms in their initial position;

FIG. 4 is an enlarged cross-sectional view corresponding to the position of the jaw actuating and needle securing mechanisms of FIG. 3 showing the needle retained in both jaws;

FIG. 5 is an enlarged end view of the surgical apparatus showing the needle retained in both jaws;

FIG. 6 is an enlarged cross-sectional view taken along lines 6—6 of FIG. 5 showing the needle retained in the upper jaw;

FIG. 14 is an enlarged cross-sectional view showing the upper jaw in the retracted position and the needle retained in the lower jaw;

FIG. 15 is a perspective view of an alternate embodiment of the actuating mechanism of the surgical suturing apparatus;

FIG. 16 is an enlarged cross-sectional view taken along lines 16—16 of FIG. 15;

FIG. 17 is a perspective view of another alternate embodiment of the apparatus having two pairs of jaws;

FIG. 18 is a cross-sectional view taken along lines 18—18 of FIG. 17 illustrating the jaws in the open position;

FIG. 19 is a perspective view of yet another alternate embodiment of a surgical suturing apparatus;

FIG. 20 is a perspective view, with parts separated, of the embodiment of FIG. 19;

FIG. 21 is an enlarged end view of the embodiment of FIG. 19;

FIG. 21A is a view taken along the line 21A—21A of FIG. 21;

FIG. 22 is a view, partially shown in section, taken along line 22—22 of FIG. 19;

FIG. 23 is a partial sectional view of a portion of the needle clamping mechanism taken along line 23—23 of FIG. 22;

FIG. 24 is a sectional view of a portion of a needle loading mechanism taken along line 24—24 of FIG. 22;

FIG. 25 is a view, partially shown in section, illustrating the operation of the needle loading mechanism;

FIG. 26 is an enlarged perspective view, partially shown in section, of a distal portion of the embodiment of FIG. 19;

FIG. 27 is a perspective view, partially shown in section, of a camming sleeve;

FIG. 29 is a view, partially shown in section, taken along line 29—29 of FIG. 19;

FIG. 30 is a sectional view of the handle portion of the embodiment of FIG. 19 in an initial position;

FIG. 31 is a perspective view of the endoscopic portion of the embodiment of FIG. 19 corresponding to the position of FIG. 30 showing the needle retained in both jaws;

FIG. 32 is a view similar to FIG. 30 illustrating initial activation of the handle mechanism;

FIG. 33 is a view similar to FIG. 32 illustrating further actuation;

FIG. 34 is a view similar to FIG. 31 corresponding to the position of FIG. 33 and illustrating release of the needle from one of the jaws;

FIG. 35 is a view similar to FIG. 33 illustrating further actuation to complete a first cycle of the handle mechanism;

FIG. 36 is a view similar to FIG. 36, corresponding to the position of FIG. 35 and illustrating retraction of the jaw;

FIG. 37 is a view of the camming grooves illustrating the timing of the movement of the cam rollers within the grooves;

FIG. 38 is a view of the drive grooves of the handle mechanism corresponding to the position of FIG. 37;

FIG. 39 is a view similar to FIG. 35 illustrating the initiation of a second cycle;

FIG. 40 is a view similar to FIG. 36, corresponding to the position of FIG. 39 and illustrating the distal movement of the jaw toward the surgical needle;

FIG. 41 is a view similar to FIG. 39 illustrating a partial second cycle;

FIG. 41A is a view similar to FIG. 40 corresponding to FIG. 41 and illustrating completion of the distal movement of the jaw about the surgical needle;

FIG. 43 is a perspective view, partially shown in section, of a handle portion of the embodiment of FIG. 42;

FIG. 44 is a perspective view of the embodiment of FIG. 42 with parts separated;

FIG. 45 is an enlarged isolation view of a cam slot in the housing half 506a;

FIG. 52 is a perspective view of the distal end of the embodiment of FIG. 42, showing initial insertion of the surgical needle through a pair of tissue sections;

FIG. 53 is a side view, partially shown in section, of the embodiment of FIG. 42 showing actuation to open the first jaw;

DETAILED DESCRIPTION OF THE PREFERRED EMBODIMENTS

Figure 7:
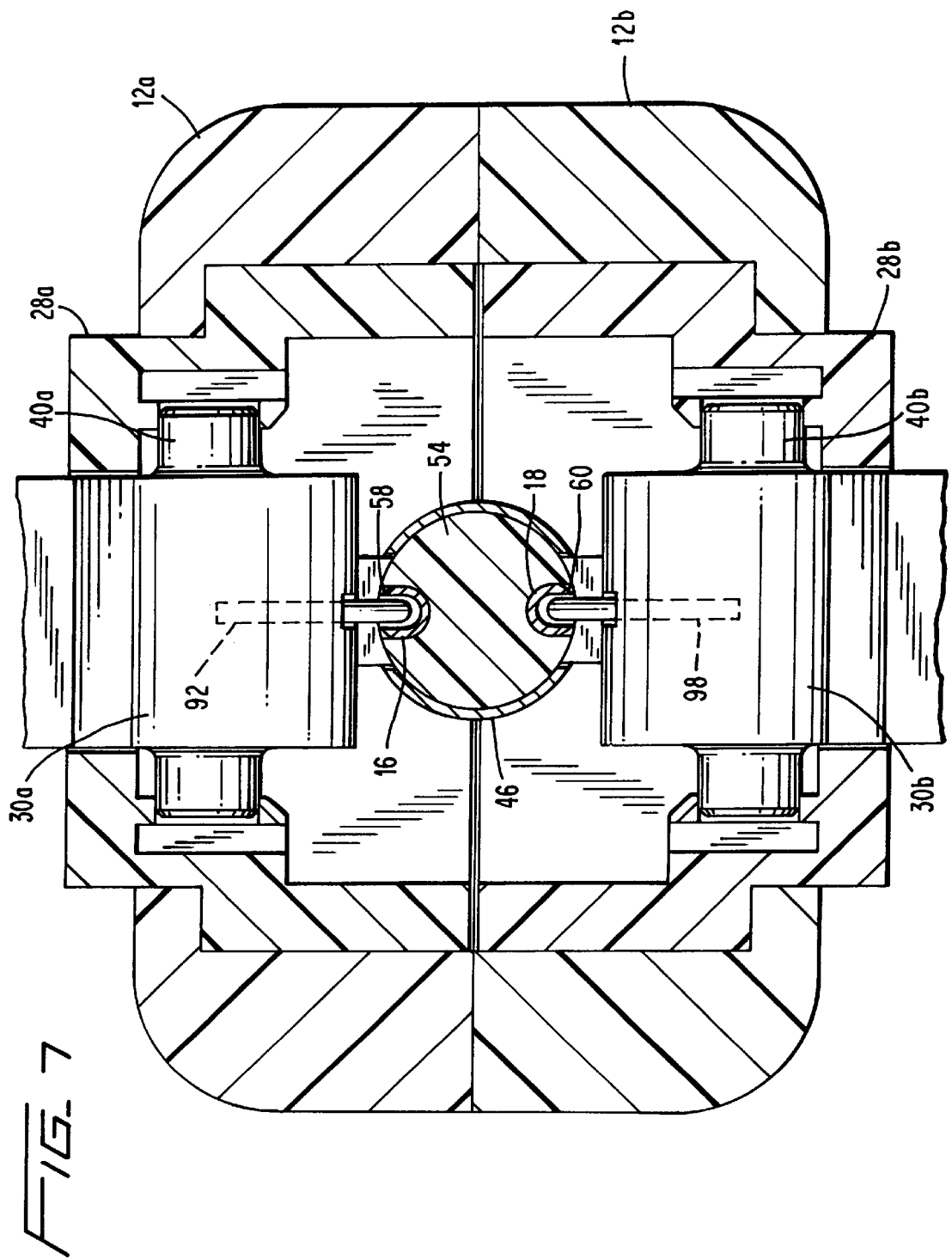
FIG. 7 is an enlarged cross-sectional view taken along lines 7—7 of FIG. 3.

Referring now to the drawings, wherein like reference numerals identify similar or identical elements throughout the several views and in particular FIG. 1, an apparatus disclosed herein is designated generally by reference numeral 10. Apparatus 10 is designed to suture body tissue and includes a handle or housing portion 12, an endoscopic or elongated tubular portion 14 extending distally from housing portion 12, and upper and lower jaws 16, 18, respectively, extending distally from tubular portion 14. Jaws 16 and 18 are provided to releaseably grasp a surgical needle 20. Surgical needle 20 has a suture 22 attached to an end 24 and a pointed end 26 opposite thereof. Each of jaws 14 and 16 are preferably in the form of tubular structures configured to receive an end of needle 20. Upper jaw 16 and lower jaw 18 are longitudinally movable with respect to tubular portion 12 and with respect to each other. Additionally, within each jaw 14, 16 there is provided, as discussed in more detail below, a needle securing member to clamp needle 20 against the respective jaw. Needle 20 may be a curved surgical grade needle, such as, a USSC-CV cardiovascular surgical needle, available from United States Surgical Corporation, Norwalk, Conn., for example, and especially designed for vascular applications, i.e. for suturing of vessels.

Throughout this application, the term distal refers to the end of the apparatus, or component thereof, further from the user and term proximal refers to the end of the apparatus, or component thereof, closer to the user. Also, the terms upper and lower are used for convenience and refer to the orientation of the instrument as shown in FIG. 4. Clearly, if the instrument orientation changes, these designations will change as well. Further, while each of the disclosed embodiments is illustrated with a particular jaw structure for retaining a surgical needle, it should be noted that the jaws and associated structure for securing a needle within a jaw move parallel with respect to a longitudinal axis of the associated elongated tubular portion or portions. Thus, the various jaw structures of the embodiments may be interchanged with the specifically illustrated jaw structures as described in more detail below.

Turning first to the housing portion 12 of apparatus 10, and more particularly to FIGS. 2 and 3, housing portion 12 includes a pair of housing halves 12a, 12b which are essentially complimentary in configuration. Mounted within housing half 12a is a jaw actuating mechanism 28a and a needle control lever 30a; mounted within housing portion 12b is a jaw actuating mechanism 28b and a needle control lever 30b. Jaw actuating mechanisms 28a, 28b are each preferably configured as slidable buttons and are mounted for sliding movement within cutouts 32a, 32b formed in housing halves 12a, 12b, respectively. Grip portions 34a, 34b project from jaw actuating mechanisms 28a and 28b, and are advantageously ergonomically designed to facilitate manipulation by the user's thumb.

Inwardly projecting fingers 36a of jaw actuating mechanism 28a mount a proximal end 38 of jaw 16 to control longitudinal movement thereof. As noted hereinabove, jaw actuating mechanism 28a is provided to longitudinally advance and retract upperjaw 16. Lever 30a moves along with jaw actuating mechanism 28a and is also independently pivotable in a clockwise/counterclockwise direction about a mounting pin 40a affixed within a cutout 42a formed within jaw actuating mechanism 28a, to enable securement/release of needle 20 from upper jaw 16 in a manner discussed in more detail below. Needle control lever 30a projects through a reception opening 42a formed in upper jaw actuating mechanism 28a.

Jaw actuating mechanism 28b is identical in configuration to jaw actuating mechanism 28a. Jaw actuating mechanism 28b is slidably mounted within a recess 32b of housing half 12b and includes grip portion 34b and a reception opening 42b to receive lever 30b. Fingers 36b engage a proximal end 44 of lower jaw 18 to slide lower jaw 18 as jaw actuating mechanism 28b is slid longitudinally.

Turning now to the elongated endoscopic or tubular portion 14, and with particular reference to FIGS. 2 and 3, tubular portion 14 includes an outer tube 46 having an axial bore 48 therein. A guide tube 50 is positioned within outer tube 46 and guides jaws 16 and 18 along their longitudinal movement. Guide tube 50 is mounted within outer tube 46 such that through opening 52 is aligned with an aperture 54 formed in outer tube 46 to receive a pair of mounting pins 56 (only one of which is shown in FIG. 2) for securement to housing 12. Elongated longitudinal channels 58, 60 are formed on opposing sides of guide tube 50 for slidable reception of upper jaw 16 and lower jaw 18, respectively (see also FIGS. 3, 7 and 8). Upper jaw 16 is positioned within channel 58 and protrudes through a groove 62 in disc head 64. Similarly, lower jaw 18 is positioned within channel 60 to extend through groove 66 in disc head 64.

Figure 8:
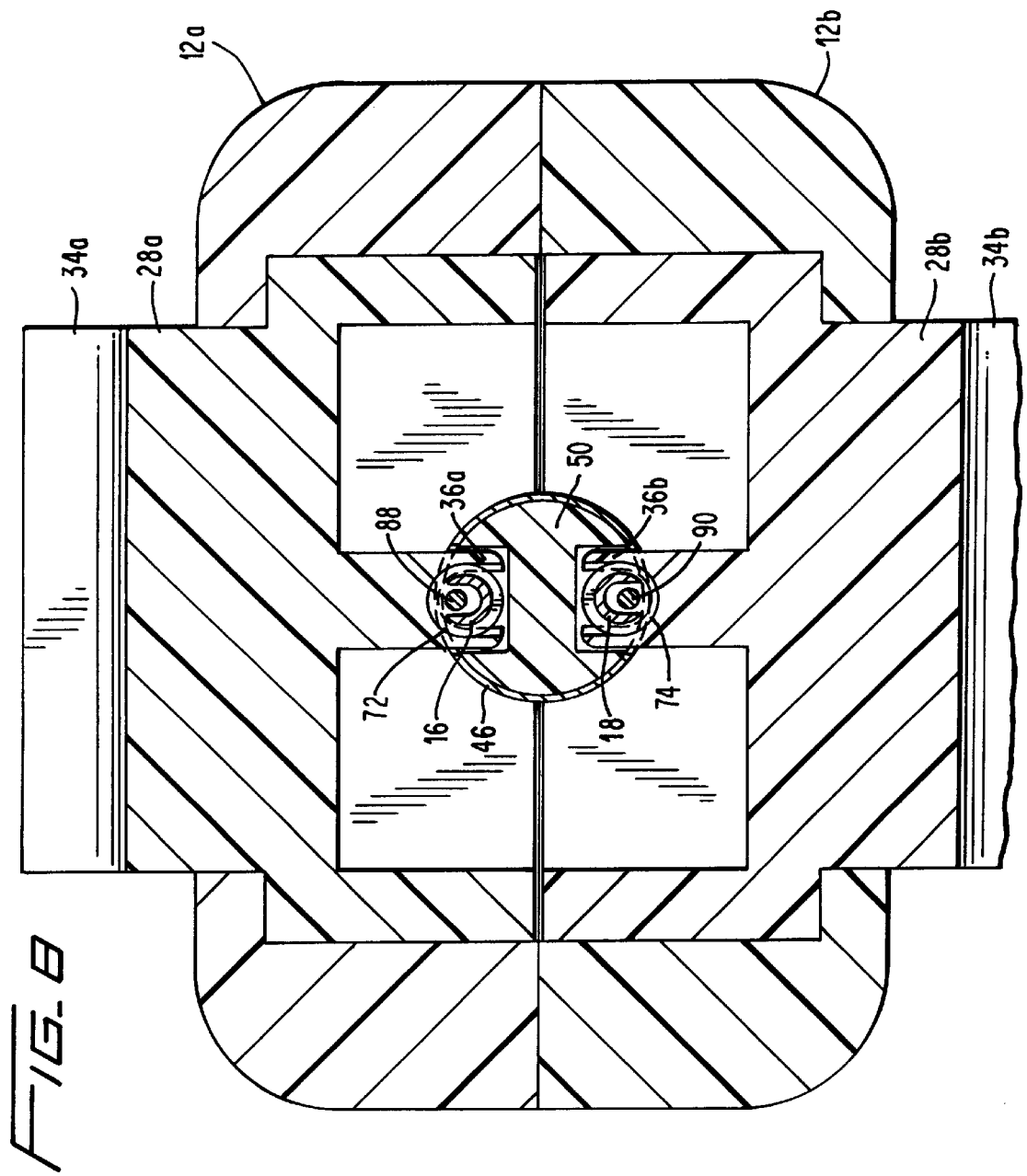
FIG. 8 is an enlarged cross-sectional view taken along lines 8—8 of FIG. 3.

Guide tube 50 includes recess portions 68, 70 dimensioned for receipt of proximal flanges 72, 74 formed on proximal ends 38, 44 of upper and lower jaws 16, 18, respectively. Proximal flange 72 of upper jaw 16 is frictionally mounted to fingers 36a of jaw actuating mechanism 28a, as best seen in FIG. 8, such that sliding movement of actuating mechanism 28a will slide upper jaw 16 accordingly. Similarly, proximal flange 74 of lower jaw 18 is mounted within fingers 36b of jaw actuating mechanism 28b for movement between proximal and distal positions. Both jaws terminate in a notch 76, 78 formed in distal ends 80, 82 to cooperate with their respective needle securing members.

Referring to FIGS. 2–4, and as noted above, each needle securing mechanism includes pivotable control lever (30a or 30b), a blade (84 or 86) cooperating with the notched portion of the jaw, and a connecting rod (88 or 90). More specifically, upper or first connecting rod 88 has a perpendicularly extending mounting extension 92 which is frictionally mounted within an opening 94a formed in lever 30a. Locking blade 84 is mounted over rod 88 and has an angled surface portion 96, best shown in FIG. 6, which presses needle 20 within jaw notch 76. Upper connecting rod 88 and locking blade 84 are slid proximally within jaw 16 by counterclockwise movement of lever 30a about pivot pin 40a as viewed in FIG. 3; clockwise movement moves these elements distally.

Lower or first connecting rod 90 is identical in configuration to upper rod 88 and has a perpendicular mounting extension 98 frictionally mounted within opening 94b of lever 30b and has locking blade 86 mounted to its distal end. Locking blade 86 has an angled surface 100 which cooperates with notch 78 of jaw 18 to securely hold the needle. Clockwise rotation of lever 30b about pivot pin 40b, as viewed in FIG. 3, slides lower rod 90 and locking blade 86 proximally within jaw 18; counterclockwise movement slides lower rod 90 and locking blade 86 distally.

In the distal position of the locking blade 84 or 86 the needle 20 is clamped (secured) between the notch of the jaw and the angled surface of the blade as shown in FIG. 6. When the locking blade 84 or 86 is retracted by the respective lever, the needle is no longer pressed into the notch and is released.

The operation of apparatus 10 will now be described. As shown in FIGS. 1, 4 and 5, in the initial position, needle 20 is clamped in both jaws 16 and 18. Referring to FIGS. 1 and 3, in this initial position, both jaw actuating mechanisms are in their distalmost positions and needle control levers 30a, 30b are in their retracted position. In this position, the jaws 16, 18 are in the extended position with respect to tubular portion 14 and locking blades 84 and 86 are in their distalmost position to press needle 20 into notches 76 and 78 of the respective jaw. With the needle 20 securely held in both jaws, apparatus 10 can be inserted through a trocar cannula, if desired, to position needle 20 within the body for suturing body tissue endoscopically. While the illustrated initial position has upper and lower jaws 16 and 18 in an extended position, both or one of the jaws 16 and 18 may be initially in a fully or partially retracted state.

Figure 9:
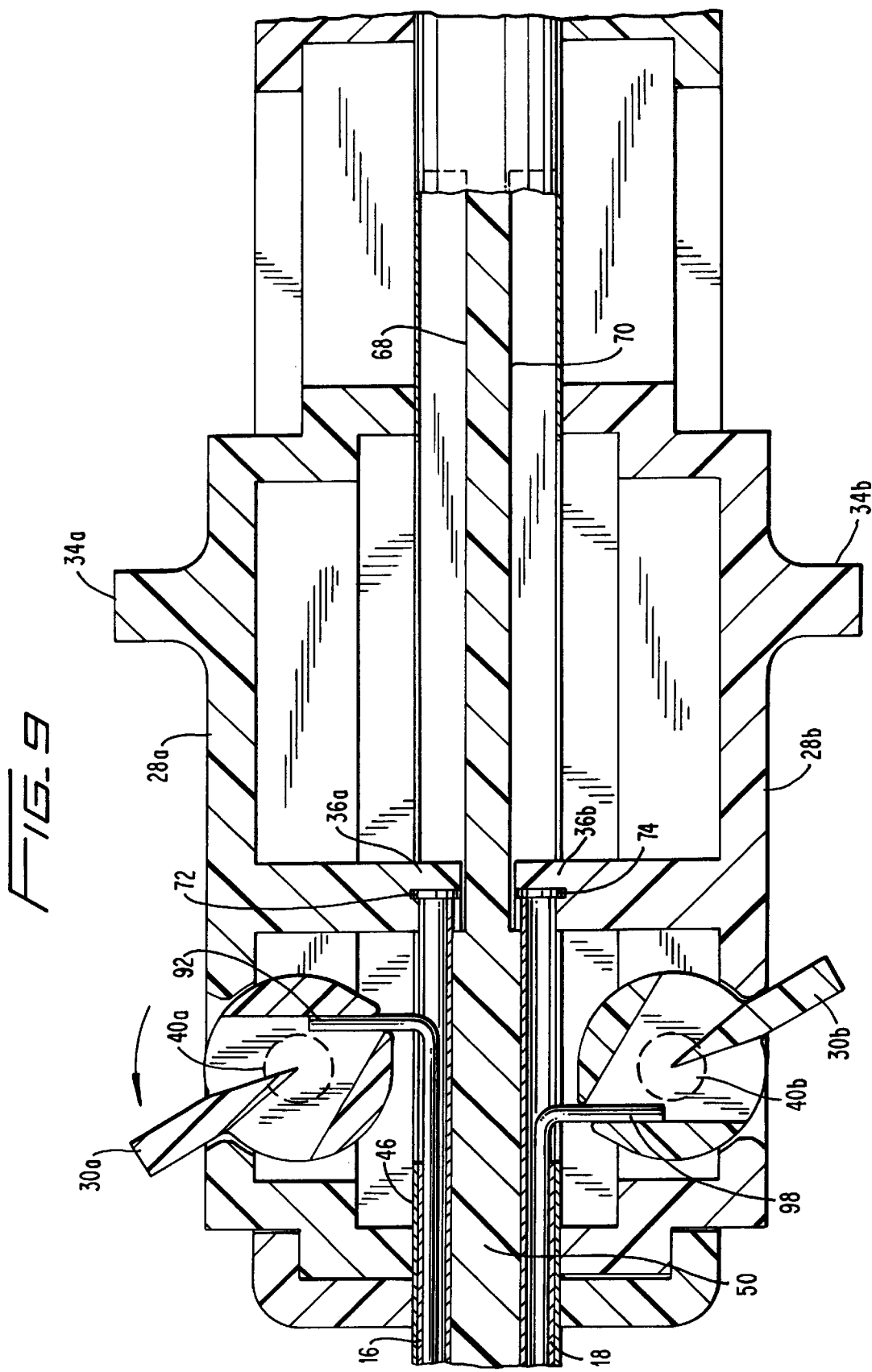
FIG. 9 is an enlarged cross-sectional view of the jaw actuating mechanisms of the apparatus showing the upper lever rotated counterclockwise to retract the upper needle securing member to release the needle from the upper jaw.
Figure 10:
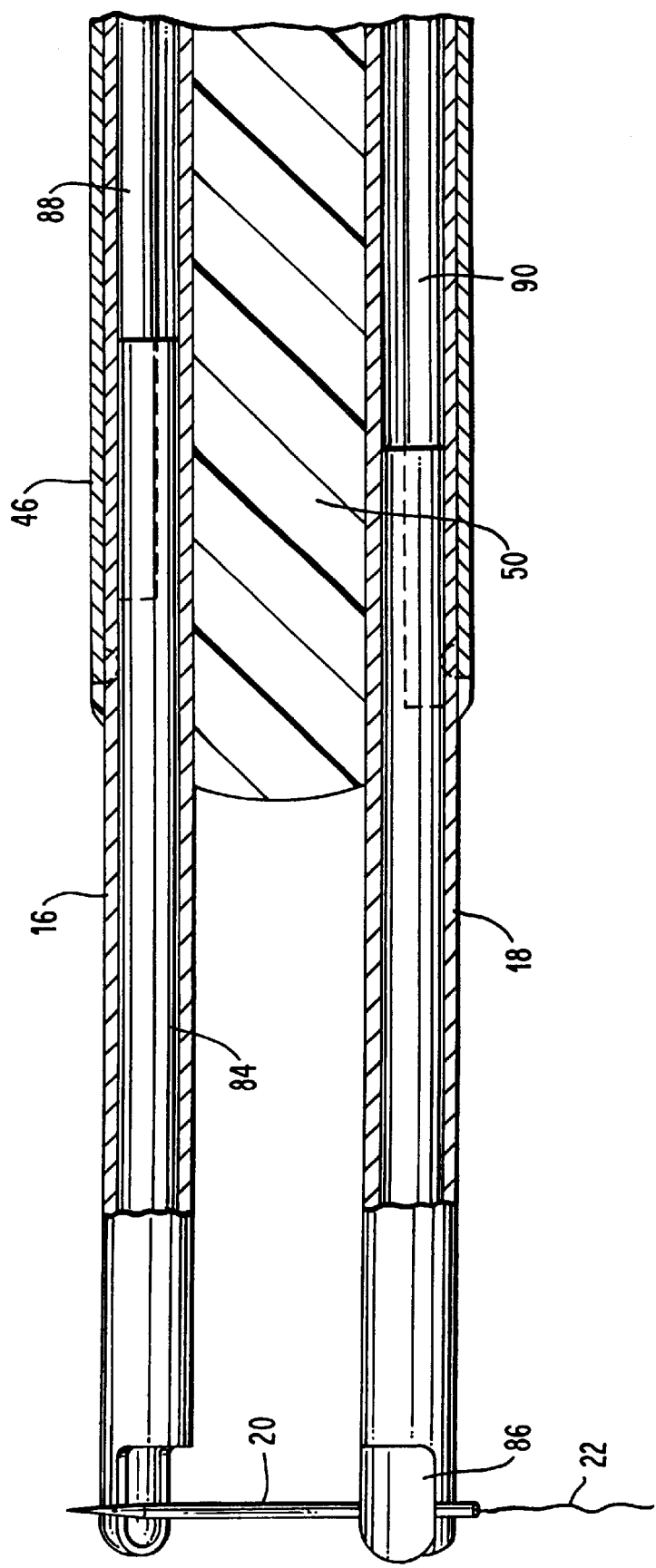
FIG. 10 is an enlarged cross sectional view of the distal end of the apparatus corresponding to the position of the needle securing mechanisms of FIG. 9 showing the needle clamped in the lower jaw and released from the upper jaw.

When it is desired to suture tissue, lever 30a is pivoted forward or counterclockwise as shown in FIG. 9 to slide locking blade 84 proximally out of engagement with the needle 20 to release the needle from upper jaw 16 as shown in FIG. 10. Needle 20 however is still fly retained in lower jaw 18 by locking blade 86.

Figure 11:
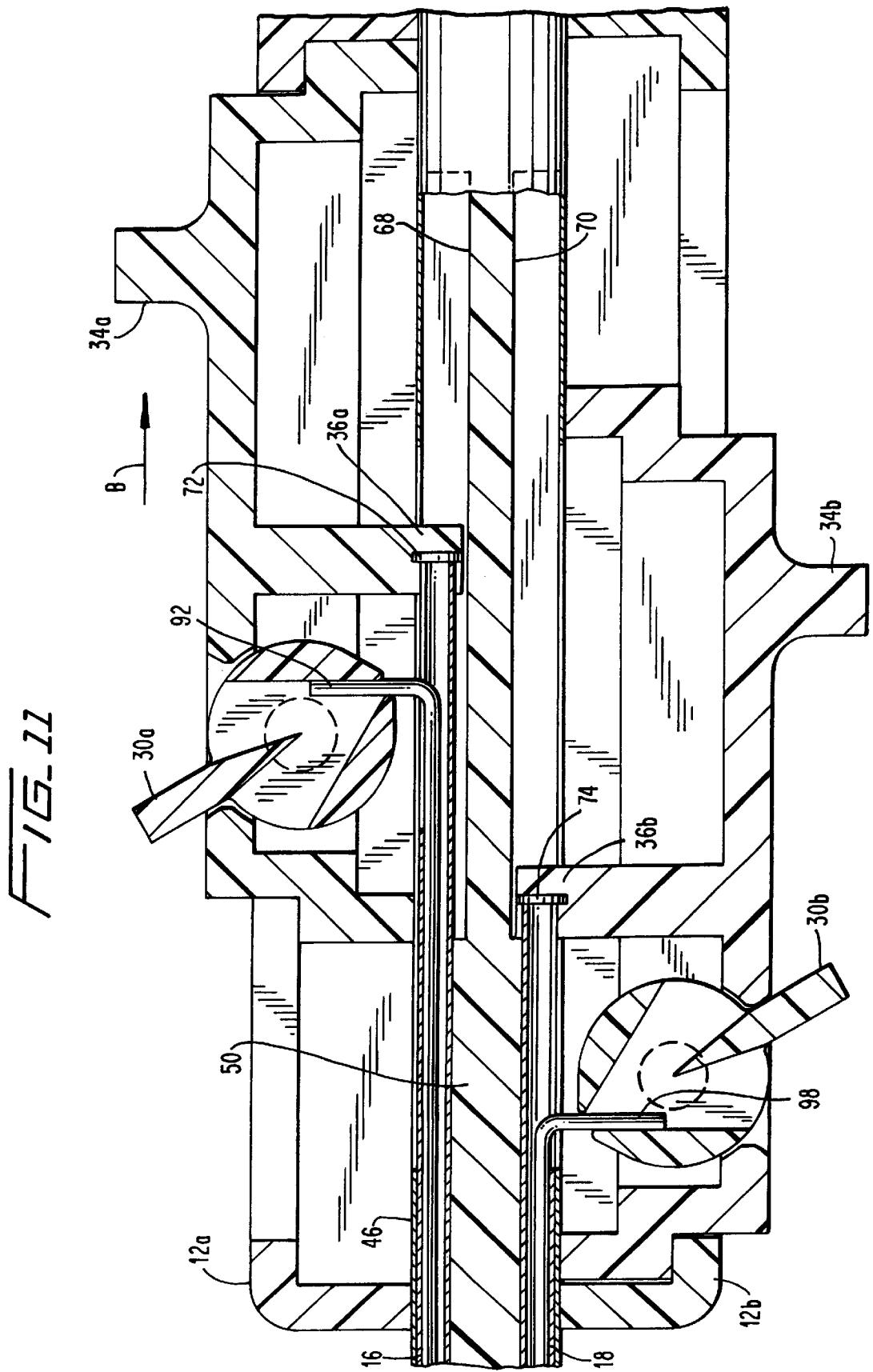
FIG. 11 is an enlarged cross-sectional view of the actuating mechanisms of the apparatus showing the upper jaw actuating mechanism moved to the proximal position to retract the upper jaw.
Figure 12:
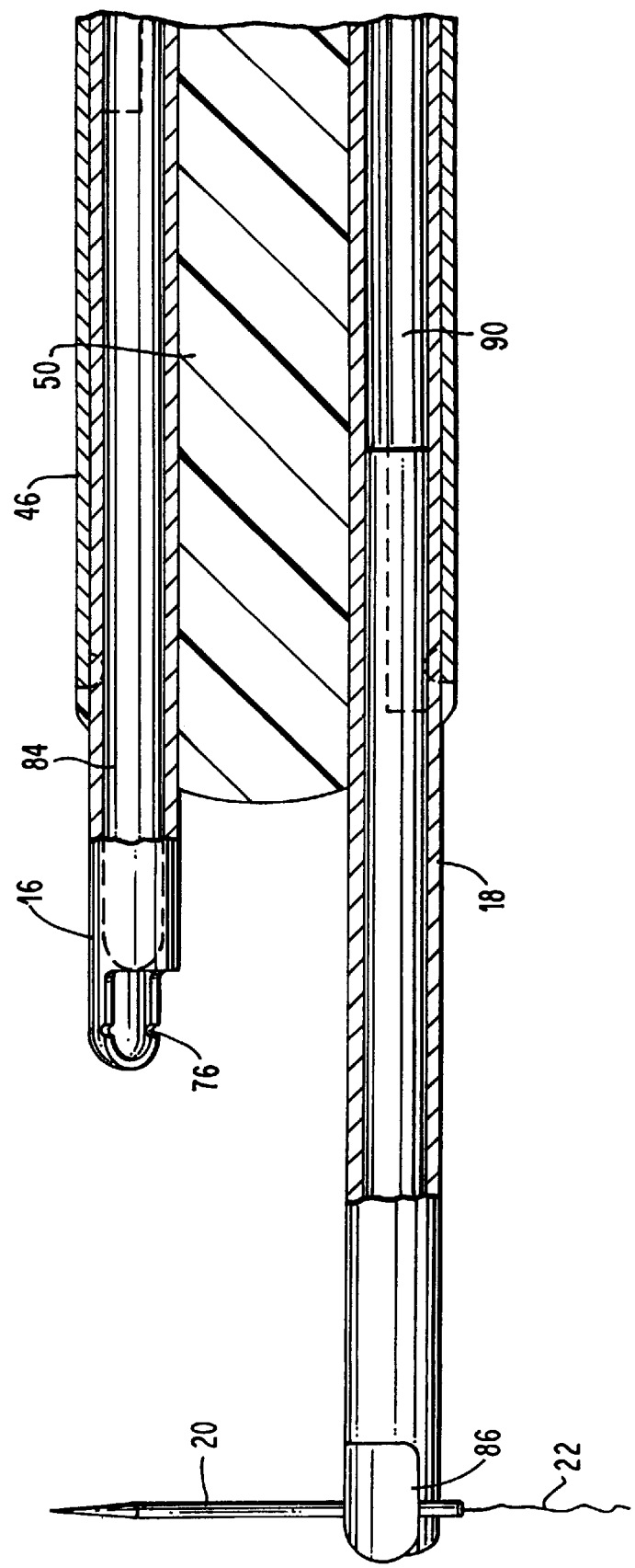
FIG. 12 is an enlarged cross-sectional view of the distal end of the apparatus corresponding to the position of the jaw actuating mechanisms in FIG. 11 showing the needle retained in the lower jaw and the upper jaw retracted to a proximal position.

Once needle 20 has been released from upper jaw 16, jaw 16 is then retracted out of the way (FIG. 12) by sliding jaw actuating mechanism 28a proximally in the direction of arrow B of FIG. 11. Thus the user can now manipulate needle 20 through body tissue to be sutured, for example, a vessel or the like.

Once needle 20 has been passed through the vessel or tissue, to draw suture 22 through the tissue and continue stitching, needle 20 needs to be grasped by jaw 16 and released from jaw 18 in order to pass control of needle 20 to jaw 16. This is accomplished by sliding jaw actuating mechanism 28a distally to advance jaw 16 into contact with needle 20. Lever 30a is subsequently pivoted clockwise to its initial position to advance locking blade 84 to clamp needle 20 within notch 76 of jaw 16. Once securely retained, lever 30b is rotated clockwise to retract the locking blade 86 to release needle 20 from jaw 18. Then jaw 18 is retracted out of the way by sliding jaw actuating mechanism 28a to its proximal position. Needle 20 and suture 22 may now be completely drawn through the tissue to form a stitch.

In order to position needle 20 within apparatus 20 to repierce tissue and form another stitch, needle 20 can be transferred back from jaw 16 to jaw 18 by sliding jaw actuating mechanism 28b distally to advance jaw 18 into engagement with needle 20. Lever 30b is rotated counter-clockwise to advance the locking blade 86 into engagement with needle 20 and secure it within jaw 18. Needle 20 is then released from jaw 16 in the manner described above. As is apparent, by individually controlling the movement of jaws 16 and 18 and the securing members or blades 84 and 86, the user can ensure that needle 20 is not released from one jaw until it is grasped in the other jaw. Thus, needle 20 can be repeatedly inserted through the vessel or tissue and passed between the jaws to suture the body tissue.

The suturing device described herein is particularly suited for vascular surgery and especially for endoscopic vascular surgery where space and visibility is limited. However, the apparatus can be used in non-endoscopic ("open") procedures as well. The ability to retract the jaws enables a standard curved vascular needle to be used. Although contemplated for vascular surgery the instrument can also be used to suture other body tissue. The instruments disclosed herein are also dimensioned and configured for insertion through a cannula.

Figure 13:
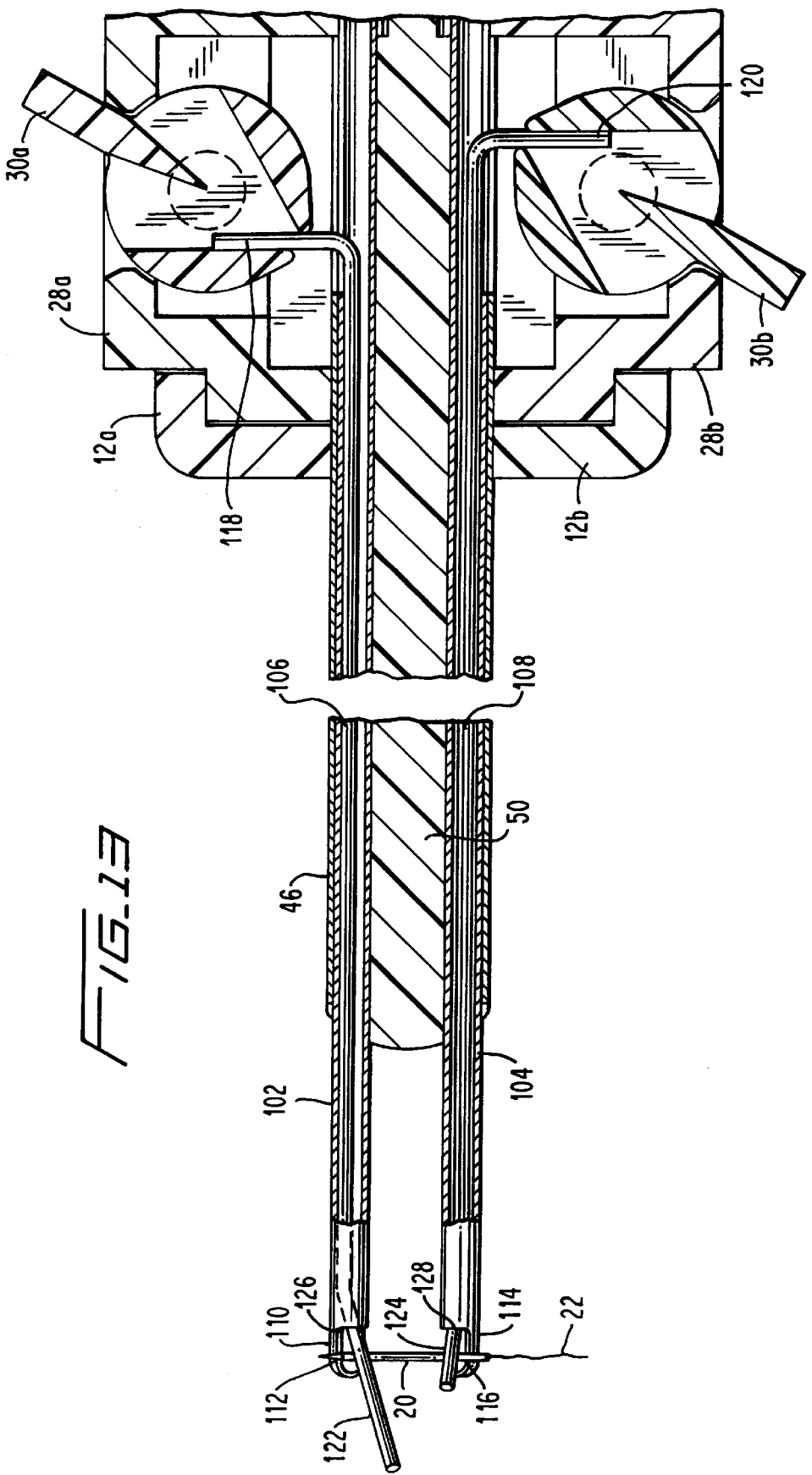
FIG. 13 is a cross-sectional view of an alternate embodiment of the suturing apparatus utilizing a bent wire to retain the surgical needle in the jaws and showing the needle secured in the lower jaw.

Referring now to FIGS. 13 and 14, there is disclosed an alternative jaw and needle securing member structure suitable for use with the housing and tubular portions, 12 and 14 of apparatus 10. When provided with the alternative jaw and needle securing member structure, apparatus 10 is substantially identical and performs in essentially the same manner as described hereinabove. The alternative jaw structure includes a modified first or upper jaw 102. a modified second or lower jaw 104 and modified connecting rods 106 and 108 for securing a surgical needle within upper and lower jaws 102 and 104. More specifically, upper jaw 102 has a cup shaped distal end 110 which includes a pair of needle receiving notches 112. Similarly, second or lower jaw 104 includes a cup shaped distal end 114 having a pair of needle receiving notches 116. While distal ends 110, 114 of upper and lower jaws 102, 104, respectively, are illustrated as being cup-shaped, it is within the contemplated scope of the present disclosure that distal ends 110, 114 be of various other configurations, such as, for example, v-shaped, open ended or straight through, etc.

In order to secure a surgical needle 20 within upper and lowerjaws 102 and 104 each connecting rod 106, 108 is provided with perpendicularly oriented mounting extensions 118 and 120 respectively. Mounting extensions 118 and 120 pass through openings 94a and 94b in needle control levers 30a and 30b in a manner similar to that of mounting extensions 92 with respect to connecting rods 88 and 90 described hereinabove. Thus, for example, clockwise rotation of lever 30a drives mounting extension 118 and thus connecting rod 106 distally while counter clockwise rotation of lever 30a drives mounting extension 118 and thus connecting rod 106 proximally. Counter clockwise rotation of lever 30b drives mounting extension 120 and thus connecting rod 108 distally while clockwise rotation drives mounting extension 120 and thus connecting rod 108 proximally. Additionally, distal advancement of jaw actuating mechanisms 28a and 28b drive their respective jaws 102 and 104 distally while proximal retraction of jaw actuating mechanisms 28a and 28b draw jaws 102 and 104 proximally, respectively.

In order to secure a needle 20 within notches 112, 116 of jaws 102 and 104, connecting rods 106 and 108 are formed or connected to needle securing members 122 and 124 having flexible distal portions. Needle securing members 122 and 124 cooperate with camming edges 126 and 128 formed on jaws 102 and 104 such that distal advancement of the needle securing member 122 or 124 allows the member to flex to an unstressed state releasing the needle from the respective needle securing notch while proximal retraction of the needle securing member will cause the flexible distal portion to abut the respective camming edges thereby flexing needle securing member 122 against surgical needle 20 and securing it within notches 112 or 114. Thus, clockwise rotation of lever 30a will release a surgical needle 20 from jaw 102 whereas counter clockwise rotation of lever 30a will secure needle 20 within jaw 102. Clockwise rotation of jaw 30b secures surgical needle 20 within lower jaw 104 whereas clockwise rotation of lever 30b releases a surgical needle from lower jaw 104. The alternative jaw structuring connecting rods disclosed herein FIG. 13 and 14 allow a surgical needle to be repeatedly transferred between the upper and lower jaws to facilitate suturing in substantially the same manner as described hereinabove.

It should be noted that in the above embodiments, clockwise movement of needle control lever 30*a* drives the associated needle securing member distally whereas clockwise movement of needle control member 30*b* draws the associated needle control member proximally. Conversely, counter clockwise movement of needle control lever 30*a* draws the associated needle securing member proximally while counter clockwise movement of needle control lever 30*b* advances the associated needle securing member distally. Thus, clockwise and counter clockwise movement of needle control members 30*a* and 30*b* result in opposite and reciprocal movements of the associated needle securing members. However, it is obvious that moving needle control levers 30*a* and 30*b* proximally drives the associated needle securing member distally, whereas advancing or rotating needle control levers 30*a* and 30*b* distally draws or moves the associated needle securing member proximally.

Referring now to FIGS. 15 and 16 there is disclosed an alternative control lever structure which is configured to advance or retract the associated needle securing member in the same direction that the needle control lever is moved, i.e., distally or proximally. The alternative structure generally incudes an upper jaw actuating mechanism 130 having an upper needle control lever 132 and a lower jaw actuating mechanism 134 having a lower needle control lever 136.

Upper jaw actuating mechanism 130 is slidably mounted in recess 32*a* of housing half 12*a*. Whereas previous embodiments have a needle control lever pivotally mounted within the associated jaw actuating mechanism, upper needle control lever 132 is slidably mounted within a recess 138 in upper jaw actuating mechanism 130. Similarly, lower jaw actuating mechanism 134 is slidably mounted in recess 32*b* of housing half 12*b* and lower needle control lever 136 is slidably mounted within a recess 140 formed in lower jaw actuating mechanism 134.

Flange 72 of upper jaw 16 is secured within a finger 142 of upper jaw actuating mechanism 130 and flange 74 of lower jaw 18 is secured within a finger 144 of lower jaw actuating mechanism 134. Thus, in a manner similar to previously disclosed embodiments, distal advancement of upper or lower jaw actuating mechanisms 130, 134 distally advances upper and lower jaws 16 and 18, respectively, while proximal retraction of upper or lower jaw actuating mechanism 130, 134, proximally retracts upper or lower jaws 16, 18, respectively.

Mounting extension 92 of connecting rod 88 is mounted within a bore 146 of upper needle control lever 132 and mounting extension 98 of connecting rod 90 is mounted within a bore 148 of lower needle control lever 136. Thus, as shown, each of upper and lower control levers 132, 136 moves in the same direction, i.e., proximally or distally, to proximally retract or distally advance connecting rods 88, 90, and, hence, blades 84, 86, respectively.

Referring now to FIGS. 17 and 18 there is shown alternative jaw or needle grasping structure. This alternative structure includes a first or upper jaw 150 and a second or lower jaw 152. Upper and lower jaws 150 and 152 are configured to releasably grasp ends of a surgical needle, such as surgical needle 20, to facilitate suturing of tissue. Jaw 152, including lower sleeve 158 and lower needle grasper 160, is structurally and functionally similar to jaw 150 and thus operates in the same manner. Upper jaw 150 generally includes an upper sleeve 154 and pair of needle graspers 156. Upper jaw 150 is configured to function with the jaw actuating mechanisms and needle control levers described hereinabove. Thus, sleeve 154 extends through disc head 64 and outer tube 46 and has a proximal end (not shown) which is connected to a needle control lever. Upper needle grasper 156 includes a shank 162 and a pair of flexible opposing arms 164, 166 formed integrally with, and extending distally from, shank 162. A proximal end (not shown) of shank 162 is connected to a jaw actuating mechanism.

Arms 164, 166 are initially biased to an open position and have camming edges 168, 170, respectively. Sleeve 154 has a camming edge 172 at a distal end thereof. Advancing a needle control lever moves sleeve 154 distally, moving camming edge 172 distally into contact with camming edges 168, 170 on arms 164, 166 respectively to cam arms 164, 166 together to grasp needle 20 positioned therebetween. Retraction of a needle control lever draws sleeve 154 proximally allowing arms 164, 166 to bias apart and release needle 20.

When needle 20 has been released, proximal movement of a jaw actuating mechanism of the type described hereinabove, draws upper needle grasper 150 as well as sleeve 154 proximally out of the way of needle 20 to facilitate suturing. Similarly, distal advancement of the jaw actuating mechanism advances needle grasper 156 and sleeve 154 into a position to surround and grasp surgical needle 20.

As noted hereinabove, the various illustrated jaw structures may be interchanged with alternative jaw actuation and needle control structure. For example, in FIGS. 1–4, jaw actuating mechanisms 28*a* and 28*b*, as well as needle control levers 30*a* and *b*, may preferably be provided to advance upper jaw 102 and lower jaw 104 (FIG. 14) as well as move upper and lower connecting rods 106, 108 within upper and lower jaws 102 and 104 to release and secure needle 20 therein. Additionally, jaw actuating mechanisms 28*a* and 28*b*, as well as needle control levers 30*a* and 30*b*, may be provided to control upper and lower sleeves 154, 158 and upper and lower needle graspers 156 and 160 (FIGS. 17 and 18). Further, upper and lower jaw actuating mechanisms 130 and 134, as well as upper and lower needle control levers 132 and 136 (FIGS. 15 and 16) may preferably be provided to control the motions of upper and lower jaws 16 and 18 as well as blades 84 and 86 to secure and release needle 20 from notches 76 and 78 within upper and lower jaws 16 and 18, respectively.

In the previously described embodiments, the operations of grasping and releasing the needle as well as moving the needle grasping assemblies into and out of a position to grasp the surgical needle were each individually performed.

Referring now to FIG. 19 there is illustrated a surgical suturing apparatus configured to sequentially and alternately grasp and release different portions of a surgical needle in response to repeated closures of one or more control levers. Suturing apparatus 200 generally includes a housing 202 and an elongated tubular portion 204 extending distally from housing 202. Housing 202 is preferably formed of two symmetrical halves to facilitate construction and assembly of suturing apparatus 200. Elongated tubular portion 204 is preferably configured to be insertable through a cannula. An upper or first jaw 206 and a lower or second jaw 208 extend distally from elongated tubular portion 204 and are longitudinally movable with respect thereto. First and second jaws 206 and 208 are configured to releasably grasp a surgical needle, such as surgical needle 210 having a suture 212 attached thereto, and to repeatedly pass surgical needle 210 between jaws 206 and 208 to facilitate suturing of tissue. Elongated tubular portion 204, along with first and second jaws 206 and 208, are dimensioned and configured to fit within conventional cannulas.

In order to actuate first and second jaws 206 and 208, there is provided an actuation mechanism in the form of a pair of control levers 214, 214a which together or individually operate jaws 206 and 208 in a manner described in greater detail hereinbelow. A first loading mechanism 216 and a second loading mechanism 218 are provided to override the actuation mechanism and allow surgical needles to be inserted and removed from jaws 206 and 208.

Suturing apparatus 200 functions through four separate cycles to completely pass surgical needle 210 between first jaw 206 and second jaw 208. For example, a single complete depression of either control lever 214, 214a initially releases surgical needle 210 from first jaw 206 and subsequently retracts first jaw 206 away from surgical needle 210, thereby allowing a surgeon to pass needle 210 through tissue. Upon release of control lever 214, 214a, control lever 214, 214a, is biased to its original, open position. A second complete depression of control lever 214 and/or 214a advances first jaw 206 to again grasp needle 210, while a third complete depression of control lever 214 and/or 214a initially releases surgical needle 210 from second jaw 208 and subsequently retracts second jaw 208 proximally away from surgical needle 210. Thus, the surgeon may pull surgical needle 210, and attached suture 212, through the tissue to form a stitch. Finally, a fourth complete depression of control lever 214 and/or 214a advances second jaw 208 adjacent surgical needle 210 and causes second jaw 208 to again grasp surgical needle 210. Thus, upon four complete cycles, control of surgical needle 210 is passed from one jaw to the other and finally back to the initial position being releasably grasped by both first jaw 206 and second jaw 208. It should be noted that jaws 206 and 208 move longitudinally or parallel to a longitudinal axis of elongated tubular portion 204 as well as housing 202.

Referring now to FIGS. 20, 21 and 21A, in order to releasably secure a portion of surgical needle 210 within a jaw, such as jaw 206, jaw 206 includes a tubular first jaw sleeve 220 slidably mounted within elongated tubular portion 204 and a first needle retaining arm 222 slidably mounted within first jaw sleeve 220. A first notch 224 is formed in arm 222 and is configured to receive a portion of surgical needle 210 therein. A flexible first finger 226 is mounted within arm 222 and extends adjacent first notch 224. First finger 226 is biased away from notch 224 (as best seen in FIG. 25) into a release position. By advancing first jaw sleeve 220 over first finger 222, a distal end 228 of first jaw sleeve 220 forces first finger 222 against its bias and adjacent first notch 224 to securely and releasably hold a portion of surgical needle 210 therein.

Similarly, second jaw 208 includes a second jaw sleeve 230 movably mounted within elongated tubular portion 204 and a second needle retaining arm 232 movably mounted within second jaw sleeve 230. Second arm 232 has a second notch 234 therein to receive a portion of surgical needle 210 and a flexible second finger 236 to releasably secure needle 210 within notch 234. A distal end 238 of second jaw sleeve 230 engages second finger 236 to move finger 236 between a needle securing position and a needle releasing position in the same manner as first jaw 206.

Referring now to FIG. 20, and as discussed above, first and second jaw sleeves 220 and 230, as well as first and second needle retaining arms 222 and 232, are slidably mounted and longitudinally movable within elongated tubular portion 204. Elongated tubular portion includes an outer cover 240 and a support member 242 mounted within cover 240. Support member 242 includes opposed, longitudinally extending first and second channels 244 and 246 which receive first and second jaw sleeves 220 and 230 respectively. Outer cover 240 is affixed to support member 242 by a pin 248.

First and second jaw sleeves 220 and 230 and first and second needle retaining arms 222 and 232 are each driven in their longitudinal directions within first and second channels 244 and 246 by separate, individual drive hubs. The drive hubs are longitudinally movable within housing 202 in response to actuation of control levers 214, 214a in a manner described in more detail hereinbelow. A first sleeve hub 250 is provided to drive first jaw sleeve 220 within channel 244 and a first arm hub 252 is provided to drive first needle retaining arm 222 within first jaw sleeve 220. In order to mount first jaw sleeve 220 to first sleeve hub 250, there is provided a first mounting block 254 which is positioned within a cavity 256 (best seen in FIG. 22) of hub 250. A flange 258 at a proximal end of first jaw sleeve 220 fits securely within a groove 260 in first mounting block 254. A pair of springs 262 fit within cavity 256 and engage and bias first mounting block 254 distally within cavity during normal operation of apparatus 200. However, springs 262 allow first mounting block 254 and thus first jaw sleeve 220 to be moved proximally and independently of control levers 214 to facilitate loading or unloading of a surgical needle 210 in the manner described hereinbelow.

A proximal end 264 of first needle retaining arm 232 protrudes through a slot 266 in first jaw sleeve 220 and is fixed within a bore 268 of first arm hub 252.

Similarly, there is provided a second sleeve hub 270 and a second arm hub 272 to drive second jaw sleeve 230 and second needle retaining arm 232 longitudinally within elongated tubular portion 204, respectively. A second mounting block 274 is positioned within a cavity 276 in second sleeve hub 270. A flange 278 of second jaw sleeve 230 engages a groove 280 in second mounting block 274. Springs 282 bias second mounting block 274 distally within cavity 276 during normal operation and, as with springs 262 above, allow loading of a surgical needle independently of control levers 214.

A proximal end 284 of second needle retaining arm 232 extends through a slot 286 in second jaw sleeve 230 and is fixed within a bore 288 in second arm hub 272.

As indicated hereinabove, springs 262 and 282 allow loading of surgical needle 210 independently of actuation of control levers 214. Referring now to FIGS. 20 and 22 through 25, first loading mechanism 216 generally includes a first release slide 292, a first transfer bar 294 and a first block driver 296 which function together to retract sleeve 220 in order to release needle 210 from first needle retaining arm 222. Release slide 292 is slidably mounted to housing 202 while transfer bar 294 is pivotably mounted about a stud 298 in housing 202. Block driver 296 is slidably mounted within housing 202 such that upon distal movement of release slide 292, slide 292 contacts transfer bar 294 to pivot transfer bar 294 about stud 298. This causes an edge of transfer bar 294 to engage block driver 296 and move it proximally within housing 202. Proximal movement of block driver 296 causes it to engage first mounting block 254 and drive mounting block 254 proximally against the bias of springs 262. Thus, as first mounting block 254 is driven proximally, it draws first jaw sleeve 220 proximally to release or insert a portion of surgical needle 210 within first needle retaining arm 222.

To prevent inadvertent release of surgical needle 210, first loading mechanism includes a first latch button 300 having locking arms 302. First latch button 300 is movably mounted within first release slide 292 such that locking arms 302 engage housing 202 to prevent movement of first release slide 292. Depression of first latch button 300 against the bias of a spring 304 moves locking arms 302 out of engagement with housing 202 and into position within grooves 306, formed within housing 202, allowing first release slide 292 to move with respect to housing 202.

Similarly, in order to release surgical needle 210 from second needle retaining arm 232, second jaw loading mechanism 218 generally includes a second release slide 308 movably mounted to housing 202 and a second transfer bar 310 pivotally mounted on a stud 312 on housing 202. A second block driver 314 is slidably mounted within housing 202 between second transfer bar 310 and second mounting block 274. Moving second release slide 308 distally pivots second transfer bar 310 about stud 312 to drive second block driver 314 and thus second mounting block 274 proximally against the bias of springs 282. Thus, second jaw sleeve 230 is drawn proximally to release or insert a portion of surgical needle 210 within second needle retaining arm 232.

Second jaw loading mechanism 218 also includes a second latch button 316 mounted in second release slide 308 and having locking arms 318 which are movable within grooves 320 in housing 202 when second latch button 316 is depressed against the bias of a spring 322.

Referring now to FIGS. 20 and 26, guide member 290 is provided to guide first and second sleeve hubs 250, 270 and first and second arm hubs 252, 272 longitudinally within housing 202. Guide member 290 includes a circular plate 324 affixed within housing 202 and abuts a flange 325 (FIG. 20) in camming sleeve 344 described in more detail hereinbelow. Plate 324 defines a bore 326 through which outer cover 240 passes. First and second guide arms 328, 330, respectively, extend distally from plate 324. Return springs 332 and 334 are provided at ends of guide arms 328 and 330 and serve to bias first and second transfer bars 294, 310 against pivotal movement.

First guide arm 328 extends through bores 336 and 338 formed in first sleeve hub 250 and first arm hub 252, respectively. First arm hub 250 and first sleeve hub 252 are freely slidable along first guide arm 328.

Similarly, second sleeve hub 270 and second arm hub 272 are provided with bores 340, 342, respectively, through which second guide arm 330 extends allowing second sleeve hub 270 and second arm hub 272 to be freely slidable thereon.

As discussed hereinabove, first and second sleeve hubs 250, 270 and first and second arm hubs 252, 272 are longitudinally movable within housing 202 so as to alternately grasp and release surgical needle 210 within first and second jaws 206 and 208.

Figure 28:
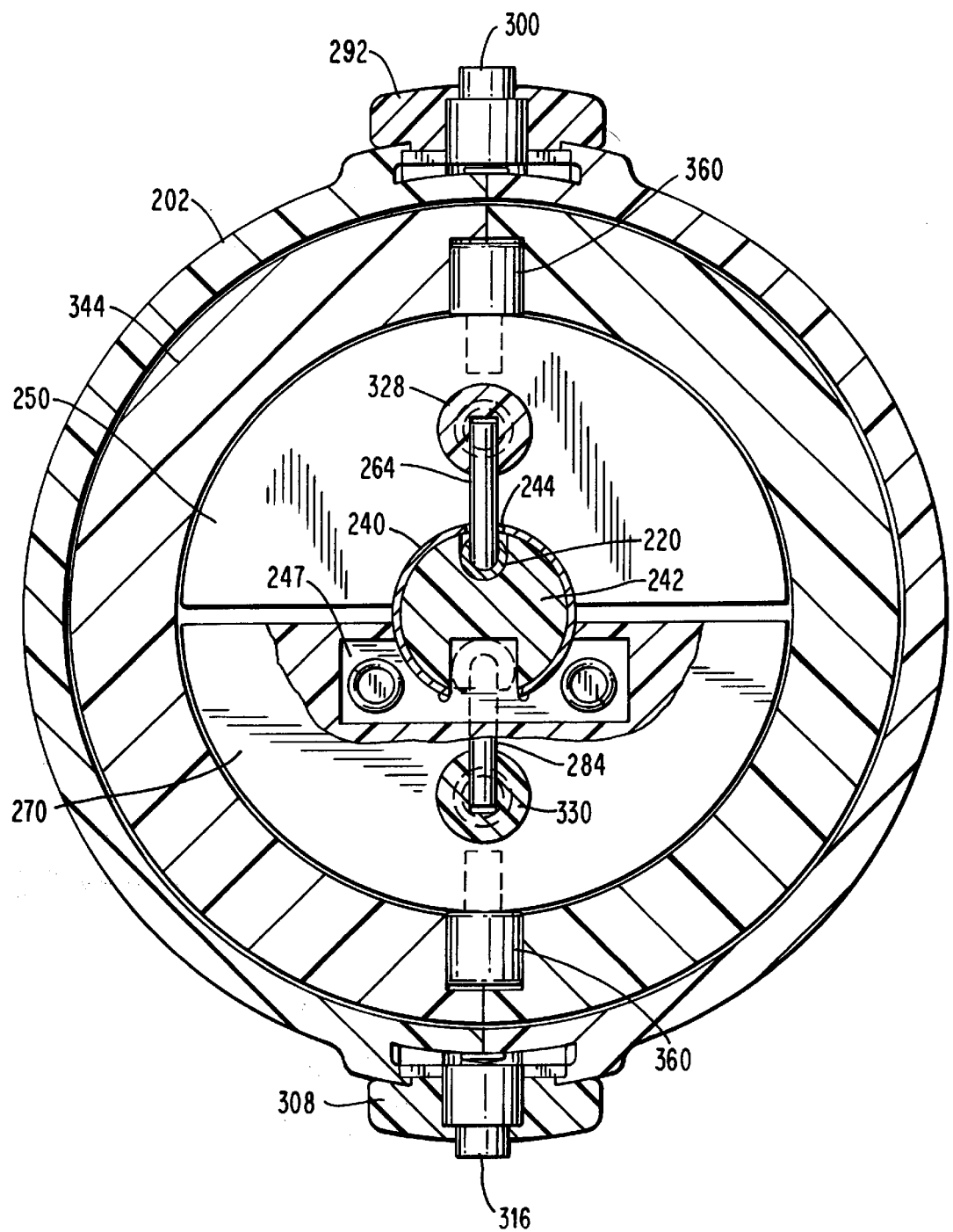
FIG. 28 is a sectional view taken along line 28—28 of FIG. 22.

Referring now to FIGS. 20, 26, 27 and 28, in order to move the various hubs longitudinally in a predetermined sequence, there is provided a camming sleeve 344 (which may be formed as halves or unitary) which, as best seen in FIG. 28, is mounted for rotation between housing 202 and the various hubs. Camming sleeve 344 has a distal portion 346 which surrounds the hubs and a reduced diameter proximal portion 348 extending into a central area 350 of housing 202. Flange 325 internally separates distal portion 346 from proximal portion 348 and defines a bore 352 through which outer cover 240 extends.

Camming sleeve 344 includes a sleeve cam groove 354 and an arm cam groove 356 formed in a inner surface 358 of distal portion 346. Grooves 354 and 356 extend completely radially around inner surface 358 and are specifically configured to sequence the movements of the various hubs in a predetermined manner. The grooves include portions which remain constant in longitudinal position and impart no longitudinal motion to the hubs and portions which vary in longitudinal position along inner surface 358 of camming sleeve 344 to drive the hubs.

The transfer of the rotary motion of camming sleeve 344 to longitudinal movement of the various hubs is accomplished by use of cam rollers which are affixed to the hubs and which ride within the grooves. For example, in order to move the sleeve hubs longitudinally, sleeve hub 250 includes a cam roller 360 which rides within sleeve cam groove 354. Cam roller 360 is fixed to first sleeve hub 250 by a pin 362 which extends into a hole 364 in first sleeve hub 250. Cam roller 360 is free to rotate about pin 362 and slide within sleeve cam groove 354. Similarly, second sleeve hub 270 is moved by a cam roller 366 affixed thereto by means of a pin 368 fixed within a hole 370 in second sleeve hub 270.

Likewise, first arm hub 252 is provided with a cam roller 372 which rides in arm cam groove 356 to move first arm hub 252 in a predetermined manner. Cam roller is attached to first arm hub 252 by a pin 374 extending into a hole 376 in first arm hub 252. Cam roller 372 is free to rotate about pin 374 and slide within arm cam groove 356. Similarly, second arm hub 372 includes a cam roller 378 and a pin 380 affixed in a hole 382 in second arm hub 272. Cam roller 378 is free to rotate about pin 380 and slide within arm cam groove 356.

Thus, rotation of camming sleeve 344 within housing 202 drives cam rollers 360 and 366 and cam rollers 372 and 378 within sleeve cam groove 354 and arm cam groove 356, respectively. This movement moves hubs 250, 252 and hubs 270, 272 in predetermined sequence to open and close and advance and retract first and second jaws 206 and 208 about surgical needle 210.

As noted above, four separate cycles of levers 214 are required to position surgical needle 210 within a single jaw, pass needle 210 through tissue, transfer control to the other jaw, draw suture 212 through tissue and repass surgical needle 210 back to the original jaw. These four cycles are accomplished by rotating camming sleeve 344 in four discrete and equal quarter turn rotations.

Referring to FIG. 27, camming sleeve 344 is provided with a drive groove 384 formed in an outer surface 386 of proximal portion 348. Drive groove 384 includes four equally spaced driving portions 388 which extend both radially and longitudinally about outer surface 386. Additionally, drive groove 384 further includes four equally spaced and longitudinally extending return portions 390. Each return portion 390 extends between a proximal end of one driving portion and a distal end of the next adjacent driving portion.

A pair of drive bars 392, 394 are provided and are longitudinally movable within housing 202 in response to depression of either lever 214 and/or 214*a* (either lever 214 and/or 214*a* may be depressed, however, further discussion will be in terms of control lever 214). Notably, suturing apparatus 200 operates satisfactorily with a single drive bar 392 or 394 and may preferably be configured as such.

Rollers 396, 398 are provided on pins 397 and 399 (not shown) pressed into drive bars 392, 394, respectively. Each roller 396, 398 rides within drive grove 384. Upon proximal retraction of drive bars 392, 394, in response to a single depression of a lever 214, rollers 396, 398 are drawn from the distal end of an opposed pair of driving portions to rotate cam ng sleeve 344 one quarter turn. Upon release of lever 214, drive bars 392, 394 and thus rollers 396, 398 move longitudinally within return portions 390 thereby repositioning rollers 396, 398 within distal end of driving portions 388 without further rotation of camming sleeve 344.

Referring to FIGS. 20, 29 and 30, a drive rod 400 is provided to draw proximally and advance distally drive bars 392, 394. A distal end 402 of drive rod 400 has a hole 404 for receipt of a pin 406. Pin 406 extends through an aperture 408 in drive bar 392, through hole 404 and through an aperture 410 in drive bar 394. A spring 412 is provided about a proximal end 414 of drive rod 400 and abuts a flange 416 of drive rod 416 to bias drive rod 400 distally.

Control lever 214 moves rod 400 by means of a first wedge 418 which is pivotably mounted within a slot 420 in lever 214 by means of pin 422 which extends through a hole 424 in lever 214 and through a hole 426 in first wedge 418. A first leaf 428 is pivotably affixed to housing 202 at a distal end 430 and to first wedge 418 at a proximal end 432 by a pin 434 which extends through a hole 436 in leaf 428 and a hole 438 in wedge 418.

First wedge 418 has a camming surface 440 configured to engage a roller 442 mounted on drive rod 400 by means of a pin 444. Depressing lever 214 causes wedge 418 to rotate proximally about pin 434. As wedge 418 rotates about pin 434, camming surface 440 drives roller 442 proximally and thus drive rod 400 proximally against the bias of spring 412.

Thus, by depressing control lever 214, drive rod 400 is drawn proximally thereby rotating camming sleeve one quarter turn. In order to ensure that drive studs 396, 398 travel proximally through drive portions 388 and not back in longitudinal return portions 390, guide bars 446 are provided to guide rollers 396, 398 into drive portions 388 by engaging and deflecting guide pins 448 positioned opposite rollers 396, 398.

Similarly, lever 214a has a wedge 418a positioned within a slot 420a therein by means of a pin 422a. A leaf 428a is connected between housing 202 and wedge 418a in the same manner as above with respect to wedge 418. Wedge 418a has a camming surface 440a which engages a roller 434a to move drive rod 400 proximally in response to a depression of lever 214a. Levers 214 and 214a may operate together or independently to rotate camming sleeve one quarter turn upon each depression of lever 214 and/or 214a.

The operation of suturing apparatus 200 will now be described. Referring initially to FIG. 25, suturing apparatus 200 is initially loaded with a surgical needle 210 having suture 212 attached thereto. The loading procedure is the same as described hereinabove, namely first release slide 292 is moved distally to pivot first transfer bar 294 about stud 298. Pivoting first transfer bar 294 about stud 298 drives first block driver 296 proximally thereby forcing first mounting block 254 proximally against the bias of springs 262. As first mounting block 254 moves proximally, it draws first jaw sleeve 220 proximally allowing flexible first finger 226 to be biased to an open position. Surgical needle 210 may now be positioned within first notch 224 in first needle retaining arm 222.

Releasing first needle slide 292 allows first transfer bar 294 to return to initial position due to the bias of spring 332. First jaw sleeve 220 also moves distally due to the bias of springs 262 to cam flexible first finger 226 against surgical needle 210 thereby securely holding surgical needle 210 within first notch 224 of first needle retaining arm 222. Similar operation of second jaw loading mechanism 218 may be performed to secure an opposing end of surgical needle 210 within second notch 234 of second needle retaining arm 232. Thus, surgical needle 210 having suture 212 attached thereto is securely held between first jaw 206 and second jaw 208 and is in a position ready for use during the surgical operation.

Referring now to FIGS. 30 and 31, in an initial position, control levers 214, 214a are biased to an open position by spring 412. This places rollers 396 and 398 in a distalmost position within the return portions 390 of drive groove 384. Camming sleeve 344 is oriented such that first and second sleeve hubs 250 and 270 and first and second arm hubs 252 and 272 are in a distalmost position. As best seen in FIG. 31, needle 210 is securely held between jaws 206 and 208.

Referring now to FIG. 32, to begin operation of surgical suturing apparatus 200, control lever 214 is initially depressed toward housing 202 thereby drawing rollers 396 and 398 proximally within driving portions 388 of camming sleeve 344. This causes an initiation of the rotation of camming sleeve 344. Guide bars 446 force rollers 396, 398 in driving portion 388 rather than return portion 390.

Referring now to FIGS. 33 and 34 along with FIG. 37, as control lever 214 is continued to be depressed, camming sleeve 344 continues to rotate drawing first jaw sleeve 220 proximally to release surgical needle 210 from first jaw 206. Specifically, as shown in FIG. 37, this occurs when cam roller 360 moves between portions A and B within sleeve cam groove 354. As shown, during this initial movement cam roller 372 continues to move between position A', B' within arm cam groove 356 along straight circumferential portion of arm cam groove 356 and thus does not move first arm hub 252.

Referring now to FIGS. 35 and 36 along with FIG. 37, as control lever 214 has been completely depressed, cam sleeve 344 moves through a complete quarter turn rotation thereby drawing cam roller 360 between position B and C within sleeve cam groove 354 and drawing cam roller 372 between position B', C' in arm cam groove 356. This rotation of camming sleeve 344 moves first sleeve hub 250 and first arm hub 252 equally to withdraw first jaw 206 away from surgical needle 210. Suturing apparatus 200 may now be utilized to manipulate surgical needle 210 through a tissue section and into a position to be grasped and drawn through tissue, for example, tissues X and Y.

With reference to FIGS. 30 and 38, upon release of control lever 214, control lever 214 is again biased outwardly by spring 412. This moves rollers 396 and 398 to a distalmost position along return portions 390 of drive groove 384. As shown, return portions 390 are parallel to the longitudinal axis of surgical instrument 200 and impart no rotation to camming sleeve 344.

Referring now to FIGS. 39 and 40 along with FIG. 37, upon a second initiation of depression of control lever 214, cam roller 360 moves between positions C and D within sleeve cam groove 354 and simultaneously cam roller 372 moves between positions C', D' in arm cam groove 356 to thereby simultaneously advance first jaw 206 distally towards surgical needle 210 to be in a position to again grasp surgical needle 210. This initial depression of control lever 214 initiates a second quarter turn rotation of cam sleeve 244.

Referring now to FIGS. 41 and 41A along with FIG. 37, continued depression of control lever 214 advances first jaw 206 about surgical needle 210. Cam roller 372 begins to enter an area between positions D', E' within arm cam groove 356 and first arm hub 252 has no further distal motion. Cam roller 360, however, moves between positions D and E within sleeve cam groove 354 to continue to drive sleeve hub 250 and thus first sleeve 222 distally. Distal movement of first sleeve 222 again cams flexible first finger 226 against surgical needle 210 and to grasp surgical needle 210 within first notch 224 in first needle retaining arm 222.

In this manner, upon two quarter turn rotations of cam sleeve 344, i.e. one-half rotation of cam sleeve 244, first jaw 206 has released surgical needle 210 and retracted out of the way to allow the user to form a stitch and has again advanced and grabbed surgical needle 210 to be in a position to draw surgical needle 210 through the tissue to be sutured.

It will be noted that upon subsequent depression of either control lever 214, 214a cam rollers 366 and 378 will initially move between positions A, A', and B, B' to draw second jaw sleeve 230 proximally thereby releasing surgical needle 210 from within second notch 234 in second needle retaining arm 232. As cam rollers 366 and 378 move between positions B, B' and C, C' second jaw 208 is drawn away from surgical needle 210. Surgical needle 210, being grasped by first jaw 206, may be pulled along with suture material 212 through the tissue sections X, Y to be sutured, thus forming a stitch.

In order to return to an initial position and form a second stitch, a further depression of control lever 214 will advance cam rollers 366 and 378 between position C, C', and D, D' to advance second jaw 208 again about surgical needle 210 and further advance cam rollers 366, 378 between positions D, D' and E, E' to drive second jaw sleeve 230 distally thereby firmly grasping surgical needle 210 within notch 234 and second needle retaining arm 232. Thus, it can be seen after four complete depressions of control levers 214, 214a cam sleeve 344 has been rotated one full turn and returns surgical suturing apparatus 200 to the initial position of FIGS. 30, 31.

Figure 42:
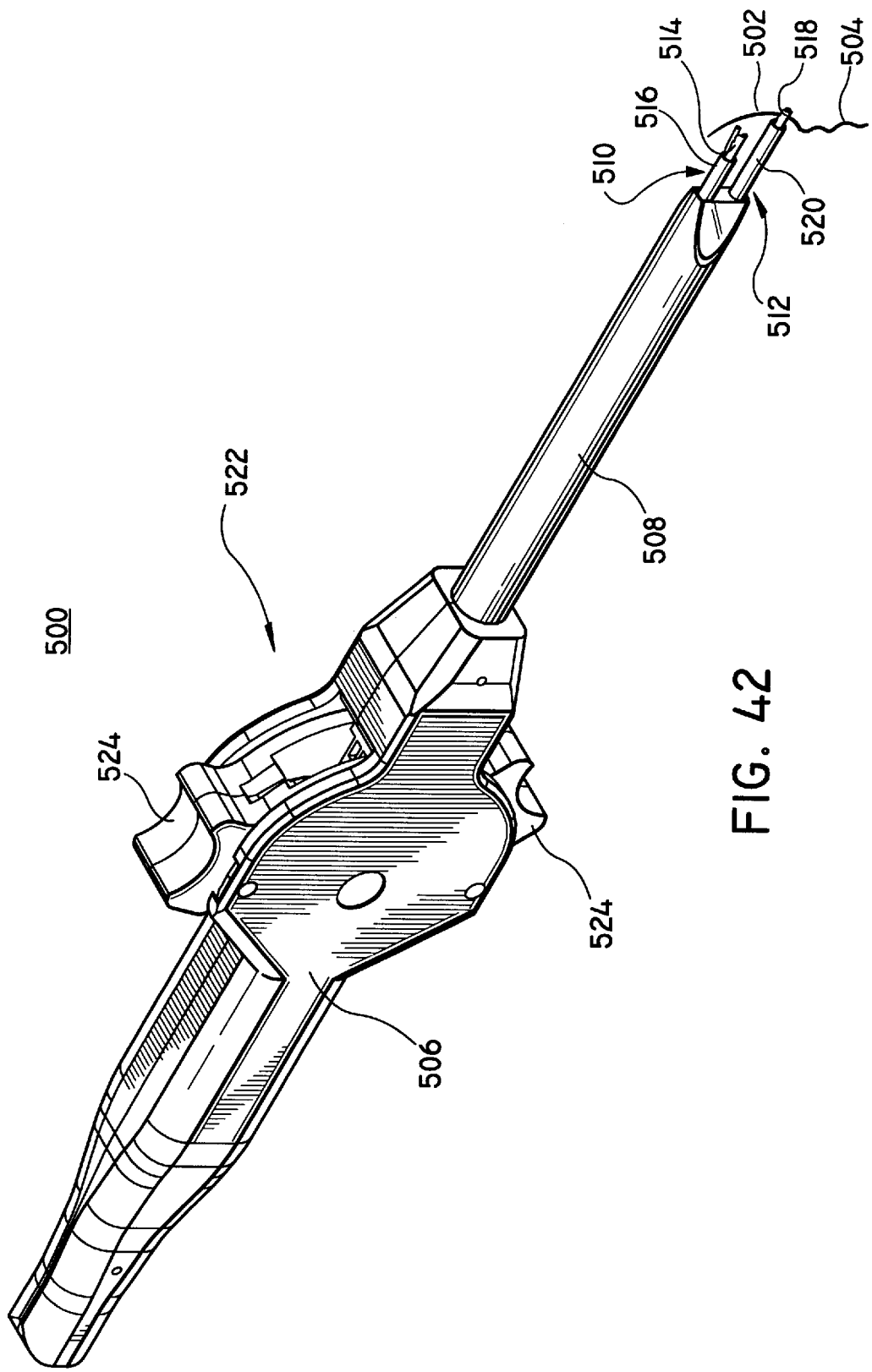
FIG. 42 is a perspective view of an alternate embodiment of a surgical suturing apparatus.

Referring now to FIG. 42, there is illustrated an alternate embodiment of a surgical suturing apparatus. Surgical suturing apparatus 500 is designed, like the above-described embodiments, to pass a surgical needle 502, having a length of suture 504 attached thereto, through tissue and between a pair of jaws. In this embodiment, needle 502 preferably is a rectangular bodied straight ski tip needle. Surgical suturing apparatus 500 generally includes a handle or housing 506 and an elongated tubular portion 508 extending distally from housing 506. Tubular portion 508 is dimensioned to fit within a conventional cannula structure, such as a cannula having an inner diameter of about 5 mm to about 12 mm.

First and second jaw assemblies 510 and 512, respectively, extend distally from tubular portion 508 and are partially contained therein. First and second jaw assemblies 510 and 512 are oriented parallel to a longitudinal axis of tubular portion 508 and are mounted for movement parallel to both the longitudinal axis of tubular portion 508 and to each other. First jaw assembly 510 includes a first jaw 514 configured to grasp a portion of surgical needle 502 and a first securing member or first sleeve 516 slidable about first jaw 514 to secure surgical needle 502 therein. Similarly, second jaw assembly 512 includes a second jaw 518 and a second sleeve 520 which function in similar manner. First and second sleeves 516 and 520 are movable parallel to the longitudinal axis of tubular portion 508 and each other and at least partially independently of the entire respective jaw assemblies 510 and 512. An actuation mechanism 522 including trigger 524 is provided to control the movements of jaw assemblies 510 and 512.

It should be noted that various components of surgical suturing apparatus 500 may be formed as complimentary halves to facilitate construction. Thus, for example, housing 506 may be formed as housing halves 506a and 506b. Similarly, trigger 524 may be formed as trigger halves 524a and 524b.

Referring now to FIG. 43, a single housing half 506b, for example, has been removed to illustrate various internal components associated with actuator mechanism 522. As noted above, trigger 524 is formed from complimentary halves 524a and 524b which are press fit or affixed together by suitable adhesive. Trigger half 524b includes a pair of thumb buttons 526b extending from opposed sides of housing 506 and joined by a central portion 528b. A pair of clearance grooves 530b are defined between thumb buttons 526b and central portion 528b to facilitate movement of a pair of pivoting control members relative to housing 506 in a manner described in more detail hereinbelow. Trigger half 524a is a mirror image of handle half 524b and its parts are designated by like numerals. Each trigger half 524a and 524b includes a mounting stud, for example, mounting stud 532b to pivotally mount trigger 524 within housing 506. Operation of trigger 524 reciprocates first and second drive bars 534 and 536 within housing 506 as described below. First and second drive bars 534 and 536 are connected to first and second jaw assemblies 510 and 512, respectively, and operate them in sequenced fashion in the manner described below.

Referring now to FIG. 44, each housing half 506a and 506b has a trigger mounting hole 538a and 538b for receipt of mounting studs 532a and 532b, respectively. In order to control and sequence the movement of drive bars 534 and 536 such that only one of the drive bars, and thus only one of the jaw assemblies associated therewith, are in operation at a time there are provided first and second control members 540 and 542, respectively, each pivotally mounted within housing 506. First control member 540 is formed with a first mounting bar 544. First mounting bar 544 is rotatably mounted within holes 546a and 546b formed in housing halves 506a and 506b. Similarly, second control member 542 is formed with a second mounting bar 548 and is rotatably mounted within holes 550a and 550b within housing halves 506a and 506b. Grooves 530a and 530b in trigger 524 provide clearance about first and second mounting bars 544 and 548.

In order to engage and move drive bar 534, first control member 540 includes a pair of arms 552 which straddle drive bar 534. Grooves 554 in arms 552 surround and engage a pair of drive studs 556 formed on drive bar 534. By pivoting control member 540 within housing 506, drive bar 534 is caused to reciprocate within housing 506. In like manner, control member 542 includes a pair of arms 558, having grooves 560, which straddle drive bar 536. Grooves 560 engage drive studs 562 on drive bar 536 to reciprocate drive bar 536 within housing 506.

Trigger 524 is formed with pairs of inwardly directed pins 564 and 566 to engage and pivot first control member 540 and second control member 542, respectively, as trigger 524 is actuated. First control member 540 includes grooves 568 to engage pins 564 and second control member 542 includes grooves 570 to engage pins 566. As noted hereinabove, it is desirable that only one drive bar, and thus only one jaw assembly, be actuated at a given moment. Thus, each of first and second control members 540 and 542 includes a land area of reduced cross-section surrounding grooves 568 and 570. Upon rotation of trigger 524 through a first arc pins 566 enter a reduced cross-sectional land area 572 of second control member 542 and are disengaged from slot 570. Conversely, when trigger 524 is actuated in an opposite direction through a second arc, pins 564 enter a reduced cross-sectional land area 574 of first control member 540 and are disengaged from slot 568. Thus, when trigger 524 is rotated through the first arc only first control member 540 is engaged with first drive bar 534 and second control member 542 is disengaged from second drive bar 536 and visa-versa.

Elongated tubular portion 508 includes a jaw guide 576 and an outer cover 578 positioned about jaw guide 576. Jaw guide 576 and cover 578 are affixed to housing 506 by a pin 580. First and second grooves 582 and 584 are formed in jaw guide 576. First jaw assembly 510 is slidably positioned within first groove 582 and second jaw assembly 512 is slidably positioned within second groove 584.

Figure 46A:
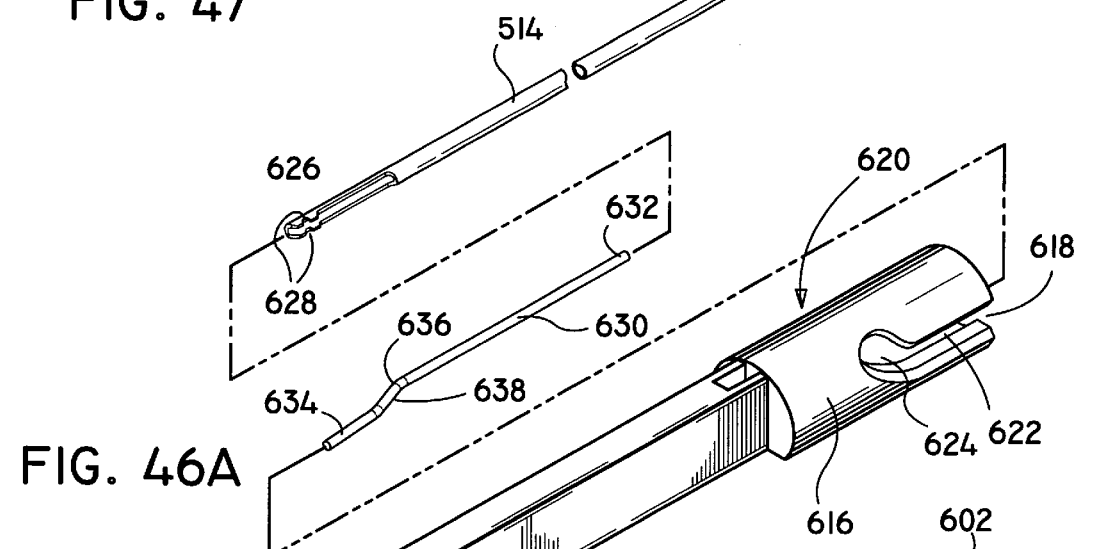
FIG. 46A is a perspective view of a jaw assembly and drive bar of the embodiment of FIG. 42 with parts separated.
Figure 46:
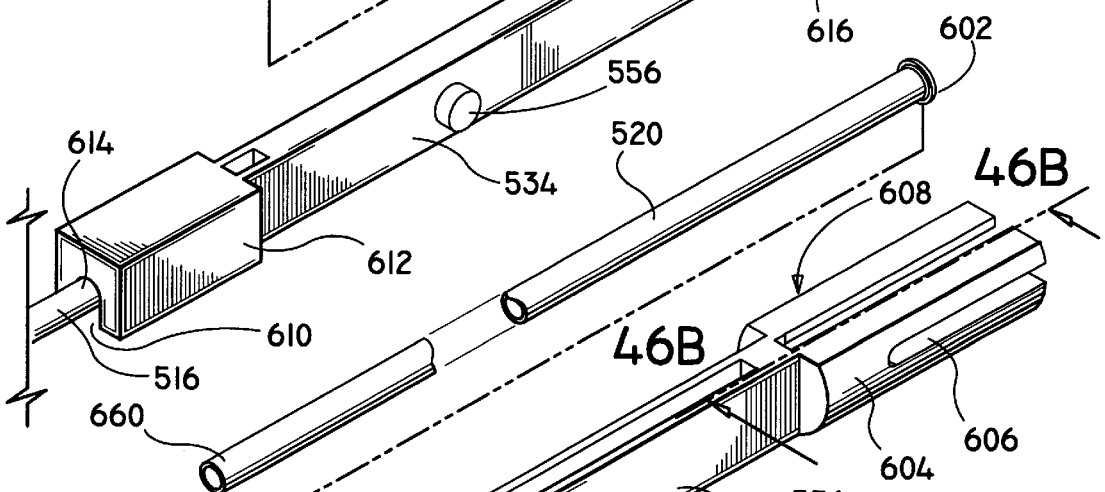
FIG. 46 is a perspective view of a drive bar and sleeve.
Figure 46B:
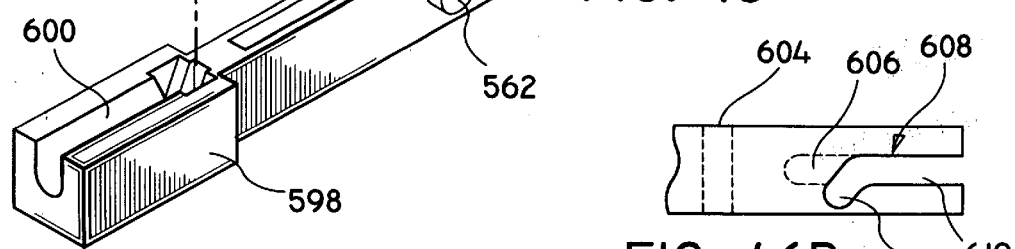
FIG. 46B is a sectional view taken along line 46B—46B of FIG. 46.
Figure 48:
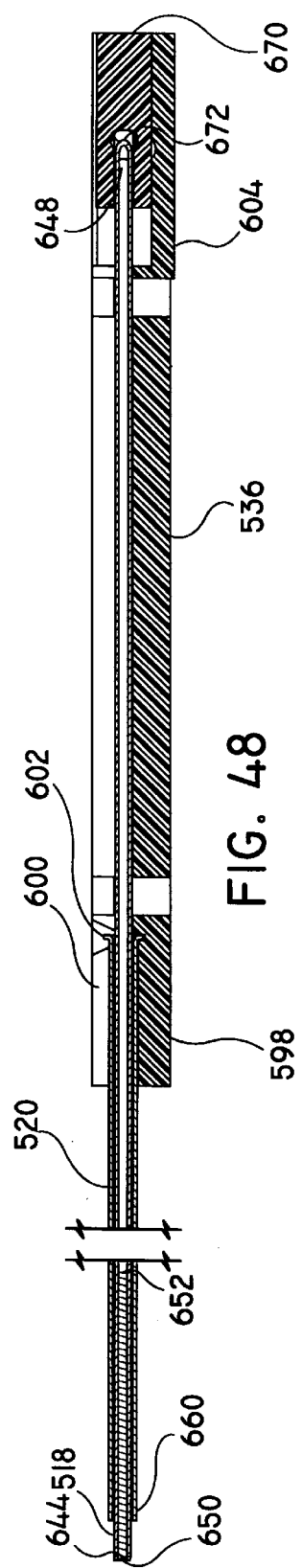
FIG. 48 is a sectional view taken along lines 48—48 of FIG. 44.

Referring now to FIGS. 46 and 46A, first and second drive bars 534 and 536 are illustrated in greater detail. Drive bars 534 and 536 provide the dual function of initially withdrawing an associated sleeve to release a surgical needle from a jaw, in a manner similar to sleeves 220 and 230 of jaws 206 and 208 of suturing apparatus 200 above (see FIG. 21A), and subsequently retracting the entire associated jaw assembly relative to tubular portion 508 and away from surgical needle 502.

Drive bar 536 includes a distal portion 598 having a notch 600 to receive and securely hold a flanged proximal end 602 of second sleeve 520. A proximal end 604 of drive bar 536 is hollow and has a slot 606 and a groove 608 (not shown) opposite slot 606, the functions of which are described below. Similarly, as shown in FIG. 46A, drive bar 534 has a notch 610 in a distal end 612 thereof to securely hold a proximal end 614 of sleeve 516. The proximal end 616 of drive bar 534 is also hollow and has a drive bar groove 618 and a longitudinal slot 620 (not shown) opposite drive bar groove 618. As shown, drive bar groove 618 has a straight portion 622 and an upwardly depending portion 624. Returning to FIG. 46, Groove 608 of drive bar 536 also has a straight portion and a downwardly depending portion (not shown).

As indicated above, first jaw 514 and second jaw 518 are provided to releasably hold surgical needle 502. Thus, as shown in FIG. 46A, first jaw 514 includes a distal end 626 having a channel-shaped cross-section. A notch 628 is provided in distal end 626 to receive a portion of surgical needle 502. A flexible finger 630 is provided and has a proximal end 632 insertable within jaw 514 and a distal end 634 to hold surgical needle 502 within notch 628. Flexible finger 630 is formed with a bend 636 adjacent distal end 634. Bend 636 provides a camming surface 638 for engagement with the distal end of first sleeve 516. A proximal end 640 of first jaw 514 is preferably L-shaped. Similarly, while not specifically illustrated, second jaw 518 includes a distal end having a channel shaped cross-section with a notch defined therein and an L-shaped proximal end. A second flexible finger is provided having a proximal end insertable within the second jaw and a distal end having a flexible finger formed with a bend defining a camming surface engageable with a distal end of second sleeve 520 to bias the distal end of the second flexible finger into engagement with surgical needle 502 to hold the needle.

Figure 47:
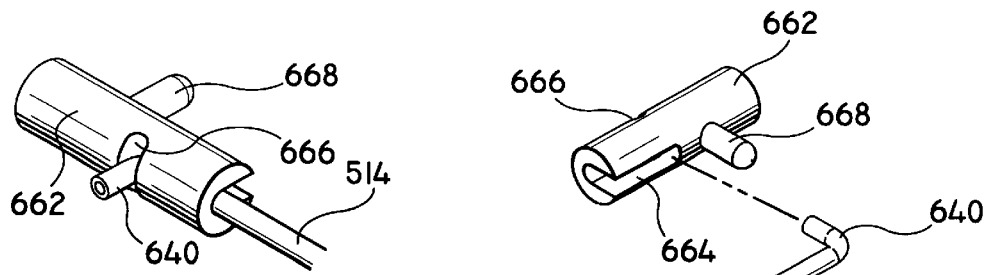
FIG. 47 is a perspective view of a proximal end of a jaw member positioned within a drive sleeve.

As shown in FIG. 46A, the jaw members extend through the respective sleeves and drive bars. Referring to FIGS. 46A and 47, a first drive sleeve 662 is provided to control the relative motion of first sleeve 516 relative to jaw 514, such that initial retraction of first drive bar 534 retracts first sleeve 516 to release surgical needle 502 from first jaw 514 and further retraction of first drive bar 534 moves first jaw 514 and first sleeve 516 proximally away from surgical needle 502 to facilitate suturing. Additionally, first drive sleeve 662 controls the reverse motions of initially moving first jaw 514 and first sleeve 516 toward needle 502 and subsequently moving first sleeve 516 about first jaw 514 and first flexible finger 630 to secure surgical needle 502 therebetween.

Figure 50:
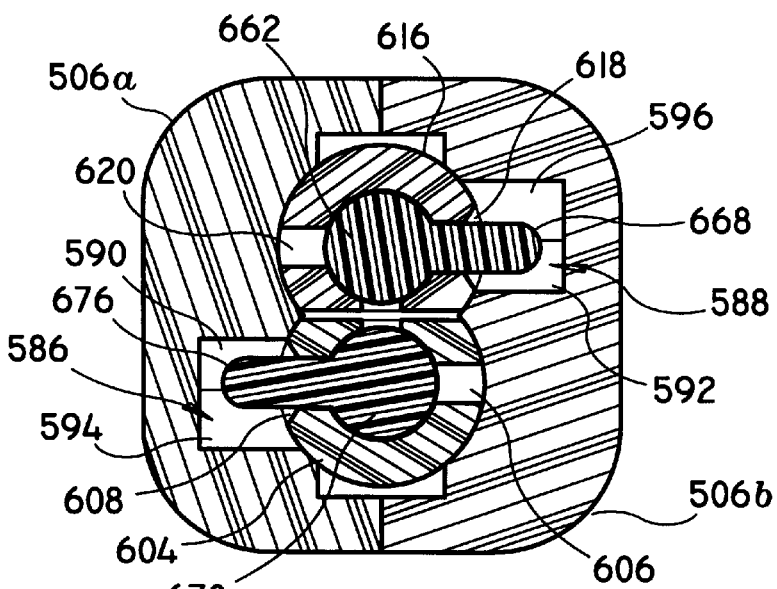
FIG. 50 is a sectional view taken along line 50—50 of FIG. 49.

More specifically, first drive sleeve 662 includes a longitudinally extending elongate slot 664 for receipt of proximal end 640 of first jaw 514. Proximal end 640 passes through elongate slot 664 and out a perpendicular slot 666 on the opposite side of the drive sleeve. Perpendicular slot 666 allows first drive sleeve 662 to rotate about proximal end 640 of first jaw 514 without rotating first jaw 514. Referring to FIGS. 46A and 50, straight slot 620 in the proximal end of drive bar 534 slidingly receives proximal end 640 of first jaw 514 which protrudes through slot 666. Thus, the interaction of proximal end 640 and slot 620 allows first jaw 514 to move longitudinally with respect to drive bar 534 while being restrained against rotation. First drive sleeve 662 also includes a guide pin 668 projecting from a side thereof. Guide pin 668 is dimensioned to ride within drive bar groove 618 in proximal end 616 of first drive bar 534 and extends through and protrudes beyond drive bar groove 618.

Similarly, a second drive sleeve 670 is provided and is positioned within proximal end 604 of drive bar 536 as shown in FIGS. 46–50. Second drive sleeve 670 includes an elongate slot 672 and a perpendicular slot to receive the proximal end of second jaw 518 in similar fashion. The protruding end of second jaw 518 rides in slot 606 of drive bar 536, thereby permitting longitudinal but not rotational motion of jaw 518 (see FIG. 46). Additionally, second drive sleeve 670 includes a projecting guide pin 676 dimensioned to ride within groove 608 in proximal end 604 of second drive bar 536 in a manner similar to guide pin 668 in drive bar groove 618 (see FIGS. 46 and 50).

Figure 45A:
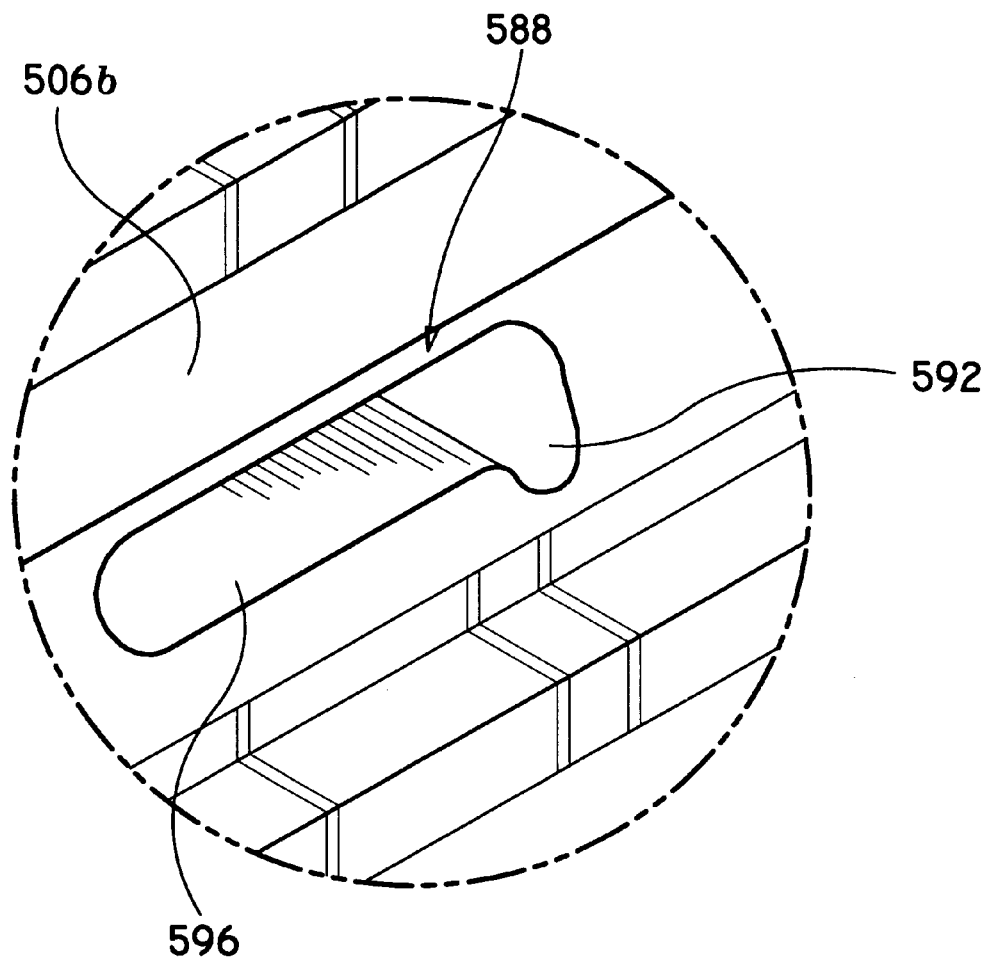
FIG. 45A is an enlarged isolation view of a cam slot in the housing half 506b.

Referring now to FIGS. 44, 45 and 45A, each housing half 506a and 506b is provided with a jaw-block groove 586 and 588, respectively, formed within the associated housing half. Jaw block grooves 586 and 588, together with drive sleeves 662, 670, and the slots in the proximal portions of drive bars 534, 536, function to maintain first and second jaws 514 and 518 initially in a distal or extended position as respective jaw sleeves 516 and 520 are initially retracted by drive bars 534, 536 to release surgical needle 502 and also control the sequence of operation in the opposite direction. Each jaw block groove 586, 588 has a depending portion 590 and 592 to receive guide pins 668, 676, thereby holding associated jaws 514, 518 distally as the associated first and second jaw sleeves 516 and 520 are moved proximally. Jaw block groove 586 is formed with depending portion 590 in a generally upward orientation as illustrated in FIGS. 44 and 45. Jaw block groove 588 in housing half 506b has depending portion 592 at a distal end of straight portion 596 and oriented in a generally downward orientation as shown in FIG. 45A. Depending portions 590, 592 are inversely aligned with the corresponding depending portions of the grooves in the proximal portions of drive bars 534, 536. By way of example, and with reference to FIG. 46A, drive bar groove 618 is aligned with jaw block groove 588 in housing half 506b (shown in FIG. 45A), and guide pin 668 extends through drive bar groove 618 into jaw block groove 588 of housing half 506b. The interaction of the guide pins on the drive sleeves with the drive bar grooves and jaw block grooves as the drive bars move in response to pressure on the trigger controls the sequence of movement of the sleeves to release and capture the needle in the jaws and the retraction and advancement of the jaw assemblies.

For example, when drive bar 534 is in its distal-most position sleeve 516 cams flexible finger 630 closed to hold needle 502 in jaw 514. In this position, guide pin 668 is disposed in a proximal position within the straight portion 622 of drive bar groove 618 and extends into the downwardly depending portion 592 of the jaw block groove 588 of housing half 506b. As drive bar 534 moves proximally in response to pressure on the trigger, sleeve 516 is retracted proximally to release flexible finger 630 and needle 502 may be released from jaw 514. However, during initial movement of drive bar 534 in a proximal direction guide pin 668 is held stationary against longitudinal movement in downwardly depending portion 592 in jaw block groove 588, thereby holding jaw 514 stationary as sleeve 516 retracts. As drive bar 534 initially moves proximally to retract sleeve 516, the straight portion 622 of drive bar groove 618 moves proximally relative to stationary guide pin 668. After sleeve 516 retracts to release the needle from the jaw, upwardly depending portion 624 of drive bar groove 618 cams guide pin 668 upwardly out of downwardly depending portion 592 of jaw block groove 588 into the straight portion 596 of jaw block groove 588. As guide pin 668 is cammed upwardly, the drive sleeve rotates from the position shown in FIG. 50 to the position shown in FIG. 57. Thereafter, as drive bar 534 continues to move proximally it simultaneously draws sleeve 516 and jaw 514 proximally and away from needle 502, with guide pin 668 moving proximally in straight portion 596 of jaw block groove 588. Similarly, projecting guide pin 676 of second drive sleeve 670 is held in upwardly depending portion 590 of jaw block groove 586 in housing half 506a (see FIGS. 44, 45 and 50) as drive bar 536 initially moves proximally to retract sleeve 520 and release the needle from jaw 518. After the needle is released from jaw 518, guide pin 676 is cammed downward out of upwardly depending portion 590 of jaw block groove 586 by a downwardly depending portion of groove 608 in the proximal end of drive bar 536, thereafter permitting drive sleeve 670 and, hence, jaw 518 to be withdrawn proximally with sleeve 520 and away from needle 502.

Thus, once sleeve 516 or 520 has moved proximally to release a surgical needle from the associated jaw, guide pins 668, 676 are permitted to enter and move in longitudinal portions 594, 596 of jaw block grooves 586 and 588 and allow the associated entire jaw assembly 510, 512 to be retracted proximally away from surgical needle 502 with sleeve 516, 520, respectively.

Figure 49:
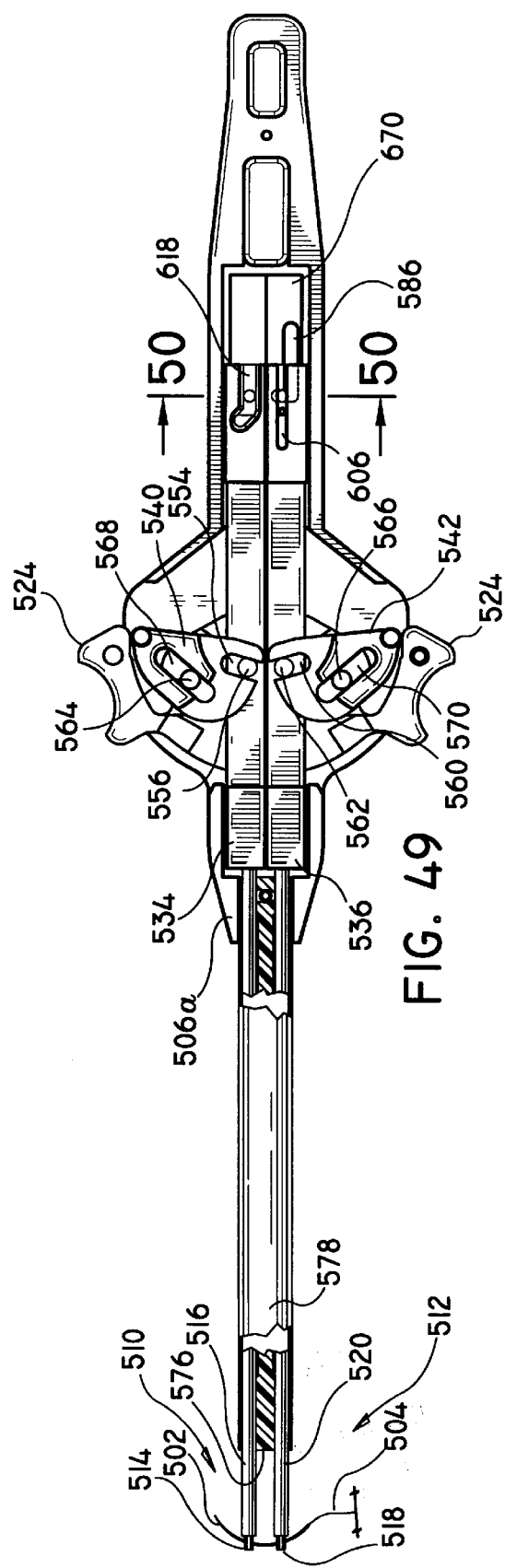
FIG. 49 is a side plan view, partially shown in section, of the embodiment of FIG. 42.

Referring now to FIGS. 49–64, the operation of surgical suturing apparatus 500 to pass surgical needle 502 through a pair of tissue sections will now be described. As shown in FIG. 49, in an initial position, triggers 524 are positioned in a central position corresponding to equal positions of first and second jaw assemblies 510 and 512. First and second drive bars 534 and 536 are in a distal position within housing 506 and surgical needle 502 is secured within first and second jaws 514 and 518 by first and second sleeves 516 and 520, respectively. As shown, first and second control members 540 and 542 are positioned such that grooves 554 and 560 surround drive studs 556, 562 on first and second drive bars 534, 536 respectively. It should be noted that pins 564 and 566 of triggers 524 are positioned within grooves 568, 570, respectively.

Referring now to FIG. 50, guide pin 668 of first drive sleeve 662 resides in downwardly depending portion 592 of jaw block groove 588 and is thus restrained against longitudinal movement with respect to housing half 506b. In this position, guide pin 668 is in straight portion 622 of drive bar groove 618 formed in proximal end 616 of drive bar 534. Similarly, guide pin 676 of drive sleeve 670 resides in upwardly depending portion 590 of jaw block groove 586 and is blocked from longitudinal movement therein. Guide pin 676 is in straight portion 619 of groove 608 formed in proximal end 604 of drive bar 536.

Figure 51:
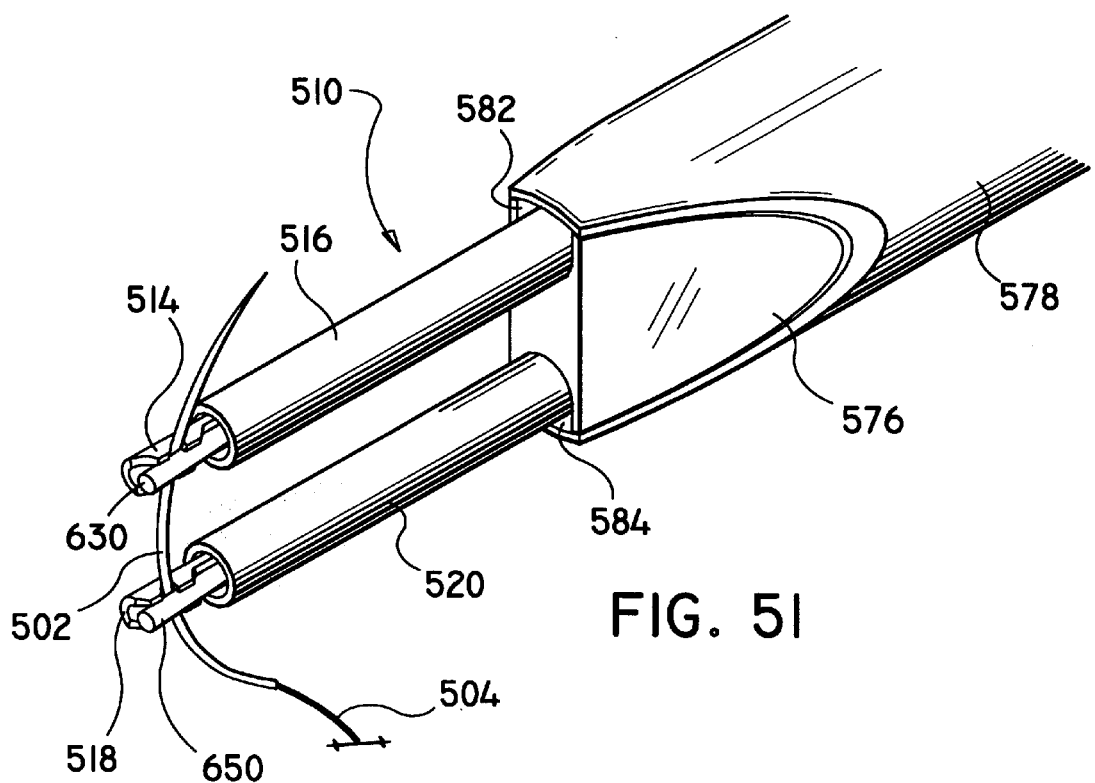
FIG. 51 is an enlarged perspective view of the distal end of the embodiment of FIG. 42 showing a surgical needle held within two jaw assemblies.

As best seen in FIG. 51, in the initial position, surgical needle 502 is secured within first and second jaws 514, 518 by flexible fingers 630, 650 respectively. As shown, sleeves 516 and 520 are in their distalmost position to firmly secure and retain surgical needle 502 within first and second jaws 514, 518.

In order to initiate suturing with surgical suturing apparatus 500 and surgical needle 502 such that a surgical needle 502 can penetrate tissue sections, for example, tissue sections A and B, it is necessary to retract first jaw assembly 510 including first jaw 514 and first sleeve 516 proximally away from the surgical needle, as shown in FIG. 52.

Referring now to FIG. 53, in order to actuate surgical suturing apparatus 500, triggers 524 are initially pivoted clockwise, as shown in FIG. 53. As triggers 524 are rotated in a clockwise direction, pin 564 engages groove 568 of first control member 540. As trigger 524 is rotated clockwise, pin 564 forces first control member 540 to rotate counterclockwise about first mounting bar 544. As first control member 540 is rotated counterclockwise about first mounting bar 544, arms 552 force drive stud 556 on first drive bar 534 in a proximal direction to move first drive bar 534 proximally. As drive bar 534 is initially moved proximally, straight portion 622 of drive bar groove 618 in the proximal end of drive bar 534 moves proximally relative to stationary guide pin 668 such that only sleeve 516 affixed to drive bar 534 is retracted. At this point, guide pin 668 still resides in depending portion 592 of jaw block groove 588 in housing half 506b and is blocked from longitudinal movement. Thus, first jaw 514 does not move.

Figure 54:
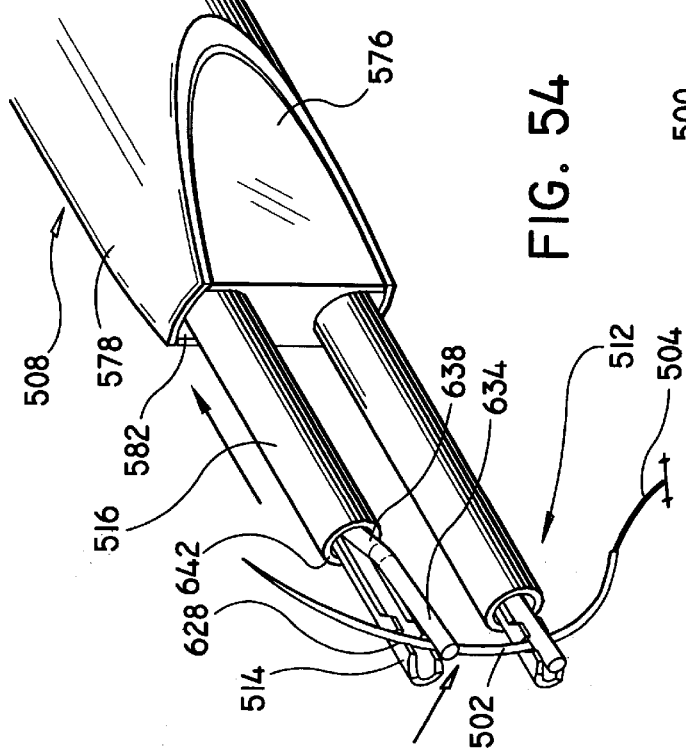
FIG. 54 is an enlarged perspective view of the distal end of the embodiment of FIG. 42 corresponding to FIG. 53 showing retraction of a first sleeve to release the surgical needle from the first jaw.

As best shown in FIG. 54, as sleeve 516 is retracted in a proximal direction parallel to a longitudinal axis of elongated tubular portion 508, the distal end 642 of sleeve 516 moves away from camming surface 638 on flexible finger 630. Distal end 634 of flexible finger 630 is thus biased outward away from first jaw 514 to release surgical needle 502 from notch 628 in first jaw 514. It will be noted that once surgical needle 502 is released from the grasp of first jaw 514 it is desirable and, perhaps, necessary to move sleeve 516 and first jaw 514, along with first flexible finger 630, proximally away from surgical needle 502 to facilitate use of surgical needle 502 to penetrate tissue.

Figure 55:
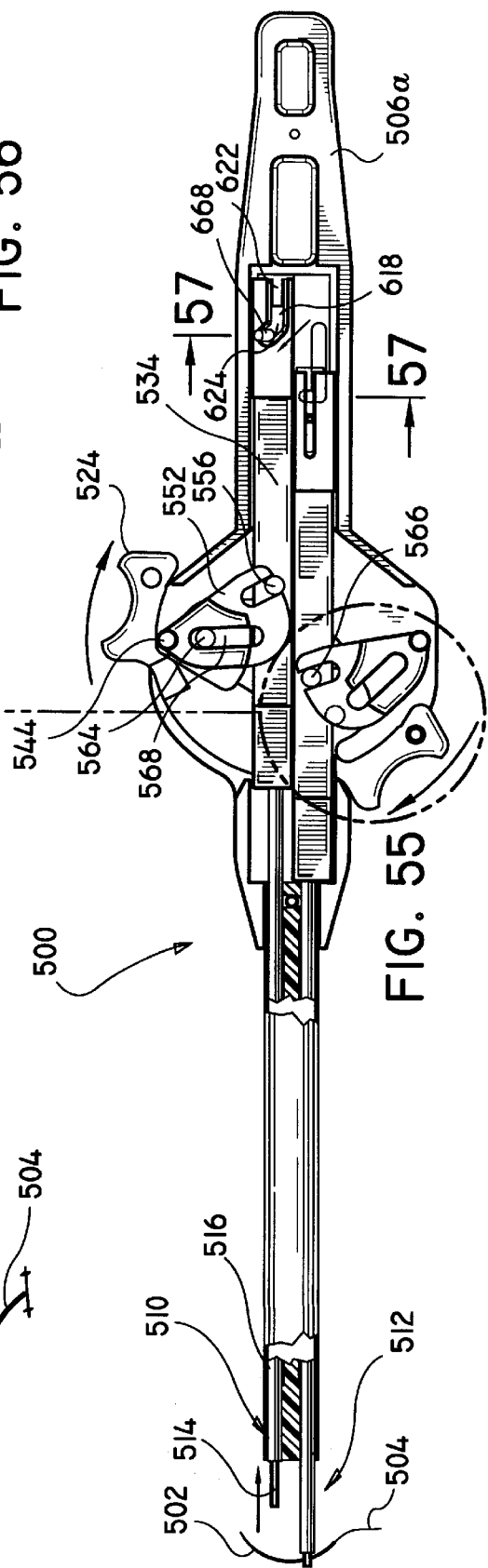
FIG. 55 is a view similar to FIG. 53 showing actuation to retract the first jaw assembly.

Referring now to FIG. 55, as triggers 524 continue to be rotated clockwise, first control member 540 including arms 552 continues to move drive stud 556 on drive bar 534 proximally. As drive bar 534 is moved proximally, guide pin 668 enters upwardly depending portion 624 of drive bar groove 618 and is moved upwardly within depending portion 624. As guide pin 668 moves upwardly in depending portion 624, guide pin 668 is forced upward and out of downwardly depending portion 592 of jaw block groove 588 formed in housing half 506b (not shown). Thus, guide pin 668 is moved into longitudinal portion 596 of jaw block groove 588. As will be appreciated, drive sleeve 662 rotates as guide pin 668 is cammed upward.

Figure 57:
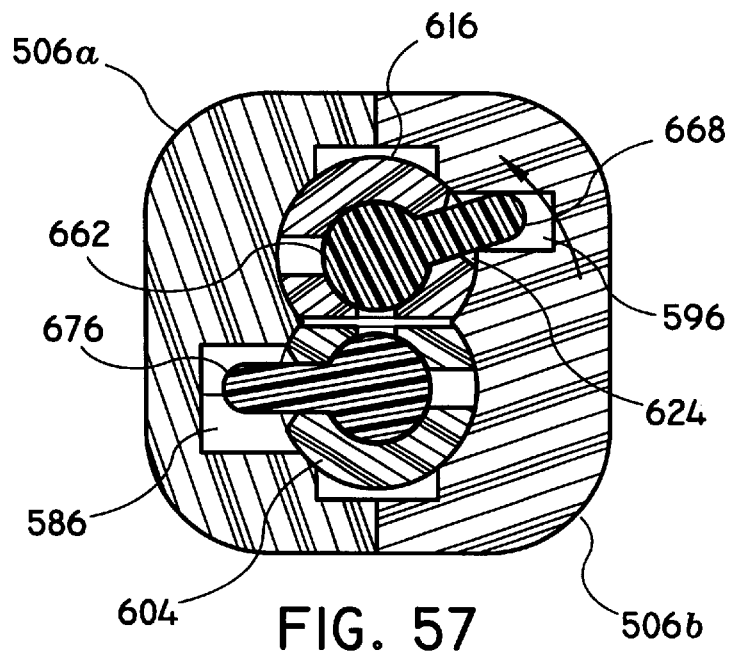
FIG. 57 is a sectional view taken along line 57—57 of FIG. 55.
Figure 58:
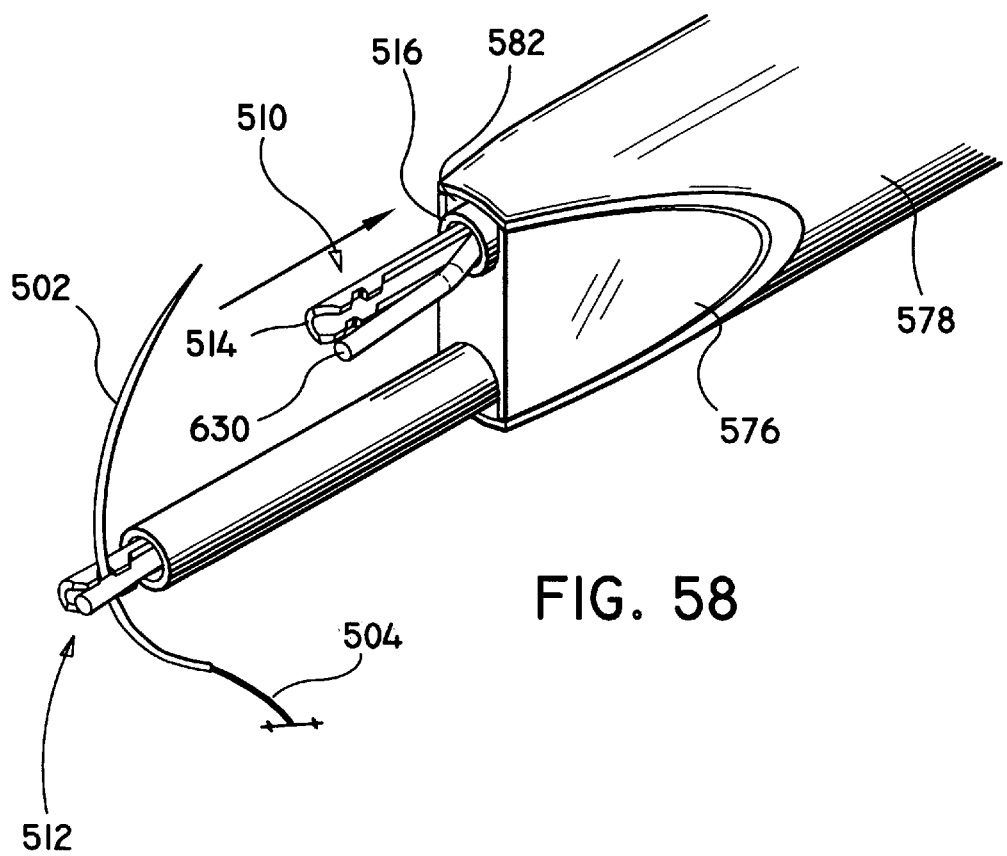
FIG. 58 is a view similar to FIG. 54 showing retraction of the first jaw assembly.

Referring for the moment to FIG. 57, as guide pin 668 moves upwardly within downwardly depending portion 592 of jaw block groove 588 in housing half 506b it enters longitudinal portion 596 of jaw block groove 588 and is no longer blocked against longitudinal movement by depending portion 590 of jaw block groove 588. Thus, guide pin 668 enters longitudinal portion 596 of jaw block groove 588 and is free to move proximally therein to draw first jaw assembly 510 away from surgical needle 502. Specifically, as first guide pin 668 and thus first drive sleeve 662 move proximally as drive bar 534 continues to move proximally, drive bar 534 draws both first sleeve 516 and first jaw 514, including first flexible finger 630, proximally away from surgical needle 502. This is best illustrated in FIG. 58, where it can be seen that first jaw assembly 510 including sleeve 516, first jaw 514, and first flexible finger 630 have been retracted to a proximal most position away from surgical needle 502.

Figure 56:
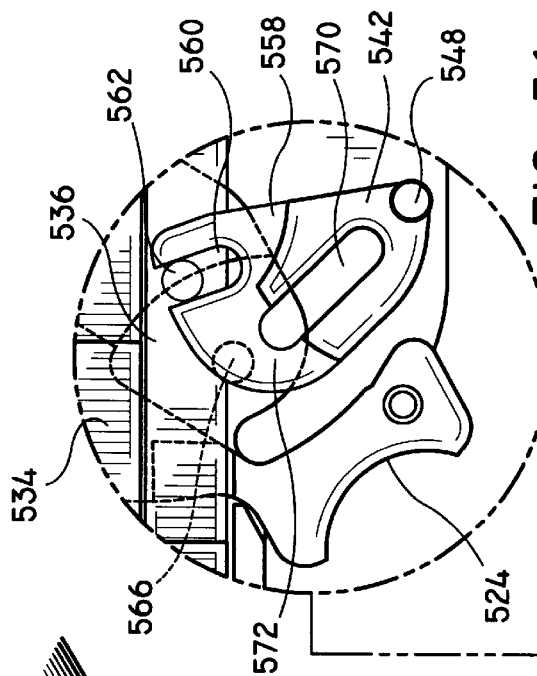
FIG. 56 is an enlarged isolation view, of an area of detail of FIG. 55.

Referring for the moment to FIGS. 55 and 56, it should be noted that as triggers 524 are rotated clockwise, drive bar 536 does not move. As triggers 524 are rotated clockwise, pins 566 on triggers 524 move into reduced cross-sectional area 572 of second control member 542 and are disengaged from slot 570. Therefore pin 566 is incapable of engaging and moving against groove 570. Thus, second control member 542 is not moved or pivoted about second mounting bar 548. Since second control member 542 does not move, drive bar 536 does not move and needle 502 remains held in jaw 518.

Figure 59:
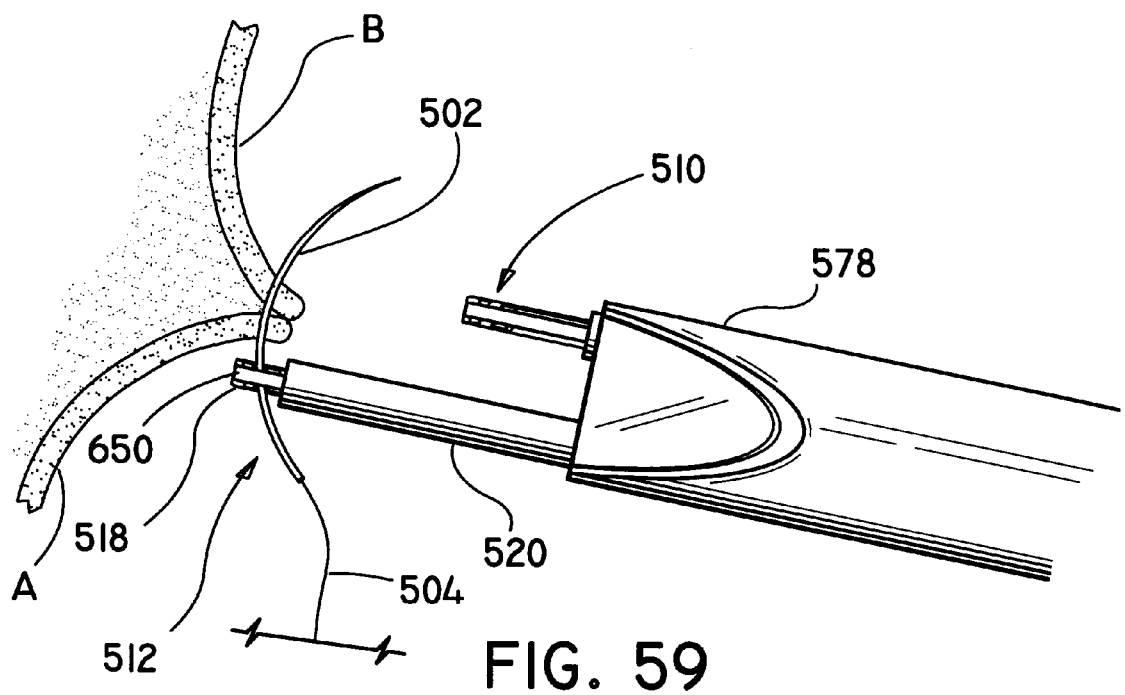
FIG. 59 is a view similar to FIG. 52 showing the surgical needle inserted through tissue and in position to be regrasped by the first jaw.

Referring now to FIG. 59, surgical needle 502 secured within second jaw assembly 512 is manipulated to pierce a first tissue section A and a second tissue section B as illustrated.

Figure 60:
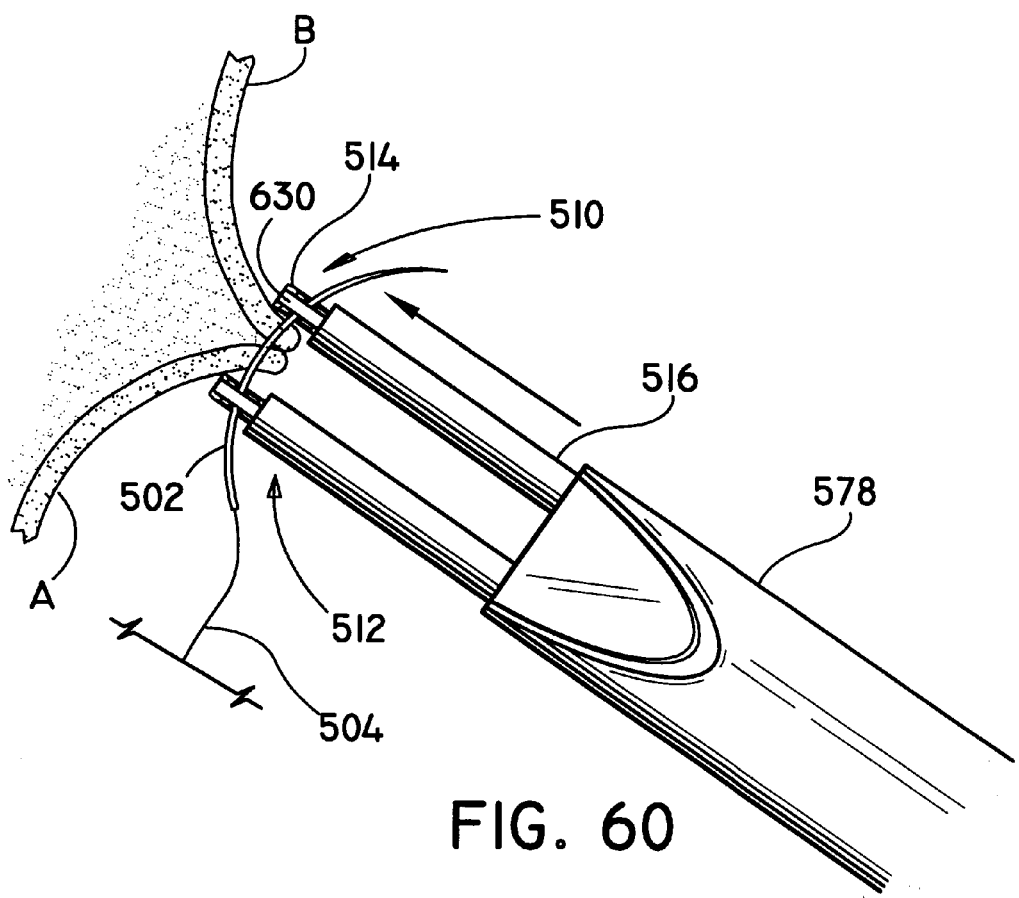
FIG. 60 is a view similar to FIG. 59 showing the first jaw regrasping the surgical needle.

Referring now to FIG. 60, the above-described process for retracting first jaw assembly 510 to initially release surgical needle 502 from first jaw 514 and subsequently retract the entire first jaw assembly 510 away from the surgical needle 502 is reversed such that triggers 524 are returned to a central position (FIG. 49). As triggers 524 are rotated counterclockwise to the central position, the above-described functions of the various components are performed in reverse order to initially advance first jaw assembly 510 about surgical needle 502 and subsequently advance first sleeve 516 about first flexible finger 630 and first jaw 514 to securely grasp surgical needle 502 within first jaw assembly 510 as shown in FIG. 60.

Figure 62:
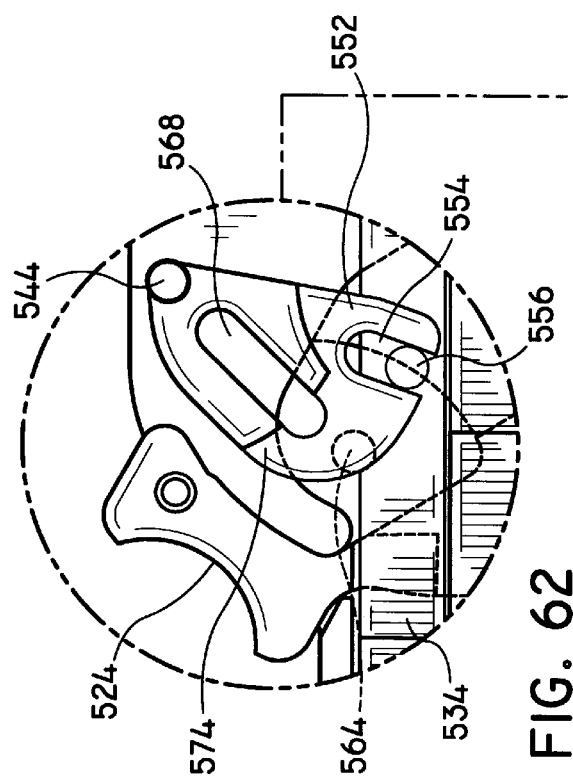
FIG. 62 is an enlarged isolation view showing an area of detail of FIG. 61.
Figure 61:
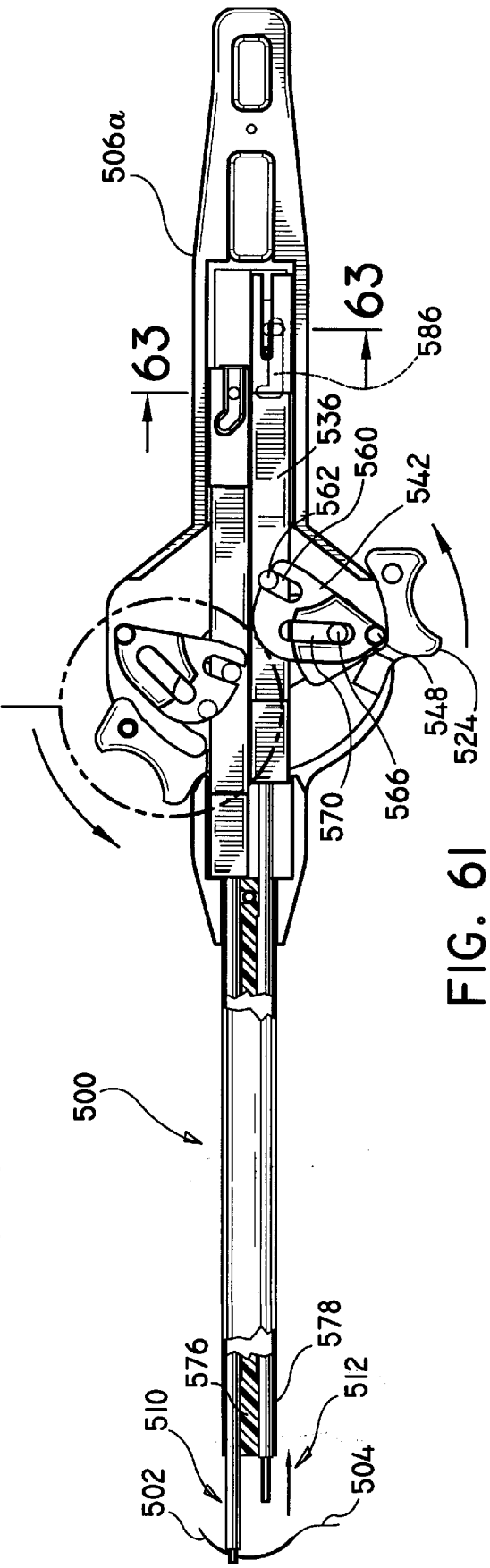
FIG. 61 is a view similar to FIG. 55 showing actuation in an opposite direction to release the surgical needle from the second jaw and retraction of the second jaw away from the surgical needle.

Referring now to FIG. 61, in order to complete the process and pull surgical needle 502 through tissue sections A and B without interference from jaw assembly 512, triggers 524 are rotated from their central position counterclockwise such that second drive bar 536 initially withdraws second sleeve 520 away from second jaw 518 and second flexible finger 650. Referring for the moment to FIG. 62, when triggers 524 are rotated counterclockwise from a central position, pin 564 of triggers 524 enters reduced cross sectional area 574 of first control member 540 and is disengaged from slot 568. Thus, drive bar 534 and first jaw assembly 510 do not move, and remain in the distal-most position gripping needle 502.

Figure 63:
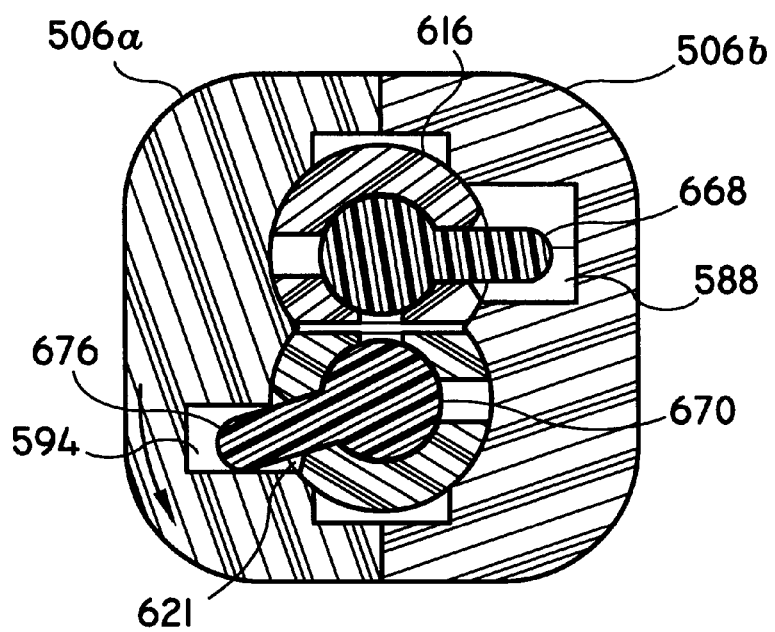
FIG. 63 is a sectional view taken along line 63—63 of FIG. 61.

As shown in FIG. 63, as triggers 524 are rotated counterclockwise, straight portion 619 of groove 608 in second drive bar 536 moves longitudinally with respect to guide pin 676 to withdraw sleeve 520 and release surgical needle 502 from second jaw assembly 512 without retracting jaw assembly 512. Subsequently, guide pin 676 is cammed within downwardly depending portion 621 of the second drive bar groove such that guide pin 676 moves out of upwardly depending portion 590 of jaw block groove 586 in housing half 506a and enters longitudinal portion 594 of jaw block groove 586. Thus, guide pin 676 of second drive sleeve 670 thereafter is free to move proximally within straight portion 594 of jaw block groove 586 so that drive bar 536 can retract the entire second jaw assembly 512 away from surgical needle 502.

Figure 64:
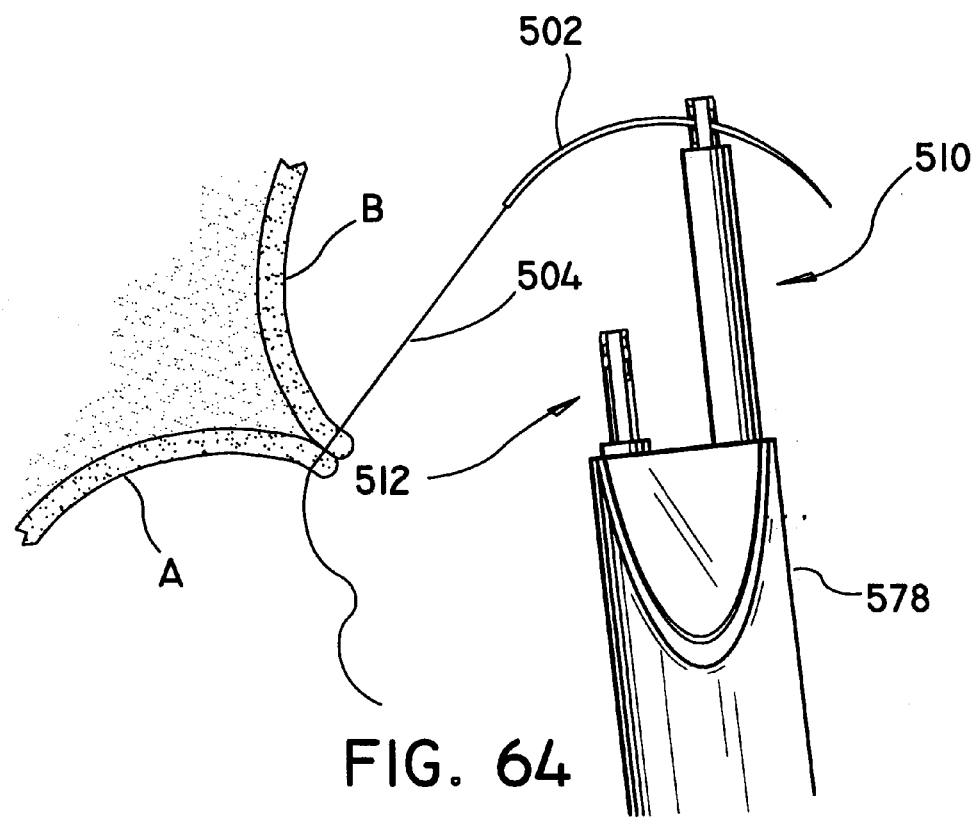
FIG. 64 is a view similar to FIG. 60 showing the surgical needle released from the second jaw and drawn through the tissue, along with a length of suture, by the first jaw.

Referring now to FIG. 64, when second jaw assembly 512 has been fully retracted proximally away from surgical needle 502, surgical needle 502 firmly grasped within first jaw assembly 510 may be pulled through tissue sections A and B thereby drawing suture 504 through tissue sections A and B to form a stitch.

It should be noted that upon movement of triggers 524 again clockwise to a central position second jaw assembly 512 will be advanced toward surgical needle 502 initially surrounding surgical needle 502 with second jaw 518 and second flexible finger 650 and subsequently advancing second sleeve 520 to cause the second jaw assembly to grasp surgical needle 502 and return surgical needle 502 and suturing apparatus 500 to the initial position of FIG. 49.

Figure 65:
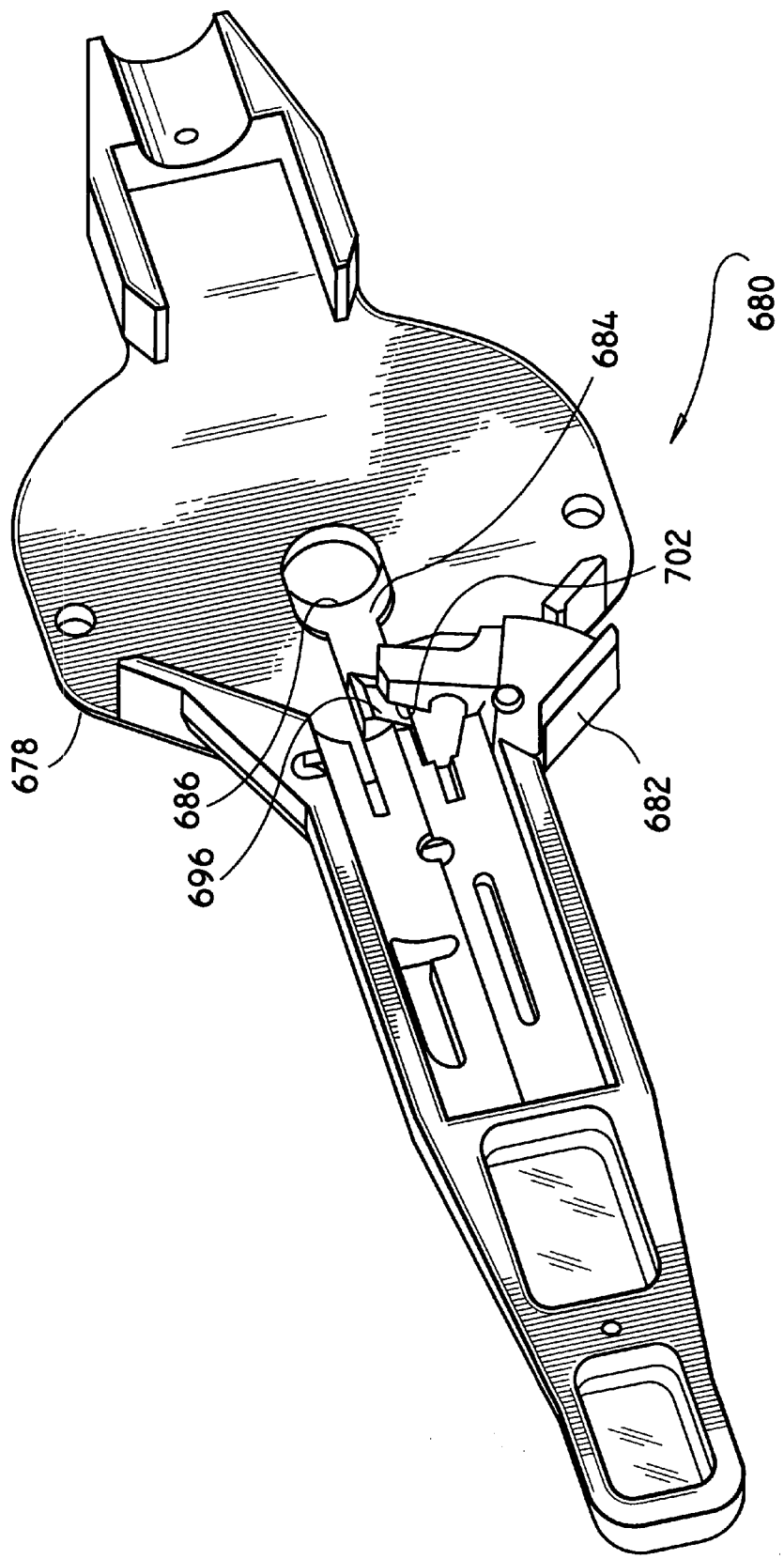
FIG. 65 is a perspective view of an alternative housing half incorporating a loading mechanism.

Referring now to FIGS. 65–68 and initially to FIG. 65, there is disclosed an alternate housing structure for use with surgical suturing apparatus 500. The alternate housing structure incorporates loading structure which allows both sleeves 516, 520 to be retracted without rotating trigger 524 from the central position. The loading structure allows loading of a surgical needle by hand or from a disposable loading unit or the like.

Housing 678 includes a loading mechanism 680 generally having a loading trigger 682 pivotally mounted on housing 678 and a release lever 684 mounted on housing 678. Release lever 684 includes an arcuate distal edge 686 to engage and release mounting stud 532 on trigger 524 (FIG. 45).

Figure 66:
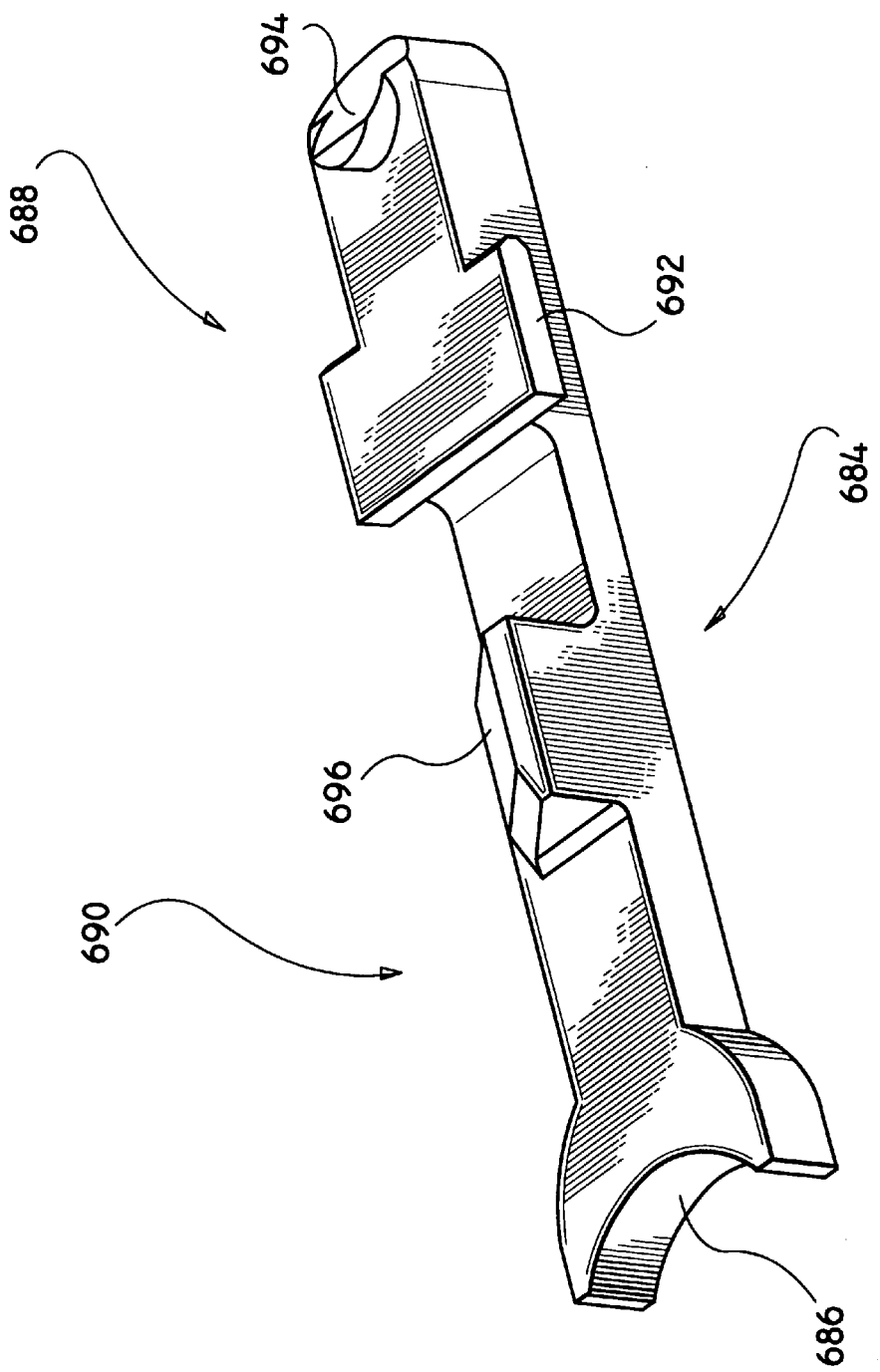
FIG. 66 is a perspective view of a release lever associated with the loading mechanism of FIG. 65.

Referring now to FIG. 66, release lever 684 is configured to be mounted to housing 678 such that a proximal end 688 of release lever 684 is firmly fixed within housing 678 while a distal end 690 is free to flex out of the plane of housing 678. Proximal end 688 of release lever 684 includes a flange 692 and a mounting stud 694 which engage corresponding structure on housing 678 to secure release lever thereon. Release lever 684 further includes a camming surface 696 projecting from a side of release lever 684 to flex arcuate distal edge 686 away from housing 678.

Figure 67:
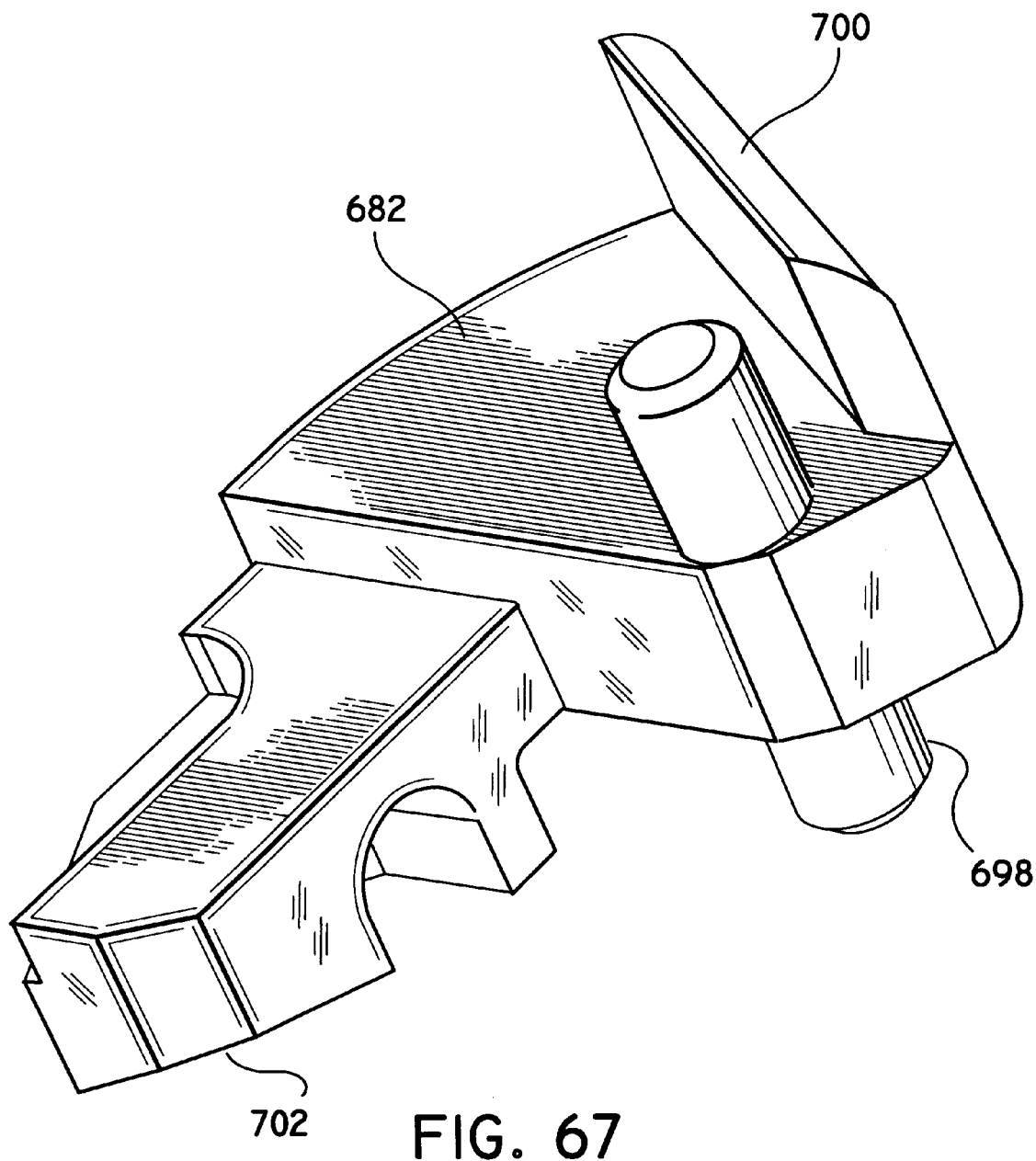
FIG. 67 is a perspective view of a loading trigger associated with the loading mechanism of FIG. 65.

As shown in FIG. 67, loading trigger 682 includes a mounting bar 698 which pivotally mounts trigger 682 to housing 678. Loading trigger 682 also includes a thumbpiece 700 engageable by the user and a camming surface 702 engageable with camming surface 696 of release lever 684.

Figure 68:
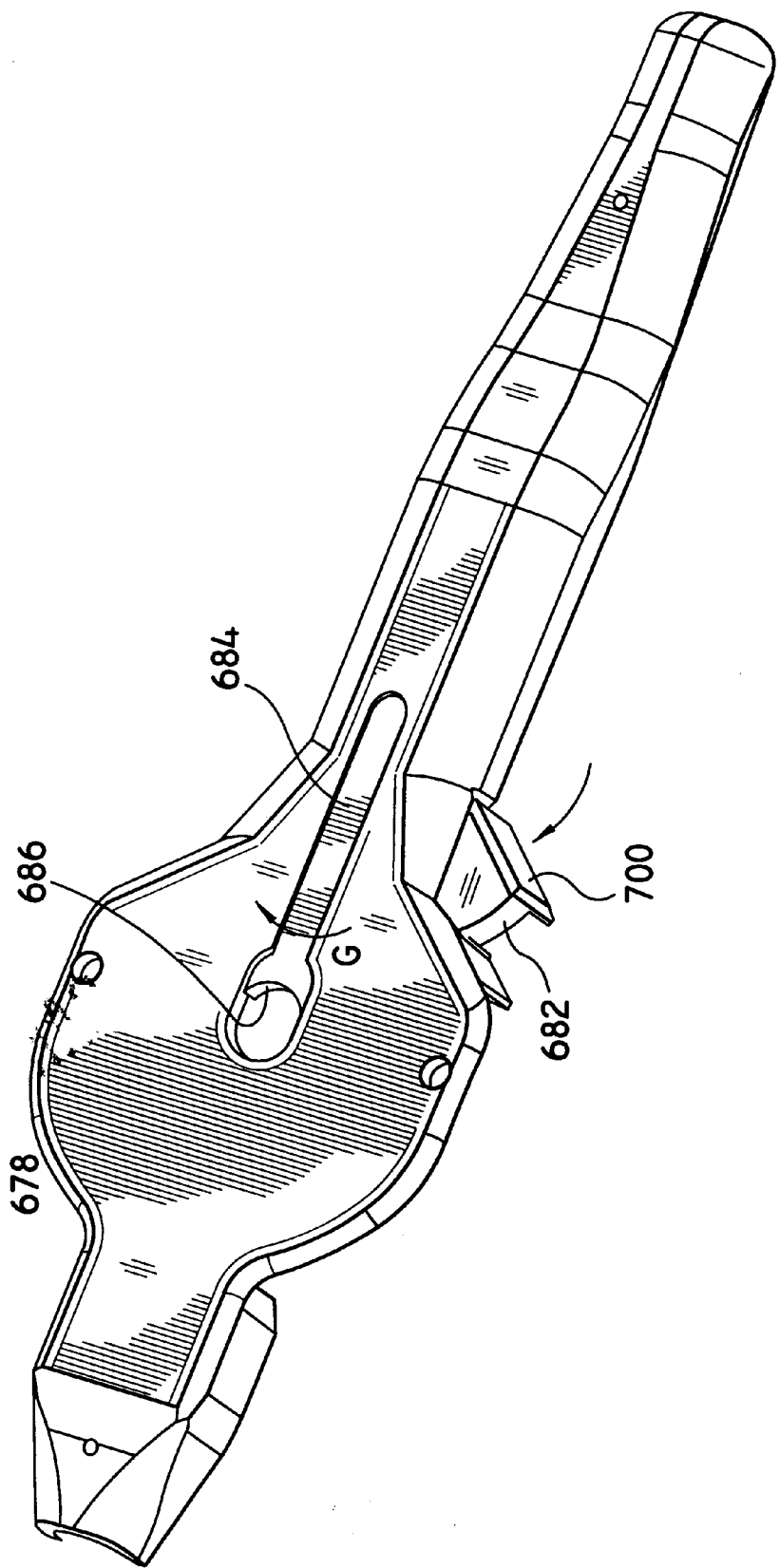
FIG. 68 is a perspective view of the outside of the housing half of FIG. 65.

Referring now to FIGS. 65 and 68, operation of loading mechanism 680 will now be described. It should be noted that both housing halves of a suturing apparatus need be provided with a loading mechanism 680 to enable both mounting studs 532 of trigger 524 to be disengaged from housing 678. With the trigger in the central position (FIG. 49) loading trigger 682 is depressed to pivot about mounting bar 698 and cause camming surface 702 to engage camming surface 696 of release lever 684. Distal end 690 of release lever 684 is thus moved out of the plane of housing 678 causing arcuate distal edge to be disengaged from mounting studs 532 of trigger 524. Trigger 524 may then be pulled proximally to draw both sleeves 516, 520 away from first and second jaws 514, 518 to allow release or loading of a surgical needle. Preferably, the trigger and/or associate structure is spring-biased in a distal direction to urge the mechanism distally so that studs 532 re-engage distal edge 686 to return the apparatus to operating condition.

It should also be understood that the several apparatus described herein can be used for open as well as endoscopic procedures. It will further be understood that various modifications may be made to the embodiments disclosed herein. For example, a needle pointed at both ends with a suture attached to an intermediate portion can be utilized to enable stitching with either jaw. Also, straight needles as well as curved needles other than that shown are also contemplated. Further, the instruments can be used for endoscopic and non-endoscopic applications. Therefore, the above description should not be construed as limiting but merely as a exemplifications of preferred embodiments. Those skilled in the art will envision other modifications within the scope and spirit of the claims appended hereto.

What is claimed is:

1. An apparatus for suturing body tissue comprising:
   a handle portion;
   an elongated body portion extending from the handle portion and defining a longitudinal axis;
   first and second jaws extending from the body portion;
   a first securing mechanism cooperating with the first jaw and a second securing mechanism cooperating with the second jaw;
   a jaw actuating mechanism operatively associated with at least one of the first and second jaws, wherein the jaw actuating mechanism moves at least one of the jaws longitudinally and parallel to the longitudinal axis; and
   a control mechanism operatively connected to the first and second securing mechanisms, the control mechanism moving at least one of the securing mechanisms between a first position to secure a surgical needle within one of the first and second jaws and a second position to release the surgical needle from the respective jaw.

2. An apparatus as recited in claim 1, wherein the jaw actuating mechanism comprises a button slidably mounted with respect to the handle portion.

3. An apparatus as recited in claim 1, wherein the jaw actuation mechanism includes a first slidable actuator button to move the first jaw and a second slidable actuator button to move the second jaw.

4. An apparatus as recited in claim 3, wherein movement of the first actuator button distally slides the first jaw distally and movement of the second actuator distally slides the second jaw distally.

5. An apparatus as recited in claim 1, wherein the control mechanism comprises first and second control levers pivotally mounted with respect to the handle portion.

6. An apparatus as recited in claim 3, wherein the control mechanism comprises first and second control levers pivotally mounted with respect to the handle portion.

7. An apparatus as recited in claim 6, wherein the first and second control levers are mounted to the first and second actuator buttons, respectively, such that each control lever is carried by the respective actuator button.

8. An apparatus as recited in claim 7, wherein each of the actuator buttons has an aperture formed therein and a portion of the respective control lever protrudes through the aperture.

9. An apparatus as recited in claim 1, wherein each of the jaw members has a needle receiving notch formed therein, and each of the securing members is slidable distally to retain the needle in the notch of the jaw member.

10. An apparatus of claim 9, wherein each securing member extends from an elongate rod connected at a proximal end to the respective control member.

11. An apparatus of claim 9, wherein each of the securing members has an angled distal surface to press the needle into the notch of the respective jaw member.

12. An apparatus as recited in claim 1, wherein the first and second jaws move parallel to each other.

13. An apparatus for suturing body tissue comprising:
    a handle portion;
    an elongated body portion extending distally from the handle portion and defining a first longitudinal axis;
    first and second jaws extending from the body portion defining a second longitudinal axis;
    a surgical needle releasably held within at least one of the first and second jaws and positioned perpendicularly to the second longitudinal axis of the first and second jaws;
    a first securing member slidably positioned with respect to the first jaw member and movable in a longitudinal direction between a needle securing position and a needle releasing position; and
    a second securing member slidably positioned with respect to the second jaw member and movable in a longitudinal direction between a needle securing position and a needle releasing position.

14. An apparatus as recited in claim 13, wherein the needle releasing position of the securing member is proximal of the needle securing position.

15. An apparatus as recited in claim 14, further comprising first and second actuator buttons slidable longitudinally between a proximal and distal position, wherein movement of the first actuator button to the distal position moves the first jaw distally and movement of the second actuator button to a distal position moves the second jaw distally.

16. An apparatus as recited in claim 15, further comprising first and second control members, wherein movement of the first control member to a distal position slides the first securing member distally and movement of the second control member to a distal position slides the second securing member distally.

17. An apparatus of claim 16, wherein the first and second control members are slidably mounted on a handle portion of the apparatus.

18. An apparatus of claim 17, wherein the first and second control members are pivotally mounted on the handle portion of the apparatus.

19. An apparatus of claim 16, wherein each of the jaws has a notch portion formed at a distal end portion for receiving the surgical needle.

20. An apparatus for suturing body tissue comprising:
    a handle portion;
    an elongated body portion extending from the handle portion and defining a longitudinal axis;
    first and second jaw members extending distally from the elongated body portion;
    a surgical needle positionable in either of the jaw members;
    means for reciprocal relative movement of the first and second jaw members between a proximal position and a distal position with respect to the body portion; and
    means for securing the surgical needle in one of the first and second jaw members, the securing means being selectively movable between a retracted and an extended position.

21. An apparatus as recited in claim 20, wherein the securing means includes first and second slidable blades, each of the blades being selectively slidable by a control means operatively connected thereto.

22. An apparatus of claim 21, further comprising actuation means operatively connected to the jaw members for selectively moving the jaw members.

23. An apparatus for suturing body tissue comprising:

a handle portion;

an elongated body portion extending distally from the handle portion and defining a longitudinal axis;

first and second jaws extending from the body portion and movable in a longitudinal direction, wherein at least a portion of each jaw moves within the body portion;

a first securing member positioned adjacent the first jaw member and movable between a needle securing position and a needle releasing position;

a second securing member positioned adjacent the second jaw member and movable between a needle securing position and a needle releasing position;

means for moving the first securing member with respect to the first jaw member between the needle securing and needle releasing positions; and means for moving the second securing member with respect to the second jaw member between the needle securing and the needle releasing positions.

24. The apparatus of claim 23 further comprising:

a control mechanism operatively connected to the first and second jaws, the control mechanism moving the jaws longitudinally relative to one another.

25. An apparatus for suturing body tissue comprising:

a handle portion;

an elongated body portion extending distally from the handle portion and defining a longitudinal axis;

first and second jaws extending from the body portion and moveable in a longitudinal direction with respect to the body portion;

a first securing member positioned adjacent the first jaw member and movable between a needle securing position and a needle releasing position;

a second securing member positioned adjacent the second jaw member and movable between a needle securing position and a needle releasing position;

means for moving the first securing member with respect to the first jaw member between the needle securing and needle releasing positions;

means for moving the second securing member with respect to the second jaw member between the needle securing and the needle releasing positions;

a control mechanism operatively connected to the first and second jaws, the control mechanism moving the jaws longitudinally relative to one another; and timing means associated with the control mechanism for preventing longitudinal motion of a jaw when the corresponding securing member is in the needle securing position.

26. A method of endoscopically suturing tissue comprising the steps of:

(i) providing an endoscopic suturing apparatus having an elongated endoscopic section with first and second longitudinally movable needle holding jaws, the first and second needle holding jaws being movable in a direction parallel to a longitudinal axis of the elongated endoscopic section, and a surgical needle held in at least one of the jaws with a length of suture material attached to the needle;

(ii) endoscopically accessing a surgical site;

(iii) positioning the elongated endoscopic section adjacent the site to be sutured with the needle held in the first jaw, the second jaw being longitudinally retracted relative to the first jaw;

(iv) inserting the needle through tissue;

(v) manipulating the longitudinally movable jaws until both jaws are substantially equally extended;

(vi) grasping the needle with the second jaw;

(vii) releasing the needle from the first jaw; and (viii) drawing the needle and a length of the suture material through the tissue.

27. The method of claim 26 wherein the step of manipulating the longitudinally movable jaws comprises extending the second jaw substantially equally to the first jaw.

28. The method of claim 26 further comprising the steps of:

(ix) retracting the first jaw relative to the second jaw prior to the step of drawing;

(x) subsequent to the step of drawing, manipulating the longitudinally movable jaws until both jaws are substantially equally extended;

(xi) grasping the needle with the first jaw; and (xii) releasing the needle from the second jaw.

29. The method of claim 28 further comprising the steps of:

(xii) manipulating the longitudinally movable jaws so that the first jaw is extended relative to the second jaw.

* * * * *